(12) United States Patent
Parang et al.

(10) Patent No.: US 8,193,384 B2
(45) Date of Patent: Jun. 5, 2012

(54) POLYMER-BOUND PHOSPHITYLATING REAGENTS FOR THE SYNTHESIS OF ORGANOPHOSPHORUS COMPOUNDS

(75) Inventors: Keykavous Parang, Wakefield, RI (US); Yousef Ahamdibeni, Kingston, RI (US)

(73) Assignee: Board of Governors for Higher Education, State of Rhode Island and Providence Plantation, Providence, RI (US)

( * ) Notice: Subject to any disclaimer, the term of this patent is extended or adjusted under 35 U.S.C. 154(b) by 89 days.

(21) Appl. No.: 11/972,254

(22) Filed: Jan. 10, 2008

(65) Prior Publication Data

US 2008/0207551 A1 Aug. 28, 2008

Related U.S. Application Data

(63) Continuation of application No. PCT/US2006/029481, filed on Jul. 28, 2006.

(60) Provisional application No. 60/704,226, filed on Jul. 29, 2005.

(51) Int. Cl.
| | |
|---|---|
| C07F 9/48 | (2006.01) |
| C07F 9/22 | (2006.01) |
| C07F 9/24 | (2006.01) |
| C07F 9/26 | (2006.01) |
| C07F 9/141 | (2006.01) |
| C07F 9/142 | (2006.01) |
| C07F 9/143 | (2006.01) |
| C07F 9/144 | (2006.01) |
| C07F 9/145 | (2006.01) |
| C07F 9/146 | (2006.01) |

(52) U.S. Cl. ........ 558/152; 558/155; 558/156; 558/157; 568/13; 568/14; 568/15; 568/16

(58) Field of Classification Search .................. None
See application file for complete search history.

(56) References Cited

U.S. PATENT DOCUMENTS

| 5,616,700 A | 4/1997 | Reddy et al. |
| 6,528,098 B2 | 3/2003 | Friedland et al. |
| 6,759,461 B2 * | 7/2004 | Wu et al. ........................ 524/150 |
| 2002/0051991 A1 | 5/2002 | Hong et al. |

FOREIGN PATENT DOCUMENTS

WO 2005/013901 A2 2/2005

OTHER PUBLICATIONS

Ebsworth et al., "Preparation and Propert ies of Difluorophosphino-derivatives of Phosphorus(III) Hydroxy-compounds" Journal of the Chemical Society, Dalton Transactions (1983) vol. 2 pp. 1983-1987.*
Baruer et al., "Linear oligophosphaalkanes. XIII. Triphosphaalkanes with the phosphorus-carbon-phosphorus-carbon-phosphorus donor skeleton; ligands for the synthesis of polynuclear complexes" Journal of Organometallic Chemistry (1985) vol. 296 No. 3, pp. 411-433 and English translation of abstract.*
Ahmadibeni et al., "Solid-Phase Reagents for Selective Monophosphorylation of Carbohydrates and Nucleosides" Journal of Organic Chemistry (2005) vol. 70 pp. 1100-1103.*
Parang et al., "A Solid Phase Reagent for the Capture Phosphorylation of Carbohydrates and Nucleosides" Organic Letters (2001) vol. 3 No. 2, pp. 307-309.*
Garegg et al., "Nucleoside Hydrogenphosphonates in Oligonucleotide Synthesis" Chemica Scripta (1986) vol. 26 pp. 59-62.*
Micklefield, Backbone Modification of Nucleic Acids: Synthesis, Structure, and Therapeutic Applications, Current Medical Chemistry, 2001, pp. 1157-1179, vol. 8, Bentham Science Publishers Ltd., United Kingdom.
Uhlmann et al., Antisense Oligonucleotides: A New Therapeutic Principle, Chemical Reviews, Jun. 1990, pp. 543-584, vol. 90, No. 4, American Chemical Society, Germany.
Jepsen et al., LNA-Antisense rivals siRNA for gene silencing, Current Opinion in Drug Discovery & Development, 2004, pp. 188-194, vol. 7, No. 2, The Thomson Corporation ISSN 1367-6733, Denmark.
Koshkin et al., LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition, Tetradhedron, 1998, pp. 3607-3630, vol. 54, Elsevier Science Ltd., Denmark.
Burgess et al., Syntheses of Nucleoside Triphosphates, Chemical Reviews, 2000, pp. 2047-2059, vol. 100, American Chemical Society, USA.
DeSaubry et al., Synthesis of 2'-Deoxy- and 2' ,5'-Dideoxy-Adenosine-3'-Di- and 3'-Triphosphate, Tetrahedron Letters, 1995, pp. 995-996, vol. 36, No. 7, Elsevier Science Ltd., Great Britain.
Shoshani et al., Inhibition of Adenylyl Cyclase by Acyclic Nucleoside Phosphonate Antiviral Agents, The Journal of Biological Chemistry, Dec. 1999, pp. 34742-34744, vol. 274, No. 49, The American Society for Biochemistry and Molecular Biology, Inc., USA.
Bettendorff et al., A general method for the chemical synthesis of y-32P-labeled or unlabeled nucleoside 5'-triphosphates and thiamine triphosphate, Analytical Biochemistry, 2003, pp. 190-197, vol. 322, Elsevier Science Inc., France.

(Continued)

Primary Examiner — Eric S Olson
(74) Attorney, Agent, or Firm — Gesmer Updegrove LLP

(57) ABSTRACT

The synthesis and biochemical utility of modified oligonucleotides containing diphosphodiester internucleotide linkages. The synthesis of these compounds was carried out using diphosphitylating reagents. Oligonucleotides containing diphosphate diester bridges wherein said oligonucleotides are synthesized via a solid-phase synthesis strategy to form modified oligonucleotides. Diphosphitylating, triphosphitylating, tetraphosphitylating, β-triphosphitylating, bifunctional diphosphitylating, bifunctional triphosphitylating, and bifunctional tetraphosphitylating reagents wherein, the phosphorus atoms are linked together through oxygen, sulfur, amino, or methylene groups and/or are substituted with chlorine, diisopropylamine and cyanoethoxy groups.

10 Claims, 16 Drawing Sheets

OTHER PUBLICATIONS

Wu et al., A Novel Method for the Preparation of Nucleoside Triphosphates ffrom Activated Nucleoside Phosphoramidates, Organic Letters, 2004, pp. 2257-2260, vol. 6, No. 13, American Chemical Society, USA.

Ahmadibeni et al., Solid-Phase Reagants for Selective Monophosphorylation of Carbohydrates and Nucleosides, J. Org. Chem., 2005, pp. 1100-1103, vol. 70, American Chemical Society, USA.

Ahmadibeni et al., Application of a Solid-Phase B-Triphosphitylating Reagent in the Synthesis of Nucleoside B-Triphosphates, J. Org. Chem., 2006, pp. 5837-5839, vol. 71, American Chemical Society, USA.

Ahmadibeni et al., Selective Diphosphorylation, Dithiodiphosphorylation, Triphosphorylation, and Triphosphorylation of Unprotected Carbohydrates and Nucleosides, Organic Letters, 2005, pp. 5589-5592, vol. 7, No. 25, American Chemical Society, USA.

European Search report based on PCT/US2006/029481, dated Oct. 18, 2010, 12 pages.

Shabarova, Chemical development in the design of oligonucleotide probes for binding to DNA and RNA, Biochemie, 1988, pp. 1323-1334, vol. 70, Societe de Chimie biologique, France.

Sokolova et al., Chemical Reactions with DNA Duplexes: Cyanogen bromide as an effective oligodeoxyribonucleotide coupling agent, Febs Letters, May 1998, pp. 153-155, vol. 232, No. 1, Elsevier Science, Moscow, Russia.

Sugimura, Poly(adenosine diphosphate ribose), Progress in Nucleic Acid Research, 1973, pp. 127-151, vol. 7, Europe.

Patent Cooperation Treaty search report, based on International application No. PCT/US06/29481, with an international filing date of Jul. 28, 2006, 11 pages.

\* cited by examiner n = 1-3
X = O or S

R = nucleosides or carbohydrates

SEQUENCE LISTING

<160> NUMBER OF SEQ ID NOS: 8

<210> SEQ ID NO 1
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
aaaaaaaaaa aa                                                             12

<210> SEQ ID NO 2
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tttttttttt tt                                                             12

<210> SEQ ID NO 3
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
cccccccccc cc                                                             12

<210> SEQ ID NO 4
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gggggggggg gg                                                             12

<210> SEQ ID NO 5
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
atatatatat at                                                             12

<210> SEQ ID NO 6
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6

-continued

```
tatatatata ta                                                          12

<210> SEQ ID NO 7
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
cgcgcgcgcg cg                                                          12

<210> SEQ ID NO 8
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gcgcgcgcgc gc                                                          12
```

POLYMER-BOUND PHOSPHITYLATING REAGENTS FOR THE SYNTHESIS OF ORGANOPHOSPHORUS COMPOUNDS

PRIORITY INFORMATION

This application is a continuation of International Patent Application No. PCT/US2006/029481, filed on Jul. 28, 2006 and claims priority to U.S. Provisional Patent Application 60/704,226, filed on Jul. 29, 2005, all of which are incorporated herein by reference in their entirety.

BACKGROUND OF THE INVENTION

During the past two decades, chemically modified oligodeoxynucleotides (ODNs) have received much attention in search for potential therapeutic and diagnostic agents and in the study of numerous biochemical and biological processes. The use of modified ODNs as specific targeting of gene expression has become an indispensable tool in antisense research. There has been a revival of interest in gene silencing since the discovery that short interfering RNA (siRNA) molecules can affect RNA interference in mammalian cells.

ODNs have been extensively modified in order to enhance their stability to nuclease, cell penetration ability, selectivity, binding affinity toward complementary nucleic acids, and the melting temperature ($T_m$) of formed duplex. To a great extent, these modifications have focused on replacing the phosphodiester group or the whole deoxysugar-phosphodiester backbone with alternative anionic, cationic, and neutral structures. Some examples include using peptide nucleic acid (PNA), bicyclic oligonucleotides as locked nucleic acids (LNA), modified sugars such as hexitol nucleic acid (HNA), and phosphodiester mimics.

A number of phosphodiester mimics have been synthesized by replacing the phosphate group. These phosphodiester mimics include phosphorothioate, methylphosphate, phosphoramidates, boranophosphate, alkylphosphotriesters, phosphorodithioate, phosphonomethyl, propynes, diene, phosphonoformate, and other groups. The phosphate-modified DNA oligomers have been extensively used in biological research as inhibitors of gene expression, viral enzymes such as HIV reverse transcriptase, in vitro mRNA translation, and sequence-specific DNA binding proteins when present in duplex form.

Nucleosides are intracellularly converted to nucleoside monophosphates, diphosphates, and triphosphates, respectively, in the presence of kinases. Diphosphorylation and triphosphorylation are required for the synthesis of nucleotides and nucleic acids thus producing biological activity of all nucleosides, as shown in several antiviral and anticancer drugs.

SUMMARY OF THE INVENTION

This invention describes the synthesis and potential biochemical utility of modified oligonucleotides containing diphosphodiester internucleotide linkages. The synthesis of these compounds was carried out by using novel diphosphitylating reagents. The reagents used for synthesizing these modified oligonucleotide molecules may be highly valuable in pharmaceutical and chemical industry.

Described is the synthesis and potential biochemical utility of modified oligonucleotides containing diphosphate diester internucleotide linkages (FIG. 1). The compounds have a larger distance between 5' and 3' oxygens of two nucleotides across the internucleotide bridge compared to that in the natural ODNs. The potential of modified ODNs for forming a double-stranded DNA by binding with modified and unmodified complementary chains was investigated and compared with natural DNA chains to establish a new family of chemically modified ODNs.

The oligomers containing diphosphate diester bridges form stable antiparallel duplex structures based on thermal denaturation studies and CD analysis. Modified ODNs displayed hybridization affinity toward complementary modified chains. No thermal transition was detected when applying the same conditions to unmatched chains. A preference for hybridization to modified oligomers was revealed for a number of modified self-complementary ODNs such as 5'-d(ATATATATAT) (SEQ ID NO: 5) or 5'-d(TATATATATA) (SEQ ID NO: 6) relative to that obtained with the unmodified-unmodified duplexes. The CD spectra of the modified-modified self-complementary oligomers were significantly blue shifted when compared to those of the unmodified-unmodified analogues, possibly due to the conformational changes resulted from different hydration patterns of diphosphodiester group and/or larger sugar-sugar separation. In general, the chemically modified ODNs has the ability to bind to complementary unmodified strands, suggesting that these compounds may have potential applications in antisense and nucleic acid research for developing inhibitors against specific sequences of ODNs. Furthermore, these modified molecules may have applications as antisense molecules for silencing the activity of disease-causing genes. The diseases include cancer or other genetically related diseases. Disclosed are chemically modified ODNs containing diphosphodiester bridges.

Another aspect of this invention is the synthesis of a number of diphosphitylating triphosphitylating, and tetraphosphitylating reagents used for the synthesis of oligonucleotides containing diphosphodiester internucleotide linkages (FIG. 1) and the synthesis of other phosphorylated analogues (FIG. 2). Diphosphitylating reagents were used for the synthesis of chemically modified ODNs containing diphosphodiester bridges in this invention. Another related aspect of this invention is the synthesis of a solid-phase β-triphosphitylating reagent and its application for the synthesis of nucleoside β-triphosphates (FIG. 2). Diphosphitylating, triphosphitylating, tetraphosphitylating, and β-triphosphitylating reagents were used in the synthesizing of nucleoside and carbohydrate diphosphates, dithiodiphosphates, triphosphates, trithiotriphosphates, tetraphosphates, tetrathiotetraphosphates, and β-triphosphates. In other words, these reagents were used for selective diphosphorylation, dithiodiphosphorylation, triphosphorylation, trithiotriphosphorylation, tetraphosphorylation, and β-triphosphorylation of unprotected carbohydrates and nucleosides (FIG. 2). The selective diphosphorylation, dithiodiphosphorylation, triphosphorylation, and trithiotriphosphorylation of unprotected carbohydrates are challenging goals for organic chemists. Diphosphorylation and triphosphorylation are required for the synthesis of nucleotides and nucleic acids thus producing biological activity of all nucleosides, as shown in several antiviral drugs. A number of chemical strategies have been previously reported for diphosphorylation and triphosphorylation of nucleosides in solution, e.g., the reaction of nucleoside phosphoramidates (e.g., morpholidate) or phosphorodichloridates with bis(tri-n-butylammonium)pyrophosphate derivatives or the reaction of nucleoside diphosphates and their derivatives (e.g., morpholidate, imidazolidate) with phosphoric acid. These synthetic strategies have been hampered by one or more of the following difficulties: (i) The reactions generally must be carried out in anhydrous organic solvents. Because of the poor solubility of most precursor phosphates in the reaction mixture, the yield is low in most cases; (ii) For triphosphorylation in solution, the phosphoramidates and phosphorodichloridates are needed to be synthesized first; (iii) Extensive purification of intermediates and final products from the reagents is required; (iv) These strategies involve protection and deprotection reactions for carbohydrates and lead in most cases to low overall yield due to the lack of regioselectivity; and (v) The synthesis of dithiodiphosphate and trithiotriphosphate derivatives from the corresponding diphosphate and triphosphate derivatives in solution phase often leads to the incorporation of two sulfur atoms (disulfurization) on the terminal phosphorus atom.

To solve one or more of these problems, this invention describes the solid-phase diphosphorylation, dithiodiphosphorylation, triphosphorylation, and trithiotriphosphorylation of unprotected carbohydrates and nucleosides. In this invention carbohydrate and nucleoside diphosphates, diphosphodithioates, triphosphates, and triphosphotrithioates were synthesized by using solid-phase reagents. This strategy offered several advantages: (i) The main advantage of this chemical procedure was that it produced one type of monosubstituted derivatives. Similar reactions in solution phase yield a mixture of polysubstituted products; (ii) The alcohols (unprotected nucleosides and carbohydrates) were mixed with an immobilized reagent and were thereby "captured" as an immobilized compound. Washing the support allowed for removal of unreacted reagents, and guaranteed that no unreacted starting materials remained; (iii) This approach made use of the presence of reagents on a rigid solid support having a hindered structure, thereby allowed for the regioselective reaction. The most reactive hydroxyl group of carbohydrates and nucleosides reacted selectively with hindered polymer-bound reagents when an excess of carbohydrates and nucleoside was used; (iv) Reactions using this strategy offered the advantage of facile isolation and the recovery of products. The linkers remained trapped on the resins, which facilitated the separation of the monosubstituted final products by filtration; (v) This method was used for synthesis of five classes of compounds, nucleoside and/or carbohydrate diphosphates, triphosphates, dithiodiphosphates, trithiotriphosphates, and β-triphosphates from the same polymer-bound linker; and (vi) Additionally, for the dithiodiphosphorylation and trithiotriphosphorylation reactions in the solid-phase, the terminal oxygen of the phosphorus is linked to the resin and does not react with Beaucage's reagent; therefore, only monosulfurization occurs on the terminal phosphorus atom.

Another aspect of this invention is the synthesis of a solid-phase β-triphosphitylating reagent and its application for the synthesis of nucleoside β-triphosphates. Only monosubstituted nucleoside 5'-O-β-triphosphates were produced. The presence of a β-triphosphitylating reagent on a hindered and rigid solid support only allows the reaction with the most reactive and exposed hydroxyl group in the nucleosides. The solid-phase strategy also offers the advantage of facile isolation and the recovery of products. The unprotected nucleosides were mixed with the polymer-bound reagent. Washing the support allowed for removal of unreacted reagents and starting materials. Furthermore, in the final reaction, the linker remained trapped on the resin, which facilitated the separation of the monosubstituted final products by filtration.

Another aspect of this invention is the synthesis and use of novel bifunctional diphosphitylating, triphosphitylating, and tetraphosphitylating reagents, and polymer-bound bifunctional diphosphitylating, triphosphitylating, and tetraphosphitylating reagents for the synthesis of nucleoside and carbohydrate diphsphodiesters, tiphosphodiesters, and tetraphosphodiesters (FIG. 2). These compounds may have applications as antiviral or anticancer agents or as prodrugs of active nucleoside or carbohydrate analogues.

BRIEF DESCRIPTION OF THE DRAWINGS

Other objects, features and advantages of the present invention will become more apparent as the description proceeds with reference to the accompanying drawings, wherein.

DETAILED DESCRIPTION OF THE INVENTION

1. Modified ODNs Containing Diphosphate Diester Linkages

Figure 1:
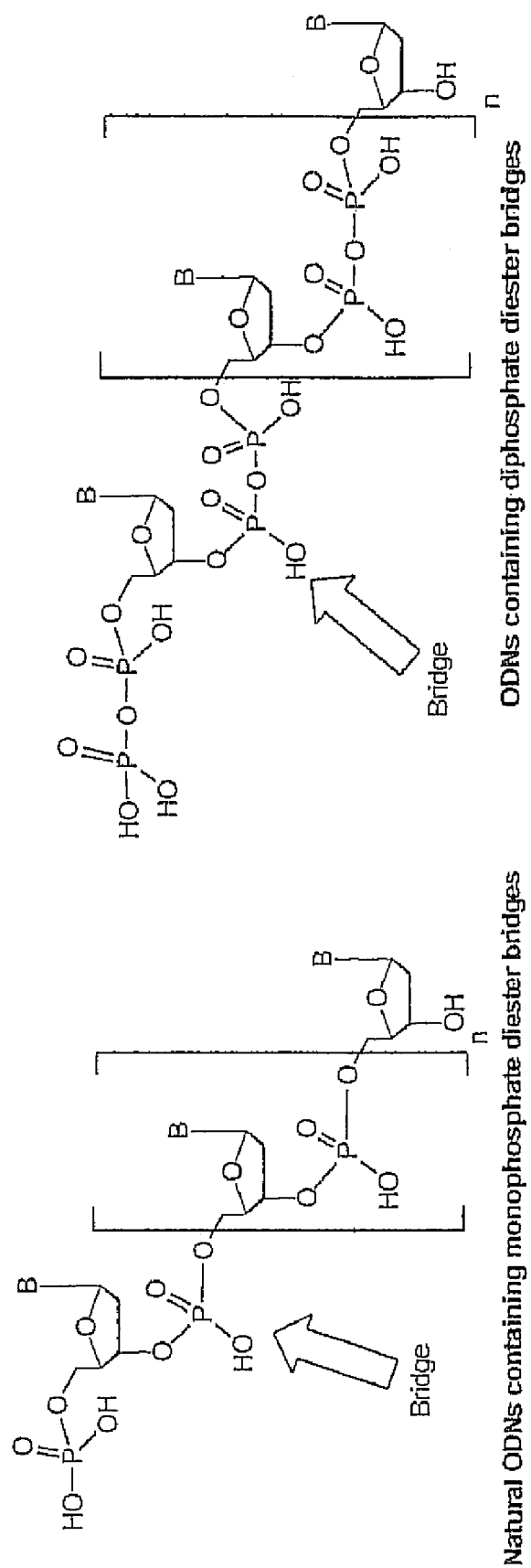
FIG. 1 shows structures of unmodified single-stranded DNA oligomers containing monophosphate diester bridges and modified ODNs containing diphosphate diester bridges.
Figure 2:
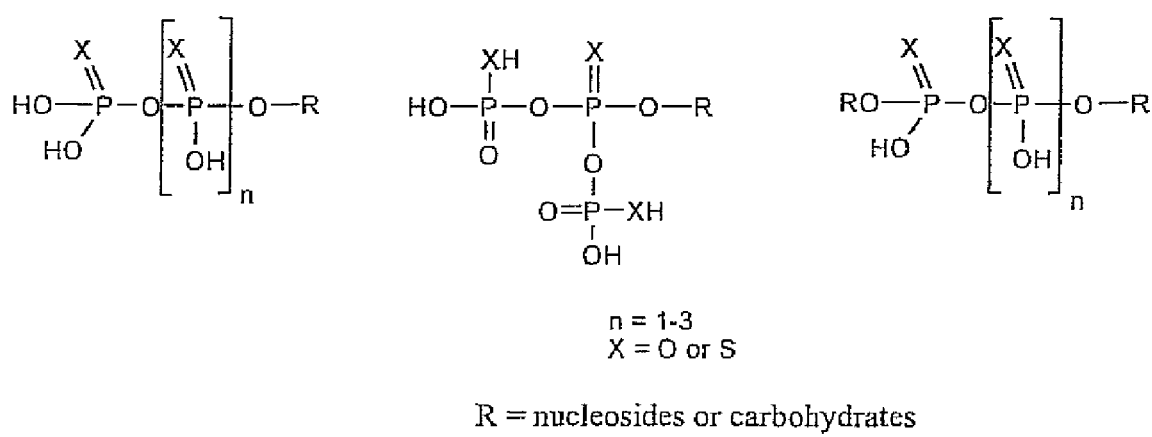
FIG. 2 shows structures of organophosphorus derivatives of nucleosides and carbohydrates synthesized using solid-phase reagents.
Figure 3:
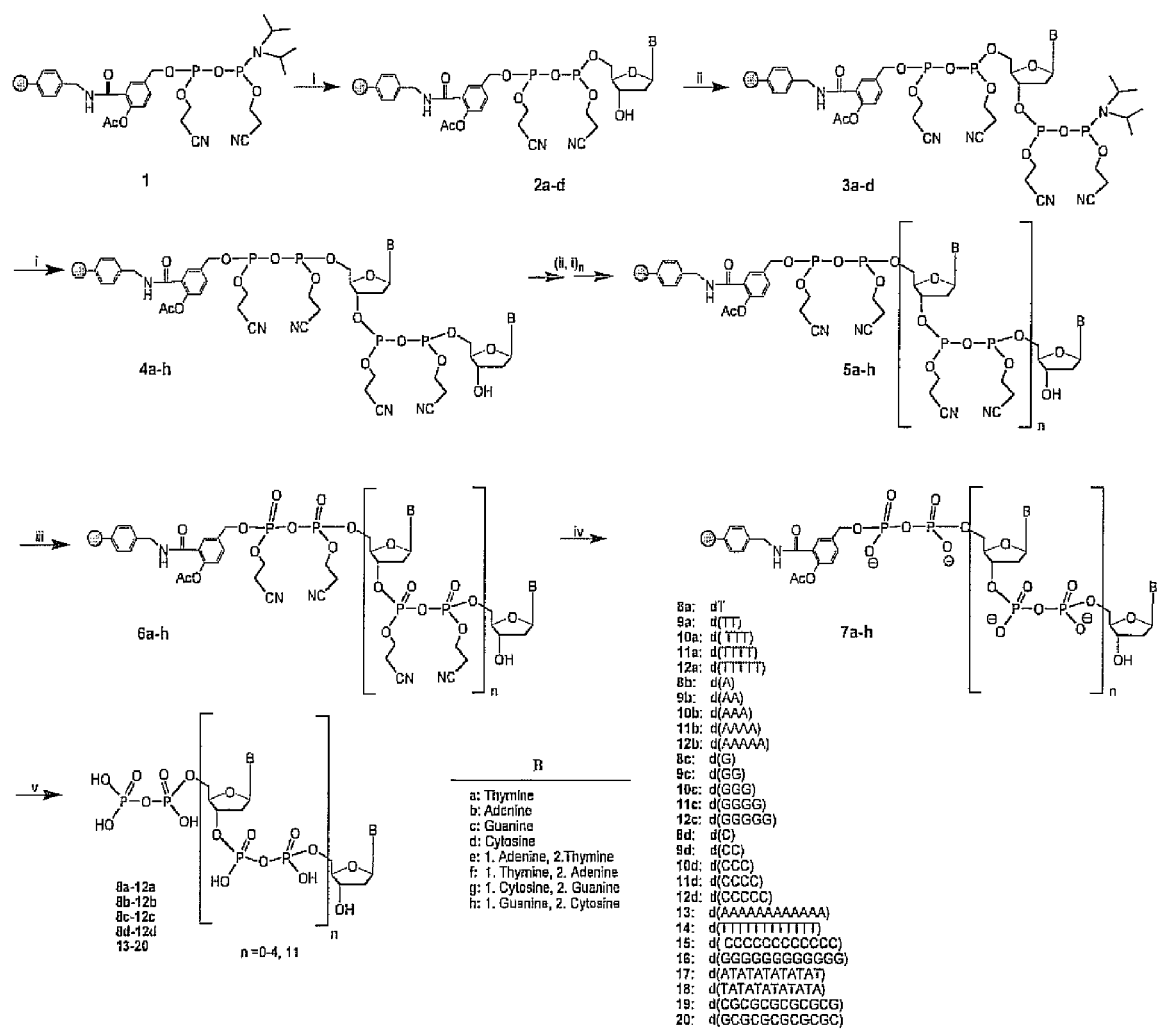
FIG. 3 shows synthesis of modified ODNs containing diphosphate diester internucleotide linkages; Figure discloses SEQ ID NOS: 1-8, respectively, in order or appearance.

Chemistry. Synthesis of the modified ODNs was accomplished as shown in FIG. 3. The synthesis of nucleoside and carbohydrate diphosphates and dinucleoside diphosphodiesters is described using a solid-supported diphosphitylating reagent in the second part of this invention. Aminomethyl polystyrene resin-bound linker of p-acetoxybenzyl alcohol was subjected to reaction with the diphosphitylating reagent, bis(2-cyanoethyl diisopropylphosphoramidite) ([(i-Pr)$_2$NPOCH$_2$CH$_2$CN]$_2$O), in the presence of 1H-tetrazole to produce polymer-bound diphosphitylating reagent 1 that was used for the synthesis of modified ODNs. This strategy offers the advantages of use of unprotected nucleosides and facile isolation of final products. The solid-supported reagent reacted first with the exposed and reactive 5'-hydroxyl group in unprotected nucleosides. Free 3'-hydroxyl group was used for subsequent stepwise diphosphitylation.

The synthesis cycle consists of six chemical reactions that are separated by washing steps designed to remove excess reagents: (i) immobilization of 5'-hydroxyl group of the first unprotected nucleoside (e.g., dT, dA, dG, dC) through the reaction with solid-supported reagent 1 in the presence of 1H-tetrazole to afford 2a-d; (ii) diphosphitylation of the 3'-hydroxyl group with bis(2-cyanoethyl diisopropylphosphoramidite) in the presence of 1H-tetrazole to yield 3a-d; (iii) repeating steps i and ii (coupling and diphosphitylation reactions) n times (n=0-4, 11) to produce polymer-bound diphosphite triesters (5a-h); (iv) oxidation with t-butyl hydroperoxide to yield polymer-bound diphosphate triesters (6a-h); (v) removal of 2-cyanoethoxy group in the presence of DBU to produce polymer-bound diphosphate diester (7a-h); and (vi) cleavage of final products (8-20) from the solid support in the presence of DCM/TFA/H$_2$O/1,2-ethanedithiol. The residues were mixed with Amberlite AG-50W-X8 (100-200 mesh, hydrogen form, 500 mg, 1.7 meq/g). Repetition of this synthesis cycle allowed for assembly of different ODNs. In total, by using different numbers and combinations of nucleosides, 28 compounds were synthesized in 30 mg scale.

First, ODNs containing 5 base pairs or less (n=0-4) were synthesized to examine the feasibility of the synthesis. The crude products had a purity of 66-94% and were purified by using small C$_{18}$ Sep-Pak cartridges and appropriate solvents to afford ODNs up to five base pairs containing diphosphodiester bridges (8-12 a-d) in 47-78% (overall yield calculated from 1) (Table 1).

TABLE 1

Overall isolated yields and purity of crude products for modified ODNs containing diphosphate diester linkage (8-20).

| Oligomers | Overall yield (%) calcd from 1 | Purity of crude products (%) |
|---|---|---|
| 8a | 75 | 89 |
| 8b | 68 | 83 |
| 8c | 65 | 78 |
| 8d | 59 | 66 |
| 9a | 52 | 69 |
| 9b | 62 | 81 |
| 9c | 58 | 85 |
| 9d | 54 | 77 |
| 10a | 51 | 69 |
| 10b | 47 | 75 |
| 10c | 70 | 91 |
| 10d | 67 | 87 |

TABLE 1-continued

Overall isolated yields and purity of crude products for modified ODNs containing diphosphate diester linkage (8-20).

| Oligomers | Overall yield (%) calcd from 1 | Purity of crude products (%) |
|---|---|---|
| 11a | 64 | 82 |
| 11b | 61 | 79 |
| 11c | 58 | 74 |
| 11d | 78 | 94 |
| 12a | 74 | 91 |
| 12b | 70 | 88 |
| 12c | 66 | 83 |
| 12d | 62 | 85 |
| 13 | 41 | 87 |
| 14 | 37 | 79 |
| 15 | 44 | 91 |
| 16 | 33 | 78 |
| 17 | 36 | 59 |
| 18 | 32 | 81 |
| 19 | 37 | 74 |
| 20 | 39 | 68 |

Figure 4:
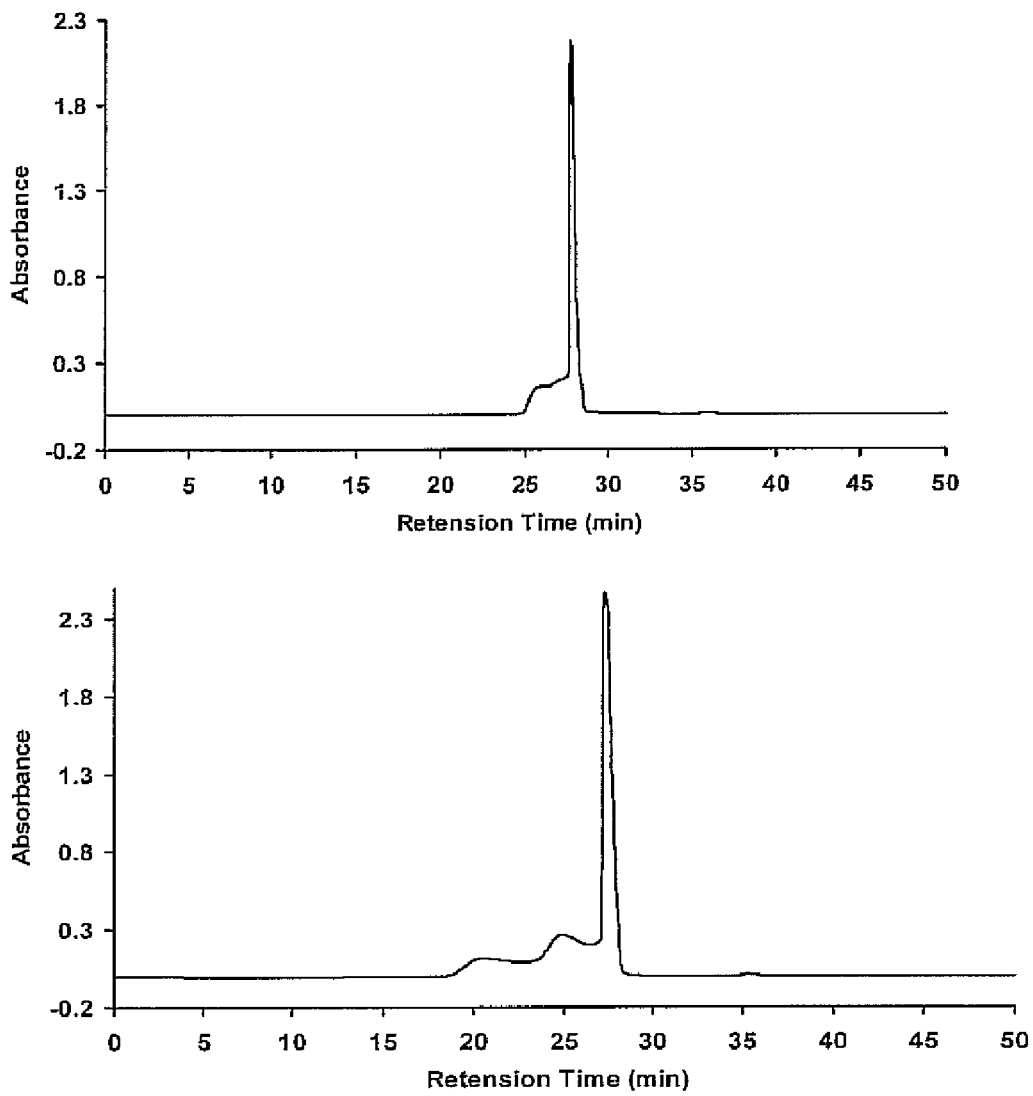
FIG. 4 shows reverse phase HPLC of the crude product of d(TTTTTTTTTTTT) (SEQ ID NO: 2) (14) (left) and d(GGGGGGGGGGGG) (SEQ ID NO: 4) (16) (right)

The synthetic cycle was then used to synthesize modified ODNs with 12 bases. The crude products had a purity of 59-91% and were purified first by using small C$_{18}$ Sep-Pak cartridges and appropriate solvents. Selected fractions containing the final products were repurified using reverse phase HPLC to afford ODNs with 12 base pairs containing diphosphodiester bridges in 32-44% (overall yield calculated from 1) (Table 1). Reverse phase HPLC of the crude products showed a broad peak (25-30 min) with only minor contaminants (FIG. 4). No failure sequences were observed and all 12-mer ODNs were successfully purified by using reverse phase HPLC.

Figure 5:
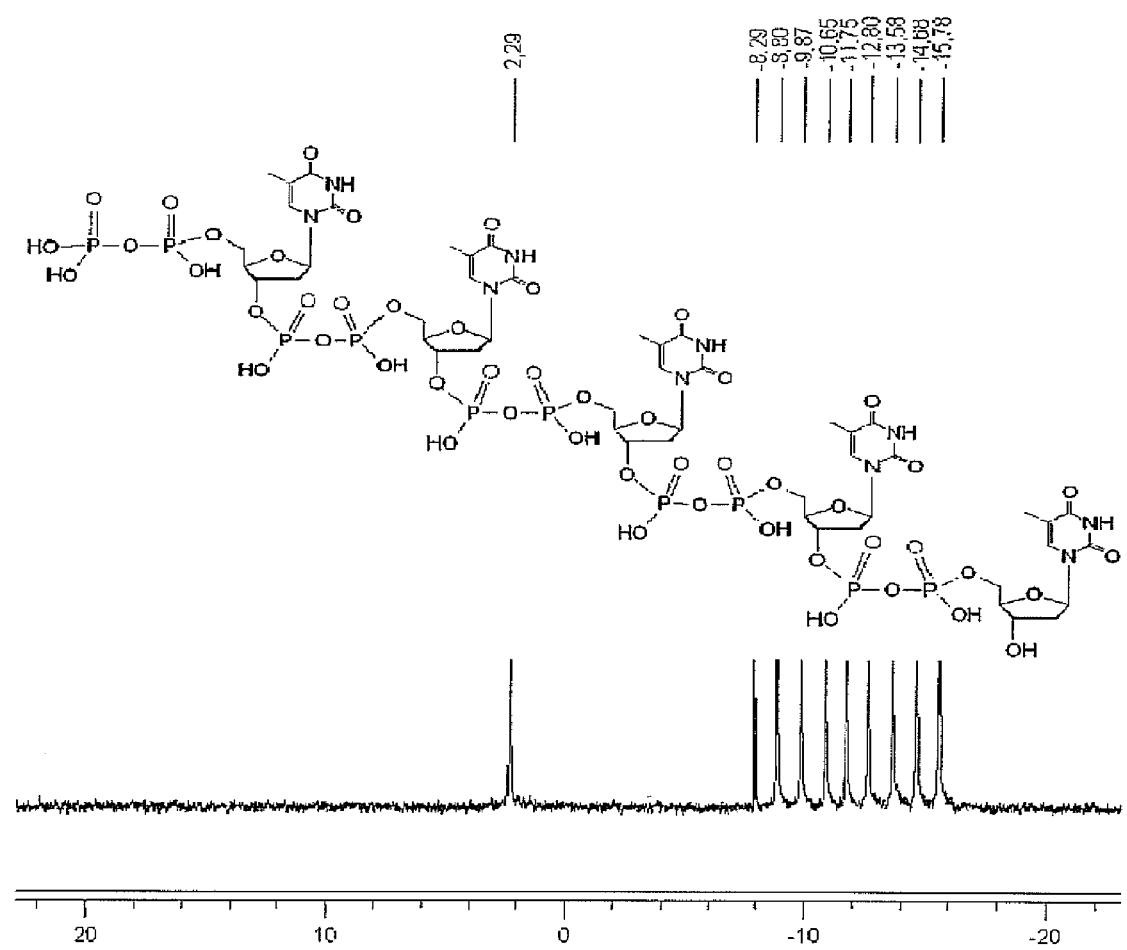
FIG. 5 shows decoupled $^{31}$P NMR of thymidine 5-mer analogue (12a) containing diphosphate diester bridges.

The final products containing 5 base pairs were characterized by nuclear magnetic resonance spectra ($^1$H NMR, $^{13}$C NMR, and $^{31}$P NMR), high-resolution time-of-flight electrospray mass spectrometry, and quantitative phosphorus analysis. For example, fully decoupled $^{31}$P NMR for thymidine 5-mer analogue (12a) displayed 10 non-overlapping peaks corresponding to 10 phosphorus atoms having chemical shifts between −15.78 to 2.29 ppm. The downfield peak at 2.29 ppm was more deshielded compared to other phosphorus atoms and corresponds to the terminal β phosphorus atom (FIG. 5). A similar pattern was observed for all other modified ODNs. It is known that the chemical shifts for phosphorus atoms are pH-dependent. Proton exchange resin was used to exchange all salt anions with hydrogens. In this condition, the terminal phosphorus atom attached to two hydroxyl groups was more deshielded when compared to other phosphorus atoms attached to one hydroxyl group.

Purified modified ODNs with 12 base pairs included d(AAAAAAAAAAAA) (SEQ ID NO: 1) (13), d(TTTTTTTTTTTT) (SEQ ID NO: 2) (14), d(CCCCCCCCCCCC) (SEQ ID NO: 3) (15), d(GGGGGGGGGGGG) (SEQ ID NO: 4) (16), d(ATATATATATAT) (SEQ ID NO: 5) (17), d(TATATATATATA) (SEQ ID NO: 6) (18), d(CGCGCGCGCGCG) (SEQ ID NO: 7) (19), and d(GCGCGCGCGCGC) (SEQ ID NO: 8) (20). The final products were characterized by nuclear magnetic resonance spectra ($^1$H NMR and $^{31}$P NMR), MALDI-TOF mass spectrometry, and quantitative phosphorus analysis (Table 2).

Figure 6:
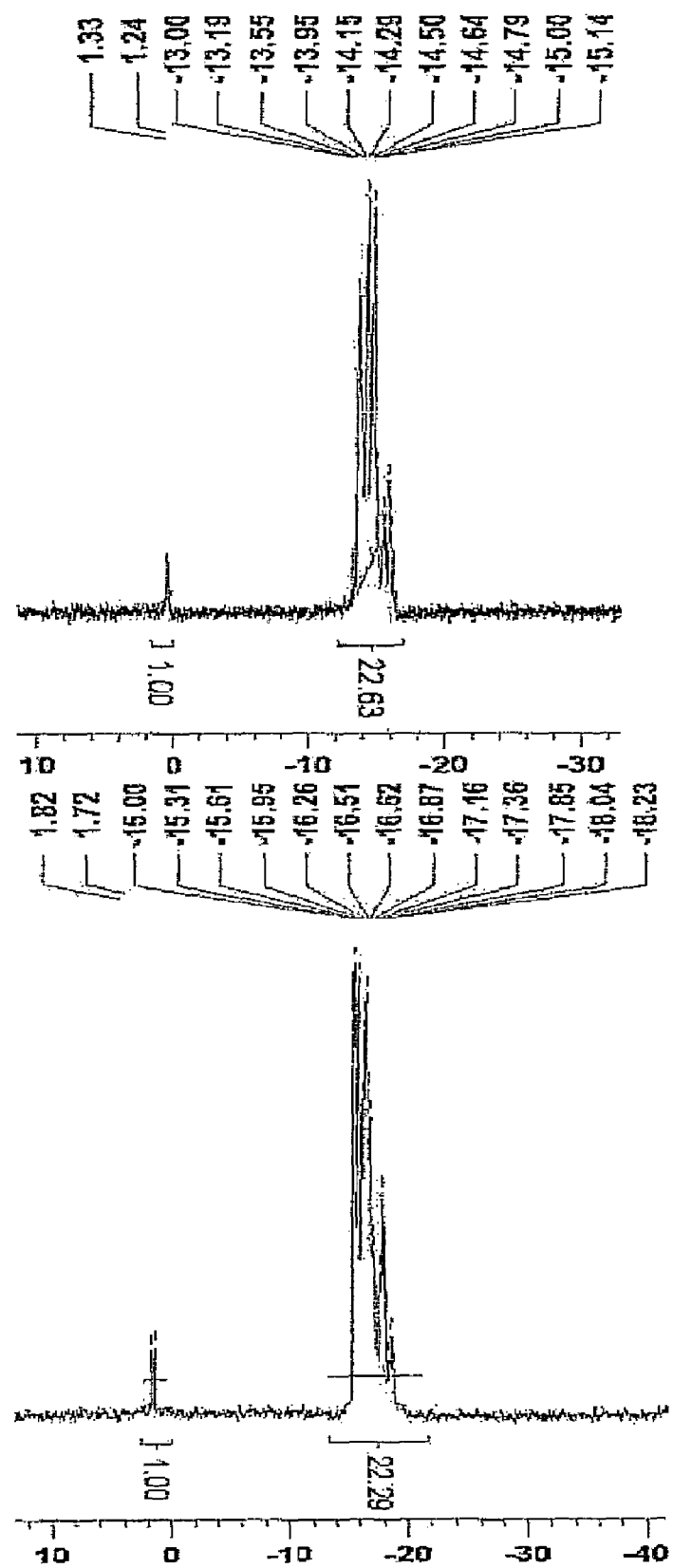
FIG. 6 shows coupled $^{31}$P NMR of 12-mer ODNs containing diphosphate diester bridges: 5'-d(TTTTTTTTTTTT) (SEQ ID NO: 2) (14) (left) and 5'-d(CGCGCGCGCGCG) (SEQ ID NO: 7) (19) (right)

Coupled $^{31}$P NMR of modified 12-mer analogues 14 and 19 displayed peaks with chemical shifts between −18.23 and 1.33 ppm corresponding to 24 phosphorus atoms in each compound. The doublet downfield doublet peaks centered at 1.29 ppm (J=14.6 Hz) and 1.77 ppm (J=16.2 Hz) for 14 and 19, respectively, correspond to the terminal phosphorus atoms (FIG. 6). The peak integrations show the presence of approximately 24 phosphorous atoms in both 12-mer analogues.

TABLE 2

Characterization of 12-mer modified ODNs containing diphosphodiester linkage (SEQ ID NOS 1-8, respectively, in order or appearance).

| Oligomer | Structure | Calcd Mass (g/mol) | Found Mass (g/mol) | Anal. Calcd. P (%) | Anal. Found P (%) |
|---|---|---|---|---|---|
| 13 | d(AAAAAAAAAAAA) | 4734.3 | 4734.2 [M]+ | 15.70 | 15.91 |
| 14 | d(TTTTTTTTTTTT) | 4626.2 | 4627.9 [M + 1]+ | 16.06 | 15.87 |
| 15 | d(CCCCCCCCCCCC) | 4446.2 | 4446.9 [M]+ | 16.71 | 16.63 |
| 16 | d(GGGGGGGGGGGG) | 4926.2 | 4927.8 [M + 1]+ | 15.08 | 15.27 |
| 17 | d(ATATATATATAT) | 4680.2 | 4681.0 [M + 1]+ | 15.88 | 15.72 |
| 18 | d(TATATATATATA) | 4680.2 | 4681.0 [M + 1]+ | 15.88 | 16.09 |
| 19 | d(CGCGCGCGCGCG) | 4686.2 | 4687.2 [M + 1]+ | 15.86 | 15.74 |
| 20 | d(GCGCGCGCGCGC) | 4686.2 | 4687.3 [M + 1]+ | 15.86 | 16.12 |

Thermal Denaturation Studies

Figure 7:
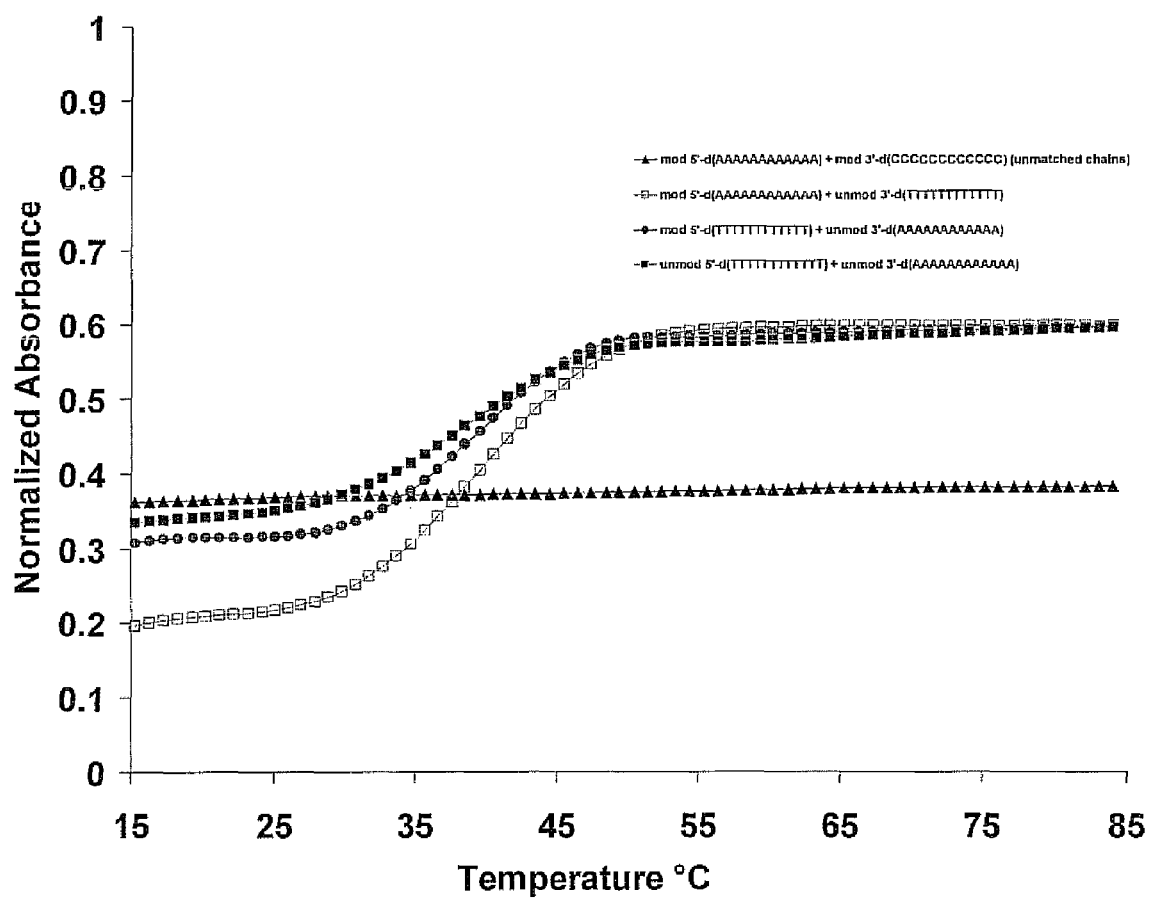
FIG. 7 shows UV melting curves monitored at 260 nm. Experiments were performed in the buffer (pH 7.2) containing $NaH_2PO_4$ (10 mM), $Na_2HPO_4$ (21 mM), NaCl (200 mM), and EDTA (0.20 mM); d(AAAAAAAAAAAA), d(TTTTTTTTTTTT) and d(CCCCCCCCCCCC) disclosed as SEQ ID NOS 1-3, respectively.

The ability of a number of synthesized modified ODNs to form a duplex with complementary chains of modified and unmodified ODNs was examined by UV melting point measurements at 260 nm and a concentration of 1 µM for each strand (pH 7.2, 200 mM NaCl). Some of the sequences (17-20) were self-complementary. As expected, no melting transition was observed for 5-mer modified ODNs. These ODNs are too short to create a meaningful duplex. However, the melting curves for 12-mer ODNs showed a single cooperative transition for all complementary oligomers (see FIG. 7 for examples of matched and unmatched ODNs).

The sequences of duplexes and $T_m$ values are summarized in Table 3. All modified ODNs had duplex-forming ability with complementary modified ODNs as shown by UV melting experiments. Mixtures (1:1) of two complementary strands yield characteristics sigmoidal melting curves.

Modified self-complementary d(ATATATATATAT) (SEQ ID NO: 5) (17) ($\Delta T_m$=+1.8° C.) and d(TATATATATATA) (SEQ ID NO: 6) (18) ($\Delta T_m$=+3.2° C.) displayed enhanced hybridization affinity toward their complementary chains, relative to the unmodified-unmodified ODN duplex controls. ODN duplexes incorporating non-self-complementary modified 5'-d(AAAAAAAAAAAA) (SEQ ID NO: 1) (13)+modified 3'-d(TTTTTTTTTTTT) (SEQ ID NO: 2) (14) ($\Delta T_m$=0.3° C.), were found to have slightly higher melting temperatures relative to those containing unmodified-unmodified chains. These data suggest that modified oligomers can form stable structures with complementary modified chain, but the binding affinity is slightly different when comparing self-complementary duplexes with those of non-self complementary.

Furthermore, the stabilities of different modified ODNs were analyzed in the presence of unmodified complementary chains by thermal denaturation experiments. Modified ODNs showed the ability to bind to the complementary chains of unmodified ODNs. The binding affinities of modified ODNs to unmodified ODNs were not significantly different when compared to those of modified ODNs for most of oligomers. Generally, the differences were in the range of 0 to +1.8 when modified ODNs containing A and T bases annealed with unmodified ODNs and compared to the analogous containing modified-modified duplexes. Modified 5'-d(GGGGGGGGGGGG) (SEQ ID NO: 4) (16) exhibit a higher binding affinity towards modified 3'-d(CCCCCCCCCCCC) (SEQ ID NO: 3) than that of unmodified 3'-d(CCCCCCCCCCCC) (SEQ ID NO: 3).

In general, $T_m$ values for self-complementary modified-unmodified ODNs were slightly higher than those values of the corresponding unmodified-unmodified DNA duplexes (natural DNA) ($\Delta T_m$=0.1-1.4° C.). $T_m$ values of duplexes containing modified 5'-d(ATATATATATAT) (SEQ ID NO: 5) (17) or modified 5'-d(TATATATATATA) (SEQ ID NO: 6) (18) and their complementary unmodified oligomers were slightly higher than those of the corresponding unmodified-unmodified duplexes. These oligomers are self-complementary and it is possible that different forms of oligomers are present in the mixture, including modified-modified, modified-unmodified, and unmodified-unmodified duplexes. On the other hand, non-self-complementary oligomers, such as modified 5'-d(AAAAAAAAAAAA) (SEQ ID NO: 1) (13) and modified 5'-d(TTTTTTTTTTTT) (SEQ ID NO: 2) (14) were able to bind to their complementary unmodified oligomers as shown with $T_m$ values of 39.7° C. and 39.5° C., respectively. These results suggest that the modified oligomers can form also stable complexes with their natural complementary ODNs.

In light of the hybridization properties induced by incorporation of diphosphodiester into ODNs, their base-discriminating properties were evaluated. Satisfactory duplex formation was only observed for matched ODNs based on $T_m$ values. Non-complementary modified chains used as the controls and did not show any sigmoidal melting transition. For example, no melting transition was observed when 12-mer modified ODNs of modified 5'-d(d) (SEQ ID NO: 1) (13) were used with mismatched 12-mer modified or unmodified ODNs of 3'-d(CCCCCCCCCCCC) (SEQ ID NO: 3) (FIG. 7), suggesting that the $T_m$ values were dependent on formation and melting of double stranded structures of complementary modified oligomers in a bimolecular process.

TABLE 3

Thermal denaturation studies ($T_m$ values) of modified (mod.) and unmodified (unmod.) ODNs (1 µM).

| ODN mixtures (12 mers) | | SEQ ID NO | $T_m$ (° C.)[a] | $\Delta T_m$ (° C.)[b] |
|---|---|---|---|---|
| mod. 5'-d(AAAAAAAAAAAA) (13) | + | 1 | 39.7 | +0.3 |
| mod. 3'-d(TTTTTTTTTTTT) (14) | | 2 | | |
| mod. 5'-d(ATATATATATAT) (17) | + | 5 | 35.5 | +1.8 |
| mod. 3'-d(TATATATATATA) (17) | | 6 | | |
| mod. 5'-d(TATATATATATA) (18) | + | 6 | 34.9 | +3.2 |
| mod. 3'-d(ATATATATATAT) (18) | | 5 | | |
| mod. 5'-d(CCCCCCCCCCCC) (15) | + | 3 | 40.2 | ND[c] |
| mod. 3'-d(GGGGGGGGGGGG) (16) | | 4 | | |

TABLE 3-continued

Thermal denaturation studies ($T_m$ values) of modified (mod.) and unmodified (unmod.) ODNs (1 µM).

| ODN mixtures (12 mers) | SEQ ID NO | $T_m$ (° C.)[a] | $\Delta T_m$ (° C.)[b] |
|---|---|---|---|
| mod. 5'-d(AAAAAAAAAAAA) (13) + unmod. 3'-d(TTTTTTTTTTTT) | 1 2 | 39.7 | +0.3 |
| mod. 5'-d(TTTTTTTTTTTT) (14) + unmod. 3'-d(AAAAAAAAAAAA) | 2 1 | 39.5 | +0.1 |
| mod. 5'-d(ATATATATATAT) (17) + unmod. 3'-d(TATATATATATA) | 5 6 | 34.0 | +0.3 |
| mod. 5'-d(TATATATATATA) (18) + unmod. 3'-d(ATATATATATAT) | 6 5 | 33.1 | +1.4 |
| mod. 5'-d(GGGGGGGGGGGG) (16) + unmod. 3'-d(CCCCCCCCCCCC) | 4 3 | 26.4 | ND[c] |
| unmod. 5'-d(AAAAAAAAAAAA) + unmod. 3'-d(TTTTTTTTTTTT) | 1 2 | 39.4 | 0 |
| unmod. 5'-d(ATATATATATAT) + unmod. 3'-d(TATATATATATA) | 5 6 | 33.7 | 0 |
| unmod. 5'-d(TATATATATATA) + unmod. 3'-d(ATATATATATAT) | 6 5 | 31.7 | 0 |

[a]Data measured with 1 µM + 1 'M ODNs at 260 nm in the buffer (pH 7.2) containing $NaH_2PO_4$ (10 mM), $Na_2HPO_4$ (21 mM), NaCl (200 mM), and EDTA (0.20 mM);
[b]$\Delta T_m$ (° C.) values are calculated relative to the relevant unmodified reference (difference in $T_m$ relative to unmodified ODNs);
[c]$\Delta T_m$ was not determined since unmodified $d(G)_{12}$ forms cruciform structures or guanine tetraplex.

These data indicate that modified ODNs are able to form duplexes with their complementary modified or unmodified chains. The diphosphate diester bridges are flexible and probably allow appropriate folding of the backbone for duplex formation with unmodified oligomers. Further structural analysis is required to determine and compare the nature of stacking interactions of modified-modified or modified-unmodified duplexes with those of the unmodified-unmodified duplexes.

Circular Dichroism (CD) Spectropolarimetry

The CD spectra are commonly used for monitoring the secondary structure of nucleic acids in solution and as indicators of the DNA conformation. For subsequent analysis, CD measurements were used in the study of chemically modified ODNs. The method allowed investigating the conformational changes of modified ODNs in the presence of their complementary modified and unmodified chains. It also allowed the comparison between the modified ODNs and unmodified-unmodified analogues.

Comparing Self-Complementary Modified and Unmodified ODNs

Figure 8:
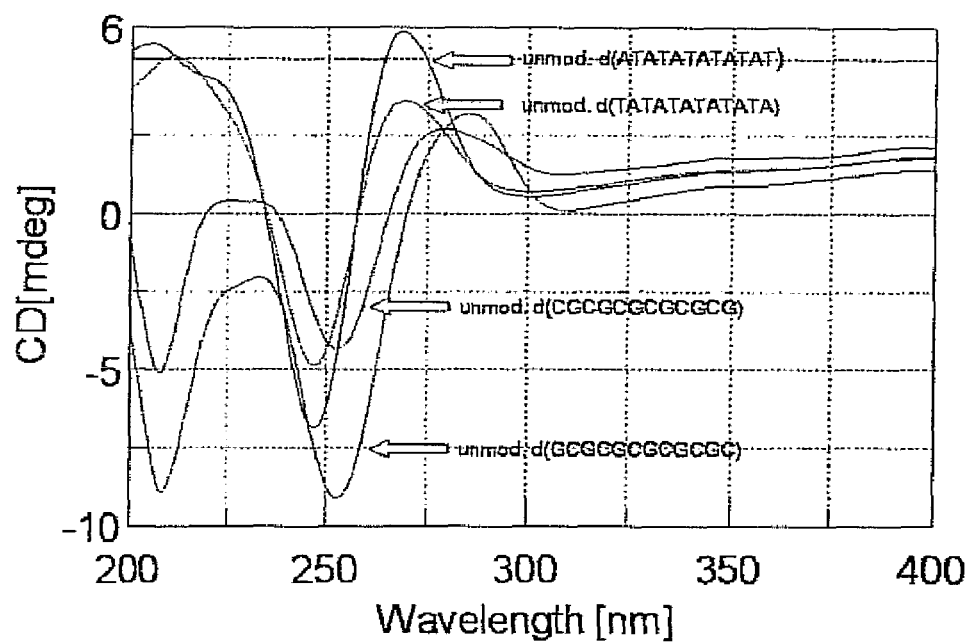
FIG. 8 shows a comparison of the CD spectra for modified and unmodified self-complementary ODNs: (a) modified ODNs; (b) unmodified ODNs; d(ATATATATATAT), d(TATATATATATA), d(CGCGCGCGCGCG) and d(GCGCGCGCGCGC) disclosed as SEQ ID NOS 5-8, respectively.

The CD spectra of the self-complementary strands showed significant difference between the modified and natural sequences as shown in FIG. 8. Modified 12-mer ODNs showed a fairly intense negative band between 217-219 nm and a positive band between 270-283 nm (FIG. 8a). 5'-d (TATATATATATA) (SEQ ID NO: 6) (17) and 5'-d (ATATATATATAT) (SEQ ID NO: 5) (18) exhibited a negative shoulder band at 250 nm. This pattern is close to A form of DNA; however, the positive band in modified ODNs is red shifted compared to that of A-form. Characteristic of the A-form CD is a long-wavelength band centered around 260 nm and a fairly intense band around 210 nm.

In comparison, unmodified self-complementary 12-mer ODNs showed the negative band centered near 247 nm for 5'-d(TATATATATATA) (SEQ ID NO: 6) and 5'-d (ATATATATATAT) (SEQ ID NO: 5), and 253 nm for 5'-d (GCGCGCGCGCGC) (SEQ ID NO: 8) and 5'-d (CGCGCGCGCGCG) (SEQ ID NO: 7), respectively. Unmodified 5'-d(TATATATATATA) (SEQ ID NO: 6) and 5'-d (ATATATATATAT) (SEQ ID NO: 5) showed a positive band centered near 268 nm. In a similar pattern, unmodified 5'-d (GCGCGCGCGCGC) (SEQ ID NO: 8) and 5'-d (CGCGCGCGCGCG) (SEQ ID NO: 7) exhibited a positive band between 277-285 nm (FIG. 8b). In general unmodified self-complementary exhibited a right-handed B form.

The presence of the additional phosphodiester group altered the optical properties of self-complementary modified ODNs, possibly due to changes the conformation of the modified nucleic acids. The presence of additional phosphodiester group in modified oligomers changes the complex to assume a conformation pattern similar to A-form DNA. There are several interrelated factors that determine the conformation of various forms of DNA. The conformation of the sugar ring is related not only to the displacement of the base pairs relative to the helical axis, but also to the separation between the sugars at both ends of each nucleotide. Another important factor contributing to the conformation of nucleic acids is the degree of hydration of phosphate groups and the bases. The phosphate-phosphate separation is 6.6 A° on average in B-DNA. Since in the B form of DNA the phosphate groups are far apart, they are independently hydrated. A-DNA is generally less hydrated than B-DNA. In the A form, water molecules bridge neighboring the free oxygen atoms phosphate groups (phosphate-phosphate separation 5.3 A°) and thus stabilize the A-form at lower water activities. The presence of additional phosphodiester provides an opportunity for water molecules that not only bridge neighboring phosphate groups, but also both phosphate groups in the diphosphodiester linkage. The changes in hydration patterns of phosphate groups and/or a larger sugar-sugar separation appear to modify the conformation of modified ODNs. Phosphate-phosphate electrostatic repulsion is also diminished in water. Further structural analysis may provide insights about additional contributing factors in the conformation of modified ODNs.

Comparing Non-Self-Complementary Modified and Unmodified Single-Stranded ODNs

Figure 9:
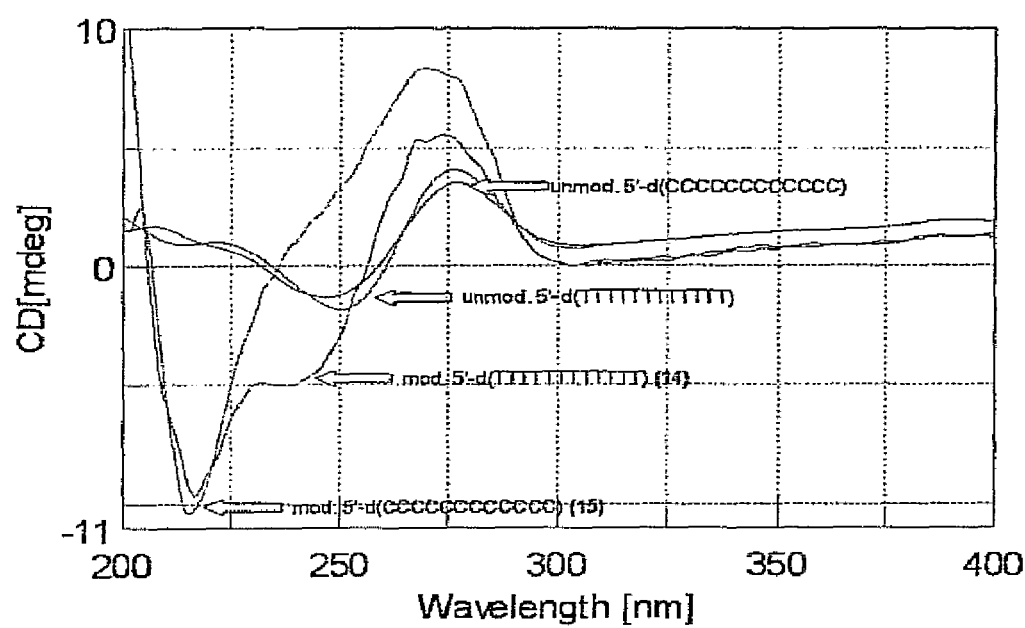
FIG. 9 shows a comparison of the CD spectra for modified and unmodified d(TTTTTTTTTTTT) (SEQ ID NO: 2) and d(CCCCCCCCCCCC) (SEQ ID NO: 3)

FIG. 9 displays the comparison between modified and unmodified non-self complementary single-stranded 5'-d (TTTTTTTTTTTT) (SEQ ID NO: 2) and 5'-d (CCCCCCCCCC) (SEQ ID NO: 3). These modified oligomers showed similar pattern to self-complementary modified oligomers with a fairly intense negative band near 217 nm and a positive band near 270 nm. Unmodified oligomers displayed a B-form DNA with the negative band centered near 250 nm and a positive band centered near 276 nm. In general, negative bands at 217 nm in modified strand were significantly blue-shifted compared to those of unmodified oligomer at 250 nm. These data indicate that modified single-stranded non-self-complementary oligomers adopt conformations similar to A form. Additionally the intensity of negative and positive peaks for single-stranded modified oligomers was higher than those of unmodified ones. As described above several factors, such as different hydration patterns and/or a larger sugar-sugar separation may contribute to the conformational change of modified oligomers.

Comparing Non-Self-Complementary Modified and Unmodified Double-Stranded ODNs

Figure 10:
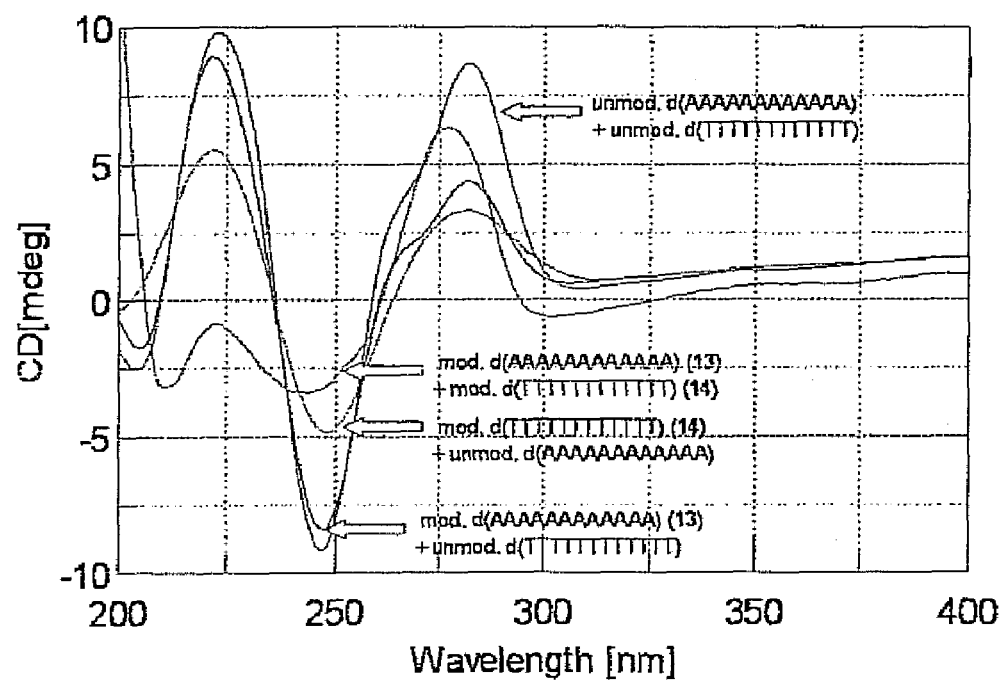
FIG. 10 shows a comparison of CD spectra of modified-modified, modified-unmodified, and unmodified-unmodified ODNs; d(AAAAAAAAAAAA) and d(TTTTTTTTTTTT) disclosed as SEQ ID NOS 1-2, respectively.

FIG. 10 shows the CD spectra of DNA-DNA hybrids with and without diphosphodiesters. Modified double-stranded ODNs consisted of one or two modified strands.

CD spectra showed a pattern similar to right-handed B-DNA for solutions containing the non-self-complementary chains of modified-unmodified ODNs. The spectra of modified 5'-d(TTTTTTTTTTTT) (SEQ ID NO: 2) (14)+unmodified 3'-d(AAAAAAAAAAAA) (SEQ ID NO: 1) and modified 5'-d(AAAAAAAAAAAA) (SEQ ID NO: 1) (13)+unmodified 3'-d(TTTTTTTTTTTT) (SEQ ID NO: 2) in a 1:1 fashion were very similar in terms of pattern with their negative and positive bands centered near 248 and 281 nm, respectively (FIG. 10). A similar pattern was observed for unmodified-unmodified duplexes with their unmodified complementary strands with negative and positive bands centered near 248 and 282 nm, respectively, providing evidence that the structural effect of the diphosphodiester modification was relatively insensitive to which strand contained the modification and confirming the absence of changes in the nucleic acids chromophore. The spectrum of modified 5'-d (AAAAAAAAAAAA) (SEQ ID NO: 1)+unmodified 3'-d (TTTTTTTTTTTT) (SEQ ID NO: 2) hybrid was almost identical to that of the corresponding unmodified-unmodified hybrid. The presence of the additional phosphodiester group in one strand did not alter the optical properties of the nucleic acid in duplex form with an unmodified strand, at least in the usual wavelength range of nucleic acid studies. This demonstrated that the diphosphodiester modification in one strand did not affect the conformation of the hybrids of modified-unmodified duplex. The diphosphodiester group appears to be flexible and can fold to occupy a position similar to that of phosphodiester group. Although the pattern of peaks in terms of wavelengths were similar, bands showed different intensity when comparing $\text{mod.}_1$-$\text{unmod.}_2$ and $\text{mod.}_2$-$\text{unmod.}_1$ duplexes, suggesting more favorable stacking for specific mixtures, such as modified 5'-d(AAAAAAAAAAAA) (SEQ ID NO: 1) (13)+unmodified 3'-d(TTTTTTTTTTTT) (SEQ ID NO: 2).

CD spectra of the duplexes with both strands modified slightly differed from those of the unmodified DNA duplexes and DNA duplexes containing one modified strand. The CD spectra of modified d(AAAAAAAAAAAA) (SEQ ID NO: 1) (13)+modified d(TTTTTTTTTTTT) (SEQ ID NO: 2) (14) (FIG. 10) showed a decreased negative band near 243 nm and a positive band near 277, showing that a diphosphodiester modification on either strand did have an effect on the conformation of the duplex. The spectral shift toward the shorter wavelengths is evident for modified-modified duplexes with negative band near 243 nm when compared to those of modified-unmodified and unmodified-unmodified duplexes between 247-248 nm.

A difference between the CD spectra of the modified-modified ODNs and those of its natural analogues (unmodified-unmodified) and modified-unmodified oligomers may be due to significant conformational change when both strands are modified. This drastic conformational effect may be due to an increase in the flexibility of diphosphodiester-modified DNA strands and different stacking. CD spectra for modified ODNs containing both modified strands generally showed (FIG. 10) decreased negative band intensities throughout the spectral region studied. This was interpreted as reflecting the fact that the bases of the modified-modified ODNs were less stacked. Despite these differences, these oligomers adopted a pattern similar to right-handed B-DNA duplex.

Figure 11:
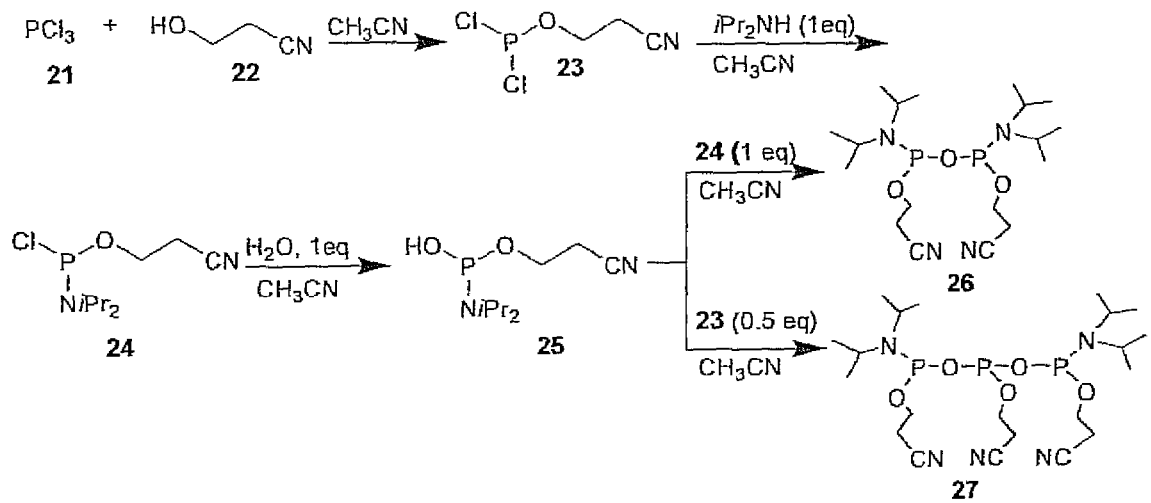
FIG. 11 shows synthesis of diphosphitylating (26) and triphosphitylating reagents (27)

2. Synthesis and Use of Diphosphitylating, Triphosphitylating and β-Triphosphitylating Reagents Chemistry FIG. 11 illustrates the synthesis of diphosphitylating and triphosphitylating reagents (6 and 7). Phosphorus trichloride (21, 20 mmol) was reacted with 3-hydroxypropionitrile (22, 1 eq) to yield 2-cyanoethylphosphorodichloriditite (23). The subsequent reaction of 23 with diisopropylamine (20 mmol, 1 eq) afforded 2-cyanoethyl diisopropylphosphoramidochloridite (24). Addition of water (1 eq) gave the intermediate 25 that was reacted with 24 (1 eq) or 23 (0.5 eq) to yield the diphosphitylating (26, 97%) and triphosphitylating (27, 94%) reagents, respectively. The chemical structures of 26 and 27 were determined by nuclear magnetic resonance spectra ($^1$H NMR, $^{13}$C NMR, $^{31}$P NMR) and high-resolution time of flight electrospray mass spectrometry. Stability studies using spectroscopic methods showed that the compounds remained stable even after two weeks storage at −20° C.

Figure 12:
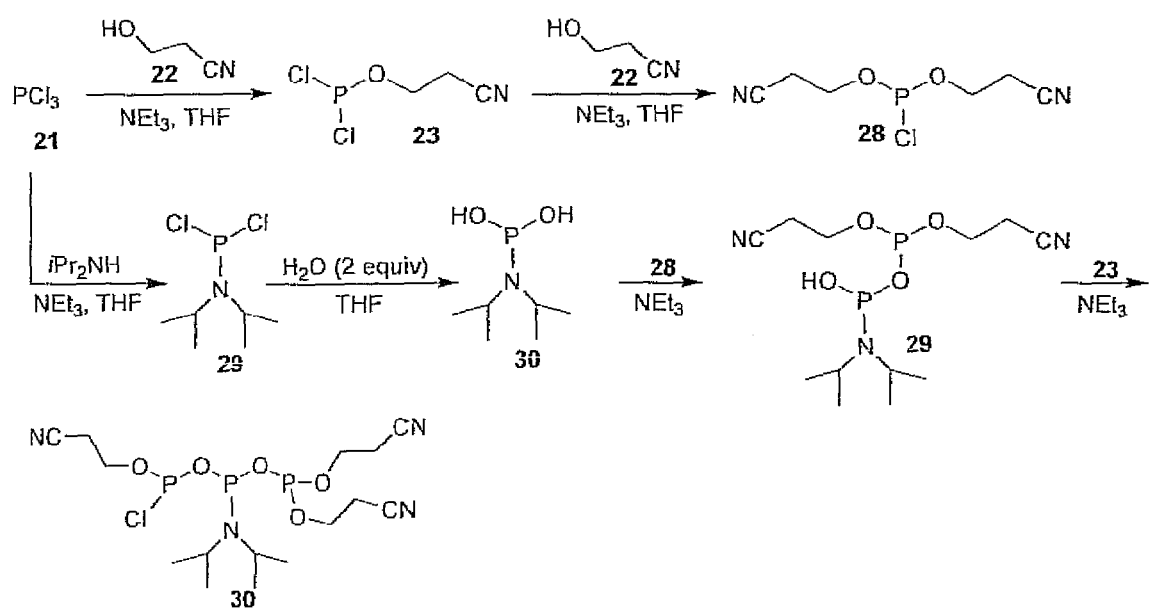
FIG. 12 shows synthesis of β-triphosphitylating reagent (30)

FIG. 12 illustrates the synthesis of the β-triphosphitylating reagent (30). Phosphorus trichloride (21, 10 mmol) was reacted with 3-hydroxypropionitrile (1 or 2 equiv) in the presence of triethylamine (1 or 2 equiv) to yield 2-cyanoethyl phosphorodichloriditite (23) or bis(2-cyanoethyl) phosphorochloriditite (28), respectively. The parallel reaction of 21 (10 mmol) with diisopropylamine (10 mmol, 1 equiv) afforded diisopropylphosphoramidodichloriditite (29). The addition of water (2 equiv) gave the compound 30 that was reacted with 28 (1 equiv) in the presence of triethylamine (1 equiv) to afford 29. The reaction of equimolar amounts of 23 and 29 produced β-triphosphitylating reagent (30) in 91% overall yield. The chemical structure of 30 was determined by nuclear magnetic resonance spectra ($^1$H NMR, $^{13}$C NMR, and $^{31}$P NMR) and high-resolution time-of-flight electrospray mass spectrometry. Stability studies using these spectroscopic methods showed that the compound remained stable even after 2 months storage at −20° C. and 10 days at room temperature in DMSO solution.

Figure 13:
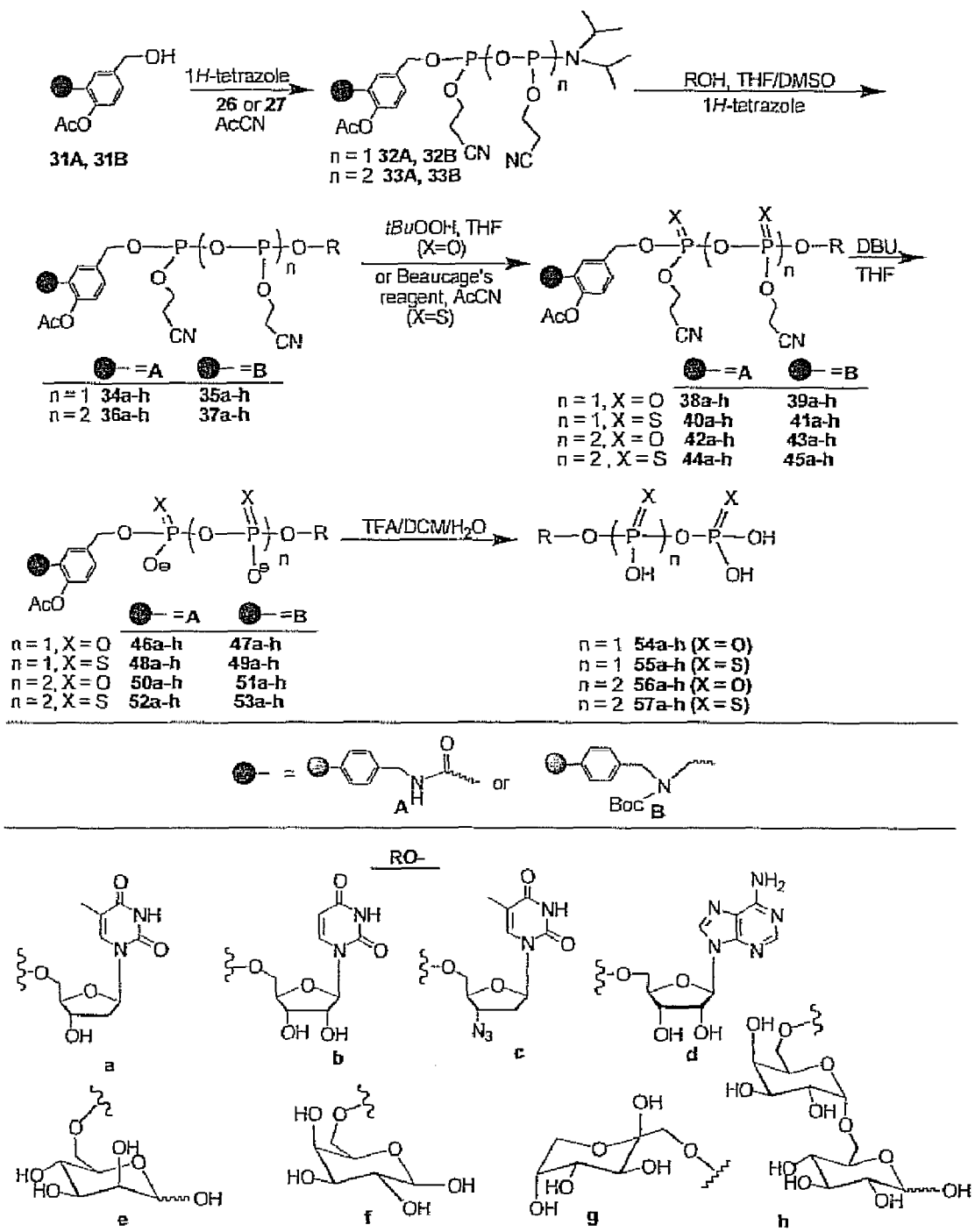
FIG. 13 shows selective synthesis of nucleoside and carbohydrate diphosphates, dithiodiphosphates, triphosphates, and trithiotriphosphates on solid-phase using polymer-bound linkers 31A and 31B.

Two polymer-bound-linkers containing the p-acetoxybenzyl alcohol were selected and synthesized from aminomethyl polystyrene resin in multiple-step reactions. The polymer-bound linkers included aminomethyl polystyrene resin linked through amide bond with p-acetoxybenzyl alcohol (31A) and aminomethyl polystyrene resin linked through reduced amide bond with p-acetoxybenzyl alcohol (31B) (FIG. 13).

Two classes of aminomethyl polystyrene resin-bound linkers of p-acetoxybenzyl alcohol, 31A (3.05 g, 0.87 mmol/g) and 31B (3.75 g, 0.72 mmol/g), were subjected to reactions with the diphosphitylating reagent (26, 10 mmol) in the presence of 1H-tetrazole to produce the corresponding polymer-bound diphosphitylating reagents (32A and 32B). Several unprotected nucleosides (e.g., thymidine (a), uridine (b), 3'-azido-3'-deoxythymidine (c), adenosine (d)) and carbohydrates (e.g., α,β-D-mannose (e), β-D-galactopyranose (f), β-D-fructopyranose (g), melibiose (h)) (1.28 mmol) were reacted with the polymer-bound reagents (32A and 32B) in the presence of 1H-tetrazole to yield 34a-h and 35a-h, respectively. Oxidation with tert-butyl hydroperoxide or sulfurization with Beaucage's reagent (3H-1,2-benzotrithiole-3-one 1,1-dioxide), followed by removal of the cyanoethoxy group with DBU, afforded the corresponding polymer-bound diphosphodiesters, 46a-h and 47a-h, or diphosphodithioesters, 48a-h and 49a-h. The cleavage of polymer-bound compounds was carried out under acidic conditions (TFA). The crude products had a purity of 69-91% and were purified by using small $C_{18}$ Sep-Pak cartridges and appropriate solvents to afford nucleosides and carbohydrates diphosphates (54a-h) and diphosphodithioates (55a-h) (FIG. 13) in 51-84% overall yield (calculated from 32A and 32B in four-step reaction sequence) (Table 4). Only one type of monosubstituted compounds were produced with high selectivity as a result of this sequence.

The synthetic approach for the selective solid-phase synthesis of triphosphates and triphosphotrithioates was similar to the diphosphorylation and dithiophosphorylation protocols (FIG. 13), respectively, except for the use of a triphosphitylating reagent (27), instead of a diphosphitylating reagent (26). The reaction of polymer-bound linkers 31A and 31B with the triphosphitylating reagent (27) in the presence of 1H-tetrazole afforded the polymer-bound triphosphitylating reagents 33A and 33B. A number of unprotected nucleosides (e.g., a-d) and carbohydrates (e.g., e-h) were reacted with the polymer-bound reagents. The resulting polymer-bound compounds, 36a-h and 37a-h, underwent oxidation and deprotection reactions to afford the polymer-bound triphosphodiesters, 50a-h and 51a-h, or triphosphotrithiodiesters, 52a-h and 53a-h. Cleavage from the resins under acidic conditions and purification of crude products (64-91% purity) by using small $C_{18}$ Sep-Pak cartridges afforded the nucleoside and carbohydrate triphosphates (56a-h) and triphosphotrithioates (57a-h) with high selectivity in 42-79% overall yield (calculated from 33A and 33B in four steps) (Table 4).

nucleosides (e.g., adenosine (a), uridine (b), 3'-azido-3'-deoxythymidine (c), thymidine (d), inosine (e), and cytidine (f)) were reacted with polymer-bound reagent 58 in the presence of 1H-tetrazole to yield 59a-f. Oxidation with t-butyl hydroperoxide followed by removal of the cyanoethoxy group with DBU, afforded the corresponding polymer-bound nucleoside 5'-O-β-triphosphotriesters (61a-f). The cleavage of polymer-bound compounds was carried out under acidic conditions (TFA). The intramolecular cleavage mechanism of final products from (61a-f) is shown in Scheme 2. The linker-trapped resin (64) was separated from the final products by filtration. The crude products had a purity of 87-96% (Table 1) and were purified by using small $C_{18}$ Sep-Pak cartridges and appropriate solvents to afford nucleoside 5'-O-β-triphosphates (63a-f) in 65-87% overall yield (calculated from 58 in the four-step reaction sequence) (Table 5). Only one type of monosubstituted compound was produced with high selectivity as a result of this sequence. The chemical structures of the final products (63a-f) were determined by nuclear magnetic resonance spectra ($^1$H NMR, $^{13}$C NMR, and $^{31}$P NMR), high-resolution time-of-flight electrospray mass spectrometry, and quantitative phosphorus analysis. Stability studies using $^1$H NMR showed that all final compounds remained stable after 8 months storage in DMSO at −20° C.

TABLE 4

Overall isolated yields and purity of crude products for carbohydrate and nucleoside diphosphates (54a-h), diphosphodithioates (55a-h), triphosphates (56a-h), and triphosphotrithioates (57a-h).

| No. | Overall yield (%) calculated from 32A or 33A | Overall yield (%) calculated from 32B or 33B | Purity of crude products (%) using 31A | Purity of crude products (%) using 31B |
|---|---|---|---|---|
| 54a | 77 | 80 | 81 | 91 |
| 54b | 75 | 77 | 83 | 89 |
| 54c | 84 | 80 | 90 | 87 |
| 54d | 68 | 64 | 82 | 83 |
| 54e | 60 | 68 | 77 | 87 |
| 54f | 66 | 60 | 89 | 79 |
| 54g | 61 | 51 | 86 | 84 |
| 54h | 51 | 54 | 69 | 72 |
| 55a | 69 | 74 | 83 | 91 |
| 55b | 72 | 77 | 88 | 85 |
| 55c | 78 | 82 | 91 | 89 |
| 55d | 63 | 72 | 75 | 87 |
| 55e | 70 | 74 | 80 | 86 |
| 55f | 72 | 61 | 87 | 76 |
| 55g | 53 | 55 | 75 | 81 |
| 55h | 57 | 57 | 74 | 79 |
| 56a | 74 | 76 | 80 | 90 |
| 56b | 71 | 73 | 78 | 87 |
| 56c | 79 | 77 | 91 | 91 |
| 56d | 63 | 60 | 79 | 79 |
| 56e | 64 | 64 | 81 | 83 |
| 56f | 58 | 51 | 76 | 72 |
| 56g | 55 | 47 | 71 | 80 |
| 56h | 43 | 42 | 64 | 67 |
| 57a | 63 | 77 | 75 | 89 |
| 57b | 69 | 70 | 86 | 86 |
| 57c | 81 | 75 | 90 | 90 |
| 57d | 67 | 59 | 77 | 76 |
| 57e | 73 | 71 | 79 | 82 |
| 57f | 65 | 54 | 76 | 69 |
| 57g | 45 | 46 | 67 | 77 |
| 57h | 47 | 50 | 71 | 67 |

TABLE 5

Overall Isolated Yields and Purity of Crude Products for Nucleoside 5'-O-β-Triphosphates (63a-f).

| no. | Overall yield (%) calcd from 58 | Purity of crude products |
|---|---|---|
| 63a | 79 | 90 |
| 63b | 65 | 88 |
| 63c | 87 | 96 |
| 63d | 78 | 89 |
| 63e | 63 | 87 |
| 63f | 81 | 92 |

In conclusion, nucleoside 5'-O-β-triphosphates were synthesized by using a polymer-bound β-triphosphitylating reagent. Only one type of monosubstituted product was formed using the solid-phase strategy, probably due to the reaction of the sterically rigid polymer-bound reagent with the most exposed and reactive hydroxyl groups. The products were easily isolated from the polymer-bound trapped linker. These compounds can have diverse applications in nucleic acid research and studying and/or inhibiting enzymes involved in the synthesis of nucleoside triphosphates.

Figure 14:
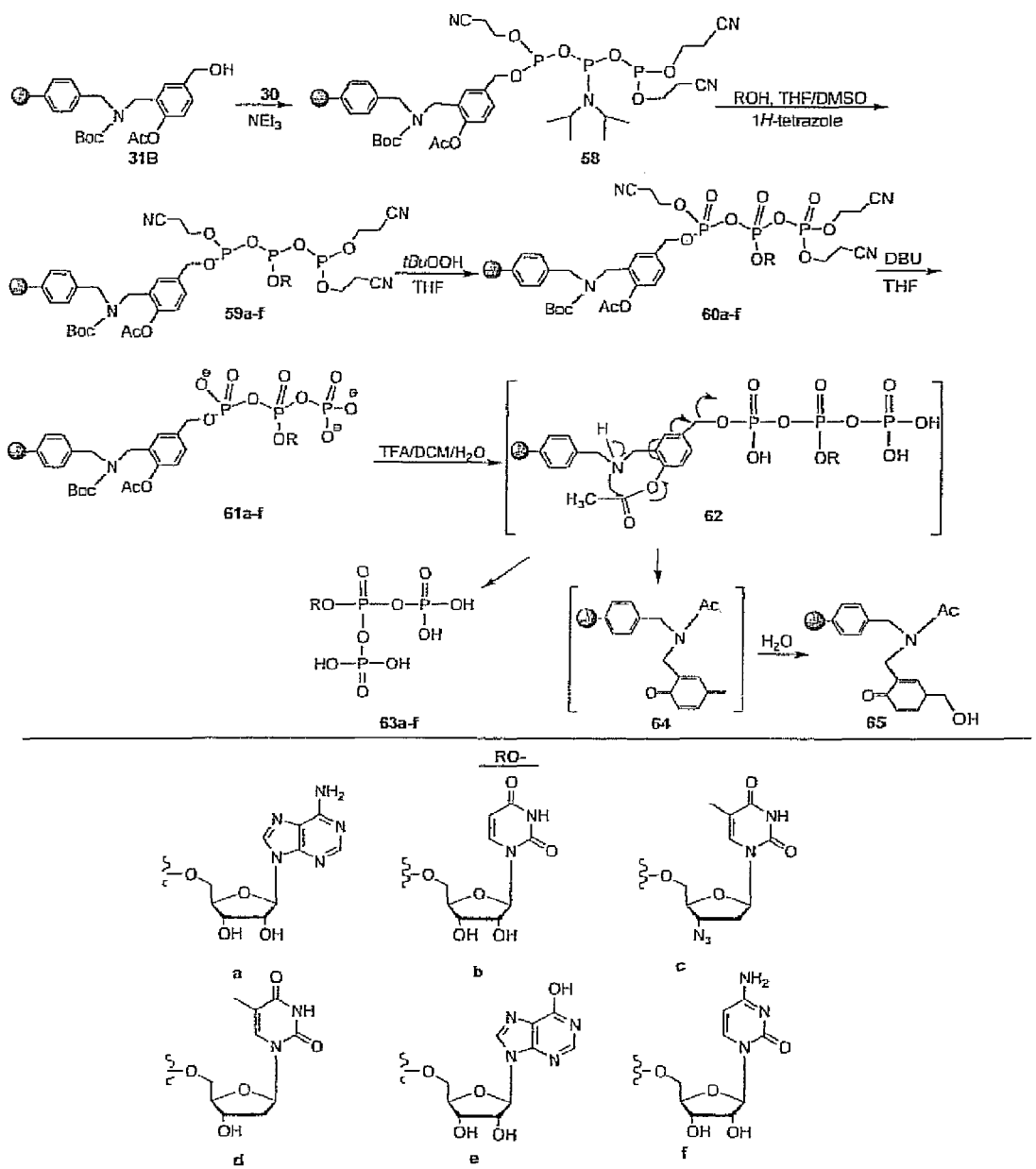
FIG. 14 shows synthesis of polymer-sound β-phosphitylating reagent (58) and nucleosides 5'-O-β-triphosphates (63a-f) using polymer-bound linker 31B.
Figure 15:
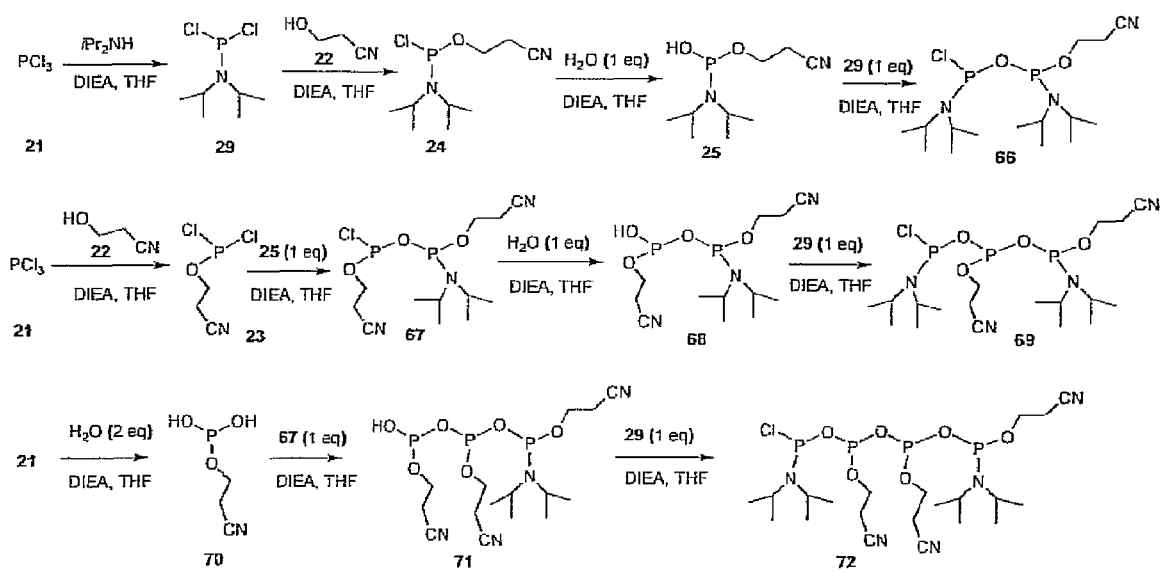
FIG. 15 shows synthesis of diphosphitylating, triphosphitylating, and tetraphosphitylating reagents (66, 69, 72)

FIG. 15 illustrates the synthesis of bifunctional diphosphitylating, triphosphitylating, and tetraphosphitylating reagents (66, 69, 72). For the preparation of 66, phosphorus trichloride (21, 875 μL, 10 mmol) and diisopropylethylamine (1,747 μL, 10 mmol) were added to anhydrous THF. Diisopropylamine (1,400 μL, 10 mmol) was added dropwise in 10 min to the solution mixture and the mixture was stirred for 45 min at 0° C. to yield diisopropylphosphoramidodichloridite (29). Then 3-hydroxypropionitrile (22, 683 μL, 10 mmol) and diisopropylethylamine (1,747 μL, 10 mmol) were added dropwise to the solution of 29 in anhydrous THF during 10 min period. The stirring was continued for 25 min at 0° C. to afford 2-cyanoethyl diisopropylphosphoramidochloridite (24). Water (180 μL, 10 mmol) and diisopropylethylamine (1,747 μL, 10 mmol) were added dropwise in 10 min period to the solution. The mixture was stirred for 10 min at 0° C. to yield 2-cyanoethyl diisopropylamine hydroxyphosphite (25). Then 29 (1 eq, 10 mmol) that was prepared at the same time in a separate reaction vessel, was added dropwise in 10 min FIG. 14 shows the synthesis of nucleoside 5'-O-β-triphosphates (63a-f). Aminomethyl polystyrene resin-bound linker (31B, 3.75 g, 0.72 mmol/g) was subjected to reaction with the β-triphosphitylating reagent (30, 10 mmol) in the presence of triethylamine (10 mmol) to produce the corresponding polymer-bound β-triphosphitylating reagent (58). Unprotected period to the solution containing 25. The mixture was stirred for 25 min at 0° C. to yield diisopropylphosphoramidochloridite-O-2-cyanoethyl diisopropylphosphoramidite 66 (bifunctional diphosphitylating reagent). The reaction mixture containing diphosphitylating reagent 66 was immediately used in coupling reactions with polymer-bound p-acetoxybenzyl alcohol 78. Further stability studies on 66 using mass spectrometry methods showed that the compound remained stable after 2 months storage at −20° C.

For the preparation of 69, phosphorus trichloride (21, 875 μL, 10 mmol) and diisopropylethylamine (1,747 μL, 10 mmol) were added to anhydrous THF. 3-Hydroxypropionitrile (683 μL, 10 mmol) was added dropwise in 10 min to the solution and the mixture was stirred for 25 min at 0° C. to yield 2-cyanoethylphosphorodichloridite (23). Then 25 (1 eq, 10 mmol) that was prepared at the same time in a separate reaction vessel, was added dropwise in 10 min period to the solution containing 23. The mixture was stirred for 15 min at 0° C. to yield 2-cyanoethyl phosphorochloridite-O-2-cyanoethyl diisopropylphosphoramidite (67). Water (180 μL, 10 mmol) and diisopropylethylamine (1,747 μL, 10 mmol) were added dropwise in 10 min period to the solution containing 67. The mixture was stirred for 10 min at 0° C. to yield 2-cyanoethyl hydroxyphosphite-O-2-cyanoethyl diisopropylphosphoramidite (68). Then 29 (1 eq, 10 mmol) that was prepared at the same time in a separate reaction vessel, was added dropwise in 10 min period to the solution containing 68. The mixture was stirred for 35 min at 0° C. to yield bifunctional triphosphitylating reagents 69. The reaction mixture containing triphosphitylating reagent 69 was immediately used in coupling reactions with polymer-bound p-acetoxybenzyl alcohol 78. Further stability studies on 69 using mass spectrometry methods showed that the compound remained stable after 2 months storage at −20° C.

For the preparation of 72, compound 67 (10 mmol) was prepared as described above. Water (360 μL, 20 mmol) and diisopropylethylamine (3,494 μL, 20 mmol) were added dropwise in 10 min period to the solution of 21 and the mixture was stirred for 10 min at 0° C. to yield 2-cyanoethyl dihydroxyphosphite (70). Compound 67 (10 mmol) that was prepared at the same time in a separate reaction vessel, was added dropwise in 10 min period to the solution containing 70. The mixture was stirred for 35 min at 0° C. to yield 71. Then 29 (1 eq, 10 mmol) that was prepared at the same time in a separate reaction vessel, was added dropwise in 10 min period to the solution containing 71. The mixture was stirred for 35 min at 0° C. to yield bifunctional tetraphosphitylating reagent (72). The reaction mixture containing tetraphosphitylating reagent 72 was immediately used in coupling reactions with polymer-bound p-acetoxybenzyl alcohol 78. Further stability studies on 72 using mass spectrometry methods showed that the compound remained stable after 2 months storage at −20° C.

Figure 16:
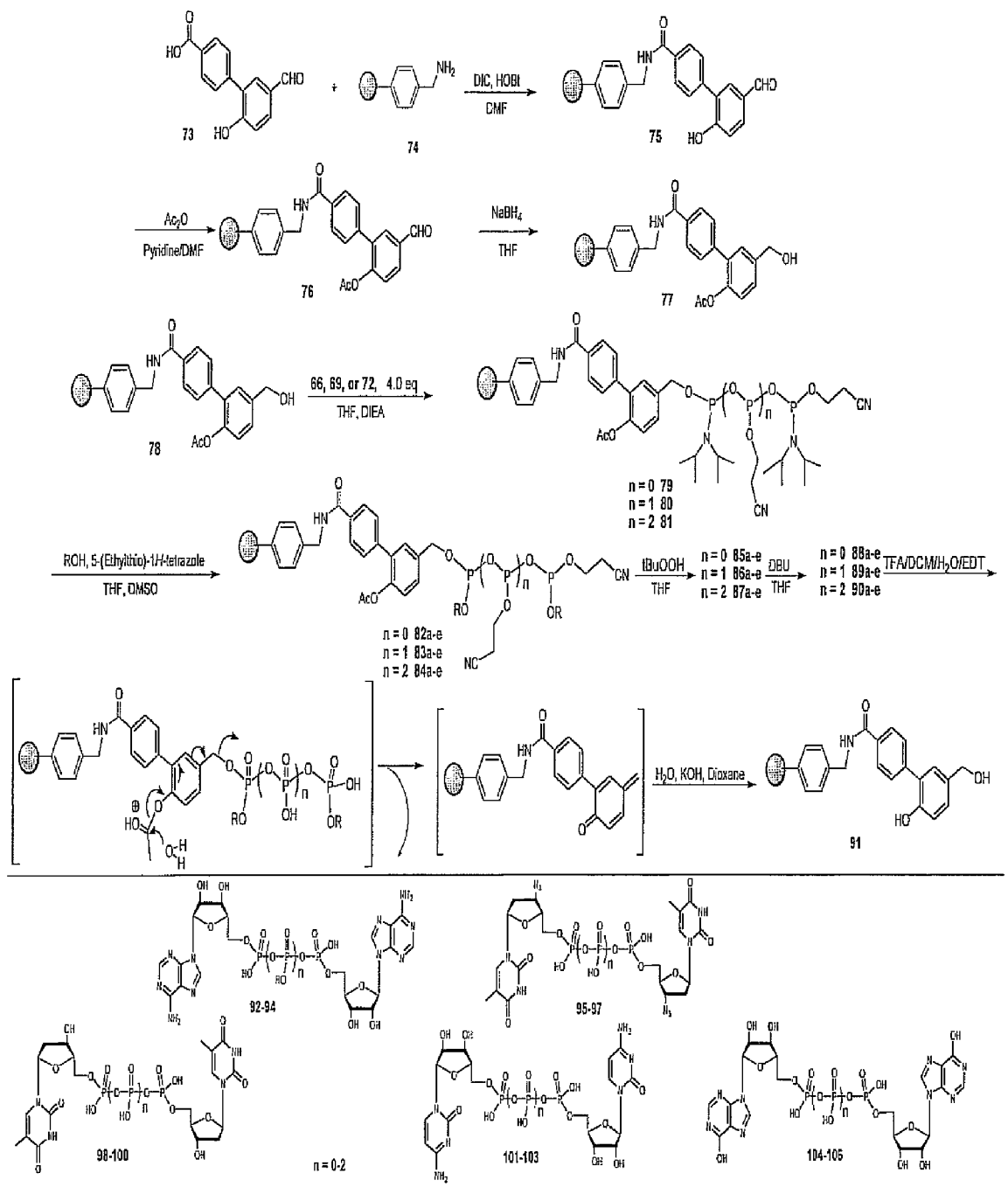
FIG. 16 shows synthesis of dinucleosides diphosphodiesters, triphosphodiesters, and tetraphosphodiesters 92-106.

FIG. 16 shows the synthesis of polymer-bound bifunctional diphosphitylating (79), triphosphitylating (80) and tetraphosphitylating (81) reagents, and dinucleoside diphosphodiesters, triphosphodiesters and tetraphosphodiesters (92-106). The prepared reaction mixture containing 66, 69 or 72 in anhydrous THF (~10 mmol) was added to a swelled solution of polymer-bound p-acetoxybenzyl alcohol 78 (3.63 g, 0.69 mmol/g, each) and diisopropylethylamine (1,747 μL, 10 mmol). The mixture was shaken for 24 h at room temperature. The resins were collected by filtration, washed with THF (3×35 mL), DCM (3×35 mL), and MeOH (3×35 mL), respectively, and were dried overnight under vacuum to give 79, 80, or 81, respectively. Unprotected nucleosides (eg., adenosine (a), AZT (b), thymidine (c), cytidine (d), inosine (e); 4.0 mmol) and 5-(ethylthio)-1H-tetrazole (260 mg, 2.0 mmol) were added to 79 (890 mg, 0.53 mmol/g), 80 (946 mg, 0.50 mmol/g), and 81 (994 mg, 0.46 mmol/g) in anhydrous THF (2 mL) and DMSO (3 mL) in case of thymidine, 3'-azido-3'-deoxythymidine, and inosine or in anhydrous DMSO (5 mL) in case of adenosine and cytidine. The mixtures were shaken for 48 h at room temperature. The resins were collected by filtration and washed with DMSO (3×30 mL), THF (3×30 mL), and MeOH (3×30 mL), respectively, and dried under vacuum to give 82a-e (999-1013 mg), 83a-e (1055-1068 mg), and 84a-e (1102-1112 mg).

tert-Butyl hydroperoxide in decane (5-6 M) (1.0 mL, 4.0 mmol), (1.2 mL, 6.0 mmol), (2.0 mL, 8.0 mmol) was added, respectively, to the swelled resins 82a-e (999-1013 mg), 83a-e (1055-1068 mg), and 84a-e (1102-1112 mg) in THF (5 mL). After 2.5 h shaking at room temperature, the resins were collected by filtration and washed with THF (3×25 mL) and MeOH (3×25 mL), respectively, and were dried overnight at room temperature under vacuum to give 85a-e (1030-1041 mg), 86a-e (1102-1114 mg), and 87a-e (1163-1175 mg). DBU (299 μL, 2.0 mmol), (598 μL, 4.0 mmol), and (897 μL, 6.0 mmol) was added, respectively, to the swelled resins 85a-e (1030-1041 mg), 86a-e (1102-1114 mg), and 87a-e (1163-1175 mg) in THF (5 mL). After 48 h shaking of the mixture at room temperature, the resins were collected by filtration and washed with THF (3×35 mL) and MeOH (3×35 mL), respectively, and were dried overnight at room temperature under vacuum to give 88a-e (1006-1017 mg), 89a-e (1055-1067 mg), and 90a-e (1091-1105 mg).

To the swelled resins 88a-e (1006-1017 mg), 89a-e (1055-1067 mg), and 90a-e (1091-1105 mg) in anhydrous DCM (2 mL) was added DCM/TFA/water/EDT (72.5:23:2.5:2 v/v/v/v, 5 mL). After 30 min shaking of the mixtures at room temperature, the resins were collected by filtration and washed with DCM (10 mL), THF (10 mL), and MeOH (10 mL), respectively. The solvents of filtrate solutions were evaporated at −20° C. The residues were mixed with Amberlite AG-50W-X8 (100-200 mesh, hydrogen form, 1.0 g, 1.7 meq/g) in water:dioxane (75:25 v/v, 5 mL) for 25 min. After filtration, the solvents were removed using lyophilization and the crude products were purified on $C_{18}$ Sep-Pak using appropriate solvents. The solvents were evaporated and the residues were dried under vacuum at −20° C. to yield 92-106. The purity and total isolated yields for 92-106 are shown in Table 6. The compounds were characterized by $^1$H NMR, $^{13}$C NMR, $^{31}$P NMR, high resolution mass spectrometer (ESI-TOF), and quantitative phosphorus elemental analysis.

TABLE 6

Overall isolated yields and purity of crude products for dinucleoside diphosphodiesters, triphosphodiesters, and tetraphosphodiesters (92-106).

|  | No. | Overall yield (%) calculated from 79-81 | Purity of crude products |
|---|---|---|---|
| Diphosphodiester | 92 | 65 | 87 |
| Diphosphodiester | 95 | 61 | 81 |
| Diphosphodiester | 98 | 67 | 79 |
| Diphosphodiester | 101 | 59 | 78 |
| Diphosphodiester | 104 | 70 | 90 |
| Triphosphodiester | 93 | 62 | 75 |
| Triphosphodiester | 96 | 63 | 80 |
| Triphosphodiester | 99 | 66 | 85 |
| Triphosphodiester | 102 | 67 | 86 |
| Triphosphodiester | 105 | 72 | 93 |
| Tetraphosphodiester | 94 | 67 | 91 |
| Tetraphosphodiester | 97 | 62 | 85 |

TABLE 6-continued

Overall isolated yields and purity of crude products for dinucleoside diphosphodiesters, triphosphodiesters, and tetraphosphodiesters (92-106).

|  | No. | Overall yield (%) calculated from 79-81 | Purity of crude products |
|---|---|---|---|
| Tetraphosphodiester | 100 | 70 | 91 |
| Tetraphosphodiester | 103 | 68 | 88 |
| Tetraphosphodiester | 106 | 76 | 95 |

In conclusion, dinucleoside diphosphodiesters, triphosphodiesters and tetraphosphodiesters were synthesized by using polymer-bound diphosphitylating, triphosphitylating, and tetraphosphitylating reagents. Only one type of product was formed using the solid-phase strategy, probably due to the reaction of the sterically rigid polymer-bound reagent with the most exposed and reactive hydroxyl groups. The products were easily isolated from the polymer-bound trapped linker. These compounds can have diverse applications in nucleic acid research and studying and/or inhibiting enzymes involved in the synthesis of nucleosides diphosphodiesters, triphosphodiesters, and tetraphosphodiesters.

Experimental

General Information

All reactions were carried out in Bio-Rad polypropylene columns by shaking and mixing using a Glass-Col small tube rotator in dry conditions at room temperature unless otherwise stated. Real-time monitoring of loading of compounds on resin beads was carried out with a Thermo-Nicolet 550 FT-IR spectrophotometer coupled with a Nic-Plan microscope using OMNIC software. The chemical structures of final products were characterized by nuclear magnetic resonance spectrometry determined on a Bruker NMR spectrometer (400 MHz). $^{13}$C NMR spectra are fully decoupled. $^{31}$P NMR spectra for ODNs up to 5 mers are decoupled. The chemical structures of final products containing up to 5 bases were confirmed by a high-resolution PE Biosystems Mariner API time-of-flight electrospray mass spectrometer and quantitative phosphorus analysis. The chemical structures of 12-mer ODNs were confirmed by a MALDI-TOF mass spectrometer and quantitative phosphorus analysis. The substitution of the resins for each step was estimated from the weight gain of the resin. Total isolated yields for final products were calculated based on the loading of aminomethyl polystyrene resin-bound bis(2-cyanoethyl diisopropylphosphoramidite (1, 0.74 mmol/g) and the amount of diphosphorylated products. Bis(2-cyanoethyl diisopropylphosphoramidite), [(i-Pr)$_2$NPOCH$_2$CH$_2$CN]$_2$O, and polymer-bound diphosphitylating reagent (1) were prepared according to the procedure explained above for the synthesis of 32A. Unmodified ODNs were purchased from Integrated DNA Technologies, Inc. and were desalted and purified.

Reverse Phase HPLC Purification of Modified ODNs Containing 12 Bases

Modified oligomers were purified (>99%) on a Phenomenex® Prodigy 10 µm ODS reversed-phase column (2.1×25 cm) with Hitachi HPLC system using a gradient system of H$_2$O (1 mM ammonium acetate) and acetonitrile. The purification was performed with a gradient of 0-100% CH$_3$CN over 50-60 min and a flow rate of 2.4 mL/min. The product fractions were collected, concentrated under vacuum, and dissolved in filtered (0.22 µm) water. The pH was adjusted with 80% acetic acid to approximately pH 7.2. The solutions were freeze dried to afford pure 12-mer modified ODNs.

$T_m$ Measurements

Melting points ($T_m$ values) for the ODN duplexes were determined on a Beckman Coulter DU 800 UV/Visible Spectrophotometer equipped with a Peltier Temperature Controller. The absorbance at 260 nm was measured, while the temperature of the sample was increased or decreased at a rate of 1.0° C./min. The percent hyperchromicity at 260 nm was plotted as a function of temperature. All modified and control oligomers were separately mixed with target oligomers in a 350 µL quartz cuvette of 1 cm optical path length, and the $T_m$ was determined as the maximum of the first derivative of the melting curve ($A_{260}$ against temperature). Each $T_m$ is the average of three separate determinations (exp. error: ±0.5° C.). All duplexes were formed in a 1:1 ratio of the test oligomer with the complementary stand. Concentrations were 1 µM in each strand. The buffer (pH 7.2) was NaH$_2$PO$_4$ (10 mM), Na$_2$HPO$_4$ (21 mM), NaCl (200 mM), and EDTA (0.20 mM). Prior to analysis, the strands were allowed to anneal by heating briefly (8 min) at 85° C., followed by equilibrating to room temperature, chilling on ice for 25 min, and then re-equilibrating to room temperature (25° C.).

Circular Dichroism Spectra

CD spectra were recorded using a JASCO J-810 spectropolarimeter. All CD experiments were performed at 5° C. in 1 mm path-length cuvettes with a buffer adjusted to pH 7.2 containing 200 mM NaCl, 10 mM NaH$_2$PO$_4$, 21 mM Na$_2$HPO$_4$, and 0.20 mM EDTA. The concentrations were 10 µM for each strand in a total volume of 350 µL. Prior to CD analysis, hybridization of the duplexes was performed as described for the melting curve analysis.

MALDI-TOF Mass Spectroscopy

MALDI-TOF analysis was performed on a Ciphergen Workstation. Modified ODNs were purified by reverse phase HPLC utilizing volatile salts, concentrated to dryness, and dissolved in acetonitrile/water (1:1) to a final concentration of 200 µM. The matrix contained 2,4,6-trihydroxyacetophenone monohydrate (THAP) and was prepared by adding of THAP (0.2 mmol, 45 mg) and ammonium citrate (8.2 µmol, 2 mg) to acetonitrile/water (500 µL, 1:1), which forms a supersaturated solution (a cloudy suspension). The THAP matrix suspension (1 µL) was spotted on a gold plate. The oligomer solution (1 µL) was pipetted onto the same location. The mixture was carefully dried. The plate was inserted into the MALDI-TOF Workstation. All measurements were performed using a positive detection mode.

Preparation of Oligonucleotide Containing Phosphodiester Internucleotide Linkages Preparation of Polymer-Bound Diphosphite Triesters (5a-h, n=0-4, 11)

Nucleosides (a-d) (1.28 mmol, 4 eq) and 1H-tetrazole (45 mg, 0.64 mmol, 2 eq) were added to polymer-bound phosphitylating reagent (1, 433 mg, 0.74 mmol/g, 1 eq) in anhydrous THF (1 mL) and DMSO (4 mL). The mixture was shaken for 24 h at room temperature. The resin was collected by filtration and washed with DMSO (3×20 mL), THF (2×15 mL), and MeOH (3×20 mL), respectively, and dried under vacuum to give 2a-d. Stepwise diphosphitylation of 3'-hydroxyl group in 2a-d with diphosphitylating reagent (4 eq) was carried out in anhydrous THF (15 mL) in the presence of 1H-tetrazole (45 mg, 0.64 mmol, 2 eq). The mixture was shaken for 24 h at room temperature. The resin was collected by filtration and washed with THF (2×15 mL), and MeOH (3×20 mL), respectively, and dried under vacuum to afford 3a-d. Polymer-bound 3'-phosphitylating reagent was subjected with reactions with nucleosides (a-d) in anhydrous THF (1 mL) and DMSO (4 mL) in the presence of 1H-tetrazole (45 mg, 0.64 mmol, 2 eq). The mixture was shaken for 24 h at room temperature to yield polymer-bound oligonucleotide diphosphite ditriester derivatives of 5a-h (n=0-4, 11). IR (cm$^{-1}$): 5a (n=0): 3378 (OH), 2258 (CN), 1772 (C=O ester), 1644 (C=O, amide), 1030 (P—O—C); 5b (n=0): 3344 (OH), 2258 (CN), 1738 (C=O ester), 1644 (C=O, amide), 1026 (P—O—C); 5c (n=0): 3353 (OH), 2260 (CN), 1703 (C=O ester), 1646 (C=O, amide), 1025 (P—O—C); 5d (n=0): 3349 (OH), 2263 (CN), 1715 (C=O ester), 1650 (C=O, amide), 1029 (P—O—C); 5a (n=1): 3328 (OH), 2261 (CN), 1777 (C=O ester), 1647 (C=O, amide), 1029 (P—O—C); 5b (n=1): 3322 (OH), 2258 (CN), 1735 (C=O ester), 1649 (C=O, amide), 1033 (P—O—C); 5c (n=1): 3341 (OH), 2266 (CN), 1734 (C=O ester), 1648 (C=O, amide), 1026 (P—O—C); 5d (n=1): 3329 (OH), 2255 (CN), 1734 (C=O ester), 1641 (C=O, amide), 1030 (P—O—C); 5a (n=2): 3349 (OH), 2259 (CN), 1771 (C=O ester), 1643 (C=O, amide), 1025 (P—O—C); 5b (n=2): 3302 (OH), 2257 (CN), 1744 (C=O ester), 1650 (C=O, amide), 1029 (P—O—C); 5c (n=2): 3316 (OH), 2265 (CN), 1709 (C=O ester), 1649 (C=O, amide), 1027 (P—O—C); 5d (n=2): 3317 (OH), 2247 (CN), 1741 (C=O ester), 1658 (C=O, amide), 1030 (P—O—C); 5a (n=3): 3357 (OH), 2253 (CN), 1774 (C=O ester), 1646 (C=O, amide), 1029 (P—O—C); 5b (n=3): 3359 (OH), 2255 (CN), 1739 (C=O ester), 1653 (C=O, amide), 1030 (P—O—C); 5c (n=3): 3357 (OH), 2260 (CN), 1722 (C=O ester), 1646 (C=O, amide), 1025 (P—O—C); 5d (n=3): 3328 (OH), 2252 (CN), 1738 (C=O ester), 1646 (C=O, amide), 1033 (P—O—C); 5a (n=4): 3322 (OH), 2255 (CN), 1723 (C=O ester), 1648 (C=O, amide), 1025 (P—O—C); 5b (n=4): 3341 (OH), 2258 (CN), 1745 (C=O ester), 1651 (C=O, amide), 1033 (P—O—C); 5c (n=4): 3333 (OH), 2254 (CN), 1775 (C=O ester), 1648 (C=O, amide), 1029 (P—O—C); 5d (n=4): 3329 (OH), 2254 (CN), 1737 (C=O ester), 1648 (C=O, amide), 1026 (P—O—C); 5a (n=11): 3339 (OH), 2257 (CN), 1779 (C=O ester), 1646 (C=O, amide), 1031 (P—O—C); 5b (n=11): 3367 (OH), 2262 (CN), 1749 (C=O ester), 1646 (C=O, amide), 1024 (P—O—C); 5c (n=11): 3318 (OH), 2253 (CN), 1733 (C=O ester), 1661 (C=O, amide), 1027 (P—O—C); 5d (n=11): 3350 (OH), 2251 (CN), 1744 (C=O ester), 1649 (C=O, amide), 1028 (P—O—C); 5e (n=11): 3346 (OH), 2258 (CN), 1726 (C=O ester), 1659 (C=O, amide), 1024 (P—O—C); 5f (n=11): 3340 (OH), 2255 (CN), 1738 (C=O ester), 1646 (C=O, amide), 1024 (P—O—C); 5g (n=11): 3333 (OH), 2254 (CN), 1775 (C=O ester), 1648 (C=O, amide), 1029 (P—O—C); 5h (n=11): 3339 (OH), 2250 (CN), 1736 (C=O ester), 1660 (C=O, amide), 1024 (P—O—C).

Preparation of ODNs Containing Diphosphate Diester Derivatives (8-20) from Polymer-Bound Diphosphite Triester Precursors (5a-h, n=0-4, 11)

t-Butyl hydroperoxide in decane (5-6 M, 4 eq) was added to the resins 5a-d (n=0-4, 11) in THF (1 mL) and DMSO (4 mL). After 2 h shaking at room temperature, the resins were collected by filtration and washed with DMSO (3×15 mL), THF (3×15 mL) and MeOH (3×15 mL), respectively, and were dried overnight at room temperature under vacuum to give polymer-bound diphosphate triester 6a-h (n=0-4, 11). To the swelled resins 6a-h (n=0-4, 11) in THF (1 mL) and DMSO (4 mL) was added DBU (2 eq). After 50 h shaking of the mixture at room temperature, the resins were collected by filtration and washed with DMSO (3×15 mL), THF (3×15 mL) and MeOH (3×15 mL), respectively, and were dried overnight at room temperature under vacuum to give polymer-bound diphosphate diester 7a-h (n=0-4, 11). FT-IR C≡N peaks were disappeared for all the polymer-bound diphosphodiesters. To the swelled resins 7a-h (n=0-4, 11) in anhydrous DCM (1 mL) was added DCM/TFA/water/1,2-ethanedithiol (23:72.5:2.5:2 v/v, 5 mL). After 25 min shaking of the mixtures at room temperature, the resins were collected by filtration and washed with DCM (2×10 mL), THF (2×10 mL), and MeOH (10 mL), respectively. The solvents of filtrate solutions were evaporated at −20° C. The residues were mixed with Amberlite AG-50W-X8 (100-200 mesh, hydrogen form, 500 mg, 1.7 meq/g) in water:dioxane (75:25 v/v, 5 mL) for 30 min at −20° C. After filtration, the solvents were evaporated and the crude products were purified using a $C_{18}$ Sep-Pak cartridge and appropriate solvents. For 12-mer analogues, the solvents were evaporated and the crude products were repurified on HPLC as explained above. After evaporation of organic solvents, the residues were lyophilized to yield 8-20. The purity and total isolated yields for products are shown in Table 1.

5-O-Thymidine Diphosphate (dT, 8a). HR-MS (ESI-TOF) (m/z) calcd, 402.0229; found, 402.0224 [M]$^+$; Anal. calcd, P 15.40%; found, 15.31%.

5-O-(2'-Deoxyadenosine)Diphosphate (dA, 8b). HR-MS (ESI-TOF) (m/z): calcd, 411.0345; found 411.0577 [M]$^+$; Anal. calcd, P 15.06%; found 14.89%.

5-O-(2'-Deoxyguanosine)Diphosphate (dG, 8c). HR-MS (ESI-TOF) (m/z): calcd, 427.0294; found, 426.0298 [M−1]$^-$; Anal. calcd, P 14.50%; found, 14.63%.

5-O-(2'-Deoxycytidine)Diphosphate (dC, 8d). HR-MS (ESI-TOF) (m/z) calcd, 387.0233; found, 388.0219 [M+1]$^+$; Anal. calcd, P 16.00%; found, 15.92%.

Modified d(TT) Containing Diphosphodiester Internucleotide Linkage (9a). Decoupled $^{31}$P NMR (in DMSO-$d_6$ and $H_3PO_4$ 85% in water as external standard, 162 MHz, δ ppm): −11.81 (s), −10.34 (s), −8.55 (s), 3.12 (s, terminal phosphorus); HR-MS (ESI-TOF) (m/z): calcd, 786.0353; found, 786.3072 [M]$^+$; Anal. calcd, P 15.76%; found, 15.71%.

Modified d(AA) Containing Diphosphodiester Internucleotide Linkage (9b). Decoupled $^{31}$P NMR (in DMSO-$d_6$ and $H_3PO_4$ 85% in water as external standard, 162 MHz, δ ppm): −17.36 (s), −15.84 (s), −12.24 (s), 1.96 (s, terminal phosphorus); HR-MS (ESI-TOF) (m/z): calcd, 804.0584; found, 805.0576 [M+1]$^+$; Anal. calcd, P 15.40%; found, 15.28%.

Modified d(GG) Containing Diphosphodiester Internucleotide Linkage (9c). Decoupled $^{31}$P NMR (in DMSO-$d_6$ and $H_3PO_4$ 85% in water as external standard, 162 MHz, δ ppm): −14.31 (s), −13.77 (s), −12.98 (s), 2.86 (s, terminal phosphorus); HR-MS (ESI-TOF) (m/z): calcd, 836.0483; found, 836.9737 [M+1]$^+$; Anal. calcd, P 14.81%; found, 15.03%.

Modified d(CC) Containing Diphosphodiester Internucleotide Linkage (9d). Decoupled $^{31}$P NMR (in DMSO-$d_6$ and $H_3PO_4$ 85% in water as external standard, 162 MHz, δ ppm): −17.61 (s), −14.21 (s), −10.56 (s), 2.56 (s, terminal phosphorus); HR-MS (ESI-TOF) (m/z): calcd, 756.036; found, 756.7475 [M]$^+$; Anal. calcd, P 16.38%; found, 16.33%.

Modified d(TTT) Containing Diphosphodiester Internucleotide Linkage (10a). Decoupled $^{31}$P NMR (in DMSO-$d_6$ and $H_3PO_4$ 85% in water as external standard, 162 MHz, δ ppm): −13.71 (s), −12.23 (s), −11.77 (s), −10.29 (s), −9.30 (s), 2.37 (s, terminal phosphorus); HR-MS (ESI-TOF) (m/z): calcd, 1184.0633; found, 1185.0637 [M+1]$^+$; Anal. calcd, P 15.69%; found, 15.87%.

Modified d(AAA) Containing Diphosphodiester Internucleotide Linkage (10b). Decoupled $^{31}$P NMR (in DMSO-$d_6$ and $H_3PO_4$ 85% in water as external standard, 162 MHz, δ ppm): −18.93 (s), −18.51 (s), −15.35 (s), −10.10 (s), −9.69 (s), 1.79 (s, terminal phosphorus); HR-MS (ESI-TOF) (m/z): calcd, 1211.0980; found, 1228.0290 [M+$H_2O$−1]$^-$; Anal. calcd, P 15.34%; found 15.46%.

Modified d(GGG) Containing Diphosphodiester Internucleotide Linkage (10c). Decoupled $^{31}$P NMR (in DMSO-$d_6$ and H$_3$PO$_4$ 85% in water as external standard, 162 MHz, δ ppm): −15.16 (s), −15.00 (s), −14.98 (s), −12.79 (s), −11.89 (s), 3.27 (s, terminal phosphorus); HR-MS (ESI-TOF) (m/z) calcd, 1259.0828; found 1258.0618 [M−1]$^-$; Anal. calcd, P 14.75%; found, 15.67%.

Modified d(CCC) Containing Diphosphodiester Internucleotide Linkage (10d). Decoupled $^{31}$P NMR (in DMSO-$d_6$ and H$_3$PO$_4$ 85% in water as external standard, 162 MHz, δ ppm): −18.10 (s), −16.06 (s), −14.00 (s), −12.16 (s), −11.04 (s), 2.08 (s, terminal phosphorus); HR-MS (ESI-TOF) (m/z): calcd, 1139.0643; found, 1138.0715 [M−1]$^-$; Anal. calcd, P 16.31%; found, 16.22%.

Modified d(TTTT) Containing Diphosphodiester Internucleotide Linkage (11a). Decoupled $^{31}$P NMR (in DMSO-$d_6$ and H$_3$PO$_4$ 85% in water as external standard, 162 MHz, δ ppm): −14.23 (s), −12.92 (s), −12.02 (s), −10.72 (s), −10.37 (s), −10.10 (s), −9.06 (s), 3.20 (s, terminal phosphorus); HR-MS (ESI-TOF) (m/z): calcd, 1554.0600, found, 1554.1416 [M]$^+$; Anal. calcd, P 15.94%; found, 15.87%.

Modified d(AAAA) Containing Diphosphodiester Internucleotide Linkage (11b). Decoupled $^{31}$P NMR (in DMSO-$d_6$ and H$_3$PO$_4$ 85% in water as external standard, 162 MHz, δ ppm): −17.71 (s), −17.00 (s), −16.32 (s), −14.15 (s), −12.60 (s), −12.17 (s), −9.97 (s), 3.00 (s, terminal phosphorus); HR-MS (ESI-TOF) (m/z): calcd, 1590.1063; found, 1589.1103 [M−1]$^-$; Anal. calcd, P 15.58%; found, 15.72%.

Modified d(GGGG) Containing Diphosphodiester Internucleotide Linkage (11c). Decoupled $^{31}$P NMR (in DMSO-$d_6$ and H$_3$PO$_4$ 85% in water as external standard, 162 MHz, δ ppm): −17.46 (s), −15.09 (s), −14.20 (s), −11.81 (s), −11.67 (s), −11.47 (s), −10.77 (s), 2.10 (s, terminal phosphorus); HR-MS (ESI-TOF) (m/z): calcd, 1654.0860; found, 1652.9015 [M−1]$^-$; Anal. calcd, P 14.97%; found, 15.12%.

Modified d(CCCC) Containing Diphosphodiester Internucleotide Linkage (11d). Decoupled $^{31}$P NMR (in DMSO-$d_6$ and H$_3$PO$_4$ 85% in water as external standard, 162 MHz, δ ppm): −17.68 (s), −14.84 (s), −13.79 (s), −13.00 (s), −11.15 (s), −9.31 (s), −9.11 (s), 1.97 (s, terminal phosphorus); HR-MS (ESI-TOF) (m/z): calcd, 1494.0614; found, 1494.1590 [M]$^+$; Anal. calcd, P 16.58%; found, 16.50%.

Modified d(TTTTT) Containing Diphosphodiester Internucleotide Linkage (12a). $^1$H NMR (DMSO-$d_6$, 400 MHz, δ ppm): 1.75-1.79 (br s, 5-CH$_3$, 15H), 2.20-2.44 (m, H-2' and H-2", 10H), 3.49-3.70 (m, H-5' and H-5", 10H), 3.74-3.84 (m, H-4', 5H), 4.20-4.30 and 4.35-4.45 (m, H-3', 5H), 4.95-5.09 (m, OH, 2H), 5.15-5.31 (m, OH, 5H), 6.07-6.14 and 6.15-6.22 (m, H-1', 5H), 7.68-7.70 and 7.70-7.72 (br s, H-6, 5H), 11.14-11.40 (br s, NH, 5H); $^{13}$C NMR (DMSO-$d_6$, 100 MHz, δ ppm): 13.73 (5-CH$_3$), 41.20 (C-2'), 63.27 (C-5'), 72.50 (C-3'), 89.41, 85.99 (C-4', C-1'), 111.84 (C-5), 138.80 (C-6), 153.27 (C-2 C=O), 166.74 (C-4 C=O); Decoupled $^{31}$P NMR (in DMSO-$d_6$ and H$_3$PO$_4$ 85% in water as external standard, 162 MHz, δ ppm): −15.78 (s), −14.68 (s), −13.58 (s), −12.80 (s), −11.75 (s), −10.65 (s), −9.87 (s), −8.80 (s), −8.29 (s), 2.29 (s, terminal phosphorus); HR-MS (ESI-TOF) (m/z): calcd, 1952.0881; found, 1953.8401 [M+1]$^+$; Anal. calcd, P 15.86%; found, 16.05%.

Modified d(AAAAA) Containing Diphosphodiester Internucleotide Linkage (12b). $^1$H NMR (DMSO-$d_6$, 400 MHz, δ ppm): 2.25-2.43 (m, H2', 5H), 2.70-2.85 (m, H2", 5H), 3.50-3.75 (m, H-5', 10H), 3.95-4.05 (m, H-4', 5H), 4.45-4.55 (m, H-3', 5H), 5.40-5.65 (m, OH, 10H), 6.35-6.50 (m, H-1', 5H), 7.45-7.60 (br s, 6-NH$_2$, 10H), 8.19-8.23 (br s, H-2, 5H), 8.36-8.40 (br s, H-8, 5H); $^{13}$C NMR (DMSO-$d_6$, 100 MHz, δ ppm): 40.40 (C-2'), 85.07 (C-1'), 62.75 (C-5'), 71.87 (C-3'), 88.87 (C-4'), 120.11 (C-5), 140.65 (C-8), 149.65 (C-4), 153.29 (C-2), 156.88 (C-6); Decoupled $^{31}$P NMR (in DMSO-$d_6$ and H$_3$PO$_4$ 85% in water as external standard, 162 MHz, δ ppm): −20.20 (s), −17.36 (s), −17.07 (s), −16.11 (s), −16.07 (s), −12.18 (s), −11.79 (s), −11.18 (s), −11.18 (s), 2.07 (s, terminal phosphorus); HR-MS (ESI-TOF) (m/z) calcd, 1997.1459; found, 1998.1764 [M+1]$^+$; Anal. calcd, P 15.50%; found, 15.39%.

Modified d(GGGGG) Containing Diphosphodiester Internucleotide Linkage (12c). $^1$H NMR (DMSO-$d_6$, 400 MHz, δ ppm): 2.15-2.25 (m, H2', 5H), 2.45-2.58 (m, H2", 5H), 3.50-3.60 (m, H-5' and H-5", 10H), 3.75-3.85 (m, H-4', 5H), 4.30-4.40 (m, H-3', 5H), 4.95-5.05 (m, OH, 5H), 5.27-5.30 (m, OH, 5H), 6.05-6.15 (m, H-1', 5H), 6.40-6.60 (br s, 6-NH$_2$, 10H), 7.85-8.00 (br s, H-8, 5H), 10.70-10.75 (br s, NH, 5H); $^{13}$C NMR (DMSO-$d_6$, 100 MHz, δ ppm): 40.39 (C-2'), 62.54 (C-5'), 71.59 (C-3'), 83.42 (C-1'), 88.41 (C-4'), 117.44 (C-5), 136.22 (C-8), 151.75 (C-4), 154.50 (C-2), 157.67 (C-6); Decoupled $^{31}$P NMR (in DMSO-$d_6$ and H$_3$PO$_4$ 85% in water as external standard, 162 MHz, δ ppm): −19.46 (s), −19.33 (s), −16.30 (s), −16.20 (s), −15.23 (s), −11.67 (s), −10.91 (s), −10.84 (s), −10.20 (s), 2.78 (s, terminal phosphorus); HR-MS (ESI-TOF) (m/z) calcd, 2077.1205; found, 2076.6367 [M−1]$^-$; Anal. Calcd, P 14.91%; found, 15.13%.

Modified d(CCCCC) Containing Diphosphodiester Internucleotide Linkage (12d). $^1$H NMR (DMSO-$d_6$, 400 MHz, δ ppm): 2.10-2.50 (m, H-2' and H-2", 10H), 3.45-3.65 (m, H-5' and H-5", 10H), 3.75-3.86 (m, H-4', 5H), 4.15-4.27 (m, H-3', 5H), 5.15-5.75 (m, OH, 10H), 5.98-6.05 (m, H-1', 5H), 6.17-6.24 (m, H-5, 5H), 8.17-8.32 (m, H-6, 5H), 8.70-8.83 (m, NH, 5H), 9.85-10.10 (br s, NH, 5H); $^{13}$C NMR (DMSO-$d_6$, 100 MHz, δ ppm): 41.08 (C-2'), 61.49 (C-5'), 70.54 (C-3'), 88.86, 86.67 (C-4', C-1'), 94.55 (C-5), 145.30 (C-6), 147.64 (C-2), 160.25 (C-4); Decoupled $^{31}$P NMR (in DMSO-$d_6$ and H$_3$PO$_4$ 85% in water as external standard, 162 MHz, δ ppm): −17.46 (s), −17.06 (s), −14.84 (s), −14.40 (s), −14.33 (s), −13.19 (s), −11.57 (s), −11.53 (s), −11.50 (s), −11.09 (s), 2.86 (s, terminal phosphorus); HR-MS (ESI-TOF) (m/z): calcd, 1877.0897; found, 1878.0569 [M+1]$^+$; Anal. calcd, P 16.49%; found, 16.61%.

Modified d(AAAAAAAAAAAA) (SEQ ID NO: 1) Containing Diphosphodiester Internucleotide Linkage (13). $^1$H NMR (DMSO-$d_6$, 400 MHz, δ ppm): 2.10-2.35 (m, H2', 12H), 2.60-2.80 (m, H2", 12H), 3.50-3.70 (m, H-5', H5", 24H), 3.75-3.95 (m, H-4', 12H), 4.25-4.45 (m, H-3', 12H), 5.10-5.40 (m, OH, 24H), 6.20-6.50 (m, H-1', 12H), 7.20-7.50 (br s, 6-NH$_2$, 24H), 8.05-8.20 (br s, H-2, 12H), 8.30-8.40 (br s, H-8, 12H); $^{31}$P NMR (in DMSO-$d_6$ and H$_3$PO$_4$ 85% in water as external standard, 162 MHz, δ ppm): −16.20 to −13.00 (m, 23P), 1.41 (d, J=16.2 Hz, terminal phosphorus, 1P); MALDI-TOF (m/z): calcd, 4734.3; found, 4734.2; Anal. calcd, P 15.70%; found, 15.91%.

Modified d(TTTTTTTTTTTT) (SEQ ID NO: 2) Containing Diphosphodiester Internucleotide Linkage (14). $^1$H NMR (DMSO-$d_6$, 400 MHz, δ ppm): 1.75-1.79 (br s, 5-CH$_3$, 36H), 2.20-2.44 (m, H-2' and H-2", 24H), 3.49-3.70 (m, H-5' and H-5", 24H), 3.74-3.84 (m, H-4', 12H), 4.20-4.30 and 4.35-4.45 (m, H-3', 12H), 4.95-5.09 (m, OH, 5H), 5.15-5.31 (m, OH, 5H), 6.07-6.14 and 6.15-6.22 (m, H-1', 12H), 7.67-7.71 and 7.69-7.73 (br s, H-6, 12H), 11.14-11.40 (br s, NH, 12H); $^{31}$P NMR (in DMSO-$d_6$ and H$_3$PO$_4$ 85% in water as external standard, 162 MHz, δ ppm): −15.2 to −12.90 (m, 23P), 1.29 (d, J=14.6 Hz, terminal phosphorus, 1P); MALDI-TOF (m/z): calcd, 4626.2; found, 4626.9; Anal. calcd, P 16.06%; found, 15.87%.

Modified d(CCCCCCCCCCCC) (SEQ ID NO: 3) Containing Diphosphodiester Internucleotide Linkage (15). $^1$H NMR (DMSO-$d_6$, 400 MHz, δ ppm): 2.09-2.40 (m, H-2' and H-2", 24H), 3.45-3.65 (m, H-5' and H-5", 24H), 3.79-3.86 (m, H-4', 12H), 4.18-4.24 (m, H-3', 12H), 4.95-5.80 (m, OH, 24H), 5.96-6.08 (m, H-1', 12H), 6.16-6.23 (m, H-5, 12H), 8.20-8.30 (m, H-6, 12H), 8.70-8.83 (m, NH, 12H), 9.85-10.10 (br s, NH, 12H); $^{31}$P NMR (in DMSO-$d_6$ and $H_3PO_4$ 85% in water as external standard, 162 MHz, δ ppm): −16.70 to −14.85 (m, 23P), 1.64 (d, J=16.2 Hz, terminal phosphorus, 1P); MALDI-TOF (m/z): calcd, 4446.2; found, 4446.9; Anal. calcd, P 16.71%; found, 16.63%.

Modified d(GGGGGGGGGGGG) (SEQ ID NO: 4) Containing Diphosphodiester Internucleotide Linkage (16). $^1$H NMR (DMSO-$d_6$, 400 MHz, δ ppm): 2.15-2.23 (m, H2', 12H), 2.43-2.54 (m, H2", 12H), 3.50-3.60 (m, H-5' and H-5", 24H), 3.76-3.84 (m, H-4', 12H), 4.20-4.40 (m, H-3', 12H), 4.95-5.05 (m, OH, 12H), 5.20-5.30 (m, OH, 12H), 6.05-6.15 (m, H-1', 12H), 6.40-6.60 (br s, 6-$NH_2$, 24H), 7.90-8.00 (br s, H-8, 12H), 10.65-10.80 (br s, NH, 12H); $^{31}$P NMR (in DMSO-$d_6$ and $H_3PO_4$ 85% in water as external standard, 162 MHz, δ ppm): −16.62 to −14.50 (m, 23P), 1.00-1.35 (m, terminal phosphorus, 1P); MALDI-TOF (m/z): calcd, 4926.2; found, 4927.8; Anal. calcd, P 15.08%; found, 15.27%.

Modified d(ATATATATATAT) (SEQ ID NO: 5) Containing Diphosphodiester Internucleotide Linkage (17). $^1$H NMR (DMSO-$d_6$, 400 MHz, δ ppm): 1.60-1.84 (br s, 5-$CH_3$, dT, 18H), 2.20-2.80 (m, H-2' and H-2", dA, dT, 24H), 3.49-3.74 (m, H-5' and H-5", dA, dT, 24H), 3.74-3.79 (m, H-4', dT, 6H), 3.79-3.92 (m, H-4', dA, 6H), 4.20-4.27 (m, H-3', dT, 6H), 4.40-4.45 (m, H-3', dA, 6H), 5.02-5.09 (m, OH, dT, 6H), 5.22-5.40 (m, OH, dA, dT, 16H), 6.14-6.21 (m, H-1', dT, 6H), 6.27-6.40 (m, H-1', dA, 6H), 7.20-7.40 (br s, 6-$NH_2$, dA, 12H), 7.69-7.73 (br s, H-6, dT, 6H), 8.12-8.17 (br s, H-2, dA, 6H), 8.33-8.38 (br s, H-8, dA, 6H), 11.20-11.40 (br s, NH, dT, 6H); $^{31}$P NMR (in DMSO-$d_6$ and $H_3PO_4$ 85% in water as external standard, 162 MHz, δ ppm): −18.11 to −16.30 (m, 23P), 1.93 (d, J=14.6 Hz, terminal phosphorus, 1P); MALDI-TOF (m/z): calcd, 4680.2; found, 4681.0; Anal. calcd, P 15.88%; found, 15.72%.

Modified d(TATATATATATA) (SEQ ID NO: 6) Containing Diphosphodiester Internucleotide Linkage (18). $^1$H NMR (DMSO-$d_6$, 400 MHz, δ ppm): 1.60-1.84 (br s, 5-$CH_3$, dT, 18H), 2.20-2.80 (m, H-2' and H-2", dA, dT, 24H), 3.45-3.74 (m, H-5' and H-5", dA, dT, 24H), 3.74-3.79 (m, H-4', dT, 6H), 3.79-3.92 (m, H-4', dA, 6H), 4.20-4.27 (m, H-3', dT, 6H), 4.39-4.45 (m, H-3', dA, 6H), 5.02-5.09 (m, OH, dT, 6H), 5.20-5.40 (m, OH, dA, dT, 16H), 6.13-6.21 (m, H-1', dT, 6H), 6.27-6.40 (m, H-1', dA, 6H), 7.19-7.40 (br s, 6-$NH_2$, dA, 12H), 7.63-7.75 (br s, H-6, dT, 6H), 8.10-8.17 (br s, H-2, dA, 6H), 8.31-8.38 (br s, H-8, dA, 6H), 11.20-11.40 (br s, NH, dT, 6H); $^{31}$P NMR (in DMSO-$d_6$ and $H_3PO_4$ 85% in water as external standard, 162 MHz, δ ppm): −17.36 (s), −18.05 to −16.54 (m, 23P), 1.39 (d, J=16.2 Hz, terminal phosphorus, 1P); MALDI-TOF (m/z): calcd, 4680.2; found, 4681.0; Anal. calcd, P 15.88%; found, 16.09%.

Modified d(CGCGCGCGCGCG) (SEQ ID NO: 7) Containing Diphosphodiester Internucleotide Linkage (19). $^1$H NMR (DMSO-$d_6$, 400 MHz, δ ppm): 2.10-2.58 (m, H-2' and H-2", dG, dC, 24H), 3.45-3.65 (m, H-5' and H-5", dG, dC, 24H), 3.75-3.90 (m, H-4', dG, dC, 12H), 4.18-4.29 (m, H-3', dC, 6H), 4.30-4.40 (m, H-3', dG, 6H), 4.60-5.80 (m, OH, dG, dC, 20H), 5.98-6.20 (m, H-1', H-5, dC; H-1', dG, 18H), 6.40-6.80 (br s, 6-$NH_2$, dG, 12H), 7.85-8.10 (br s, H-8, dG, 6H), 8.10-8.32 (m, H-6, dC, 6H), 8.50-8.85 (m, NH, dC, 6H), 9.40-9.80 (br s, NH, dC, 6H), 10.90-11.20 (br s, dG, NH, 6H); $^{31}$P NMR (in DMSO-$d_6$ and $H_3PO_4$ 85% in water as external standard, 162 MHz, δ ppm): −18.25 to −14.71 (m, 23P), 1.77 (d, J=16.2 Hz, terminal phosphorus, 1P); MALDI-TOF (m/z): calcd, 4686.2; found, 4687.2 [M+1]$^+$; Anal. calcd, P 15.86%; found, 15.74%.

Modified d(GCGCGCGCGCGC) (SEQ ID NO: 8) Containing Diphosphodiester Internucleotide Linkage (20). $^1$H NMR (DMSO-$d_6$, 400 MHz, δ ppm): 2.10-2.58 (m, H-2' and H-2", dG, dC, 24H), 3.45-3.65 (m, H-5' and H-5", dG, dC, 24H), 3.75-3.90 (m, H-4', dG, dC, 12H), 4.18-4.29 (m, H-3', dC, 6H), 4.30-4.40 (m, H-3', dG, 6H), 4.60-5.80 (m, OH, dG, dC, 20H), 5.98-6.21 (m, H-1', H-5, dC; H-1', dG, 18H), 6.58-6.80 (br s, 6-$NH_2$, dG, 12H), 7.85-8.10 (br s, H-8, dG, 6H), 8.10-8.32 (m, H-6, dC, 6H), 8.50-8.85 (m, NH, dC, 6H), 9.40-9.80 (br s, NH, dC, 6H), 10.89-11.19 (br s, dG, NH, 6H); $^{31}$P NMR (in DMSO-$d_6$ and $H_3PO_4$ 85% in water as external standard, 162 MHz, δ ppm): −19.38 to −14.05 (m, 23P), 1.83 (d, J=16.2 Hz, terminal phosphorus, 1H); MALDI-TOF (m/z): calcd, 4686.2; found, 4687.3 [M]$^+$; Anal. calcd, P 15.86%, found, 16.12%.

Solid-Phase Diphosphorylation Using Aminomethyl Polystyrene Resin Linked Through Amide Bond with p-Acetoxybenzyl Alcohol (31A) and Aminomethyl Polystyrene Resin Linked Through Reduced Amide Bond with p-Acetoxybenzyl Alcohol (31B)

Preparation of diphosphitylating reagent bis(2-cyanoethyl diisopropylphosphoramidite) (26). Phosphorus trichloride (21, 1.75 mL, 20 mmol) and 3-hydroxypropionitrile (22, 1.37 mL, 20 mmol) were added to anhydrous $CH_3CN$ (30 mL) under dry nitrogen. The mixture was stirred for 10 min at room temperature to yield 23. Diisopropylamine (2.81 mL, 20 mmol) was added to the reaction mixture and the stirring was continued for additional 30 min under dry nitrogen to give 2-cyanoethyl diisopropylphosphoramidochloridite (24). Half of the reaction mixture was transferred to another reaction vessel containing water (0.18 mL, 10 mmol) and was stirred at room temperature for 10 min under nitrogen to yield 25. Compound 24 (1 eq) was added to the reaction mixture of 25 (1 eq) and the stirring was continued for 30 min to afford bis(2-cyanoethyl diisopropylphosphoramidite) (26) (4.04 g, 97%). The reaction mixture containing diphosphitylating reagent 26 was immediately used in coupling reactions with polymer-bound p-acetoxybenzyl alcohol (31A) and polymer-bound N-Boc p-acetoxybenzyl alcohol (31B). Stability studies using HR-MS indicated that the compound remained stable even after two weeks storage at −20° C.

$^1$H NMR (DMSO-$d_6$): δ 0.94 (d, J=7.2 Hz, $CH_3$, 24H), 2.58 (t, J=6.0 Hz, $CH_2CN$, 4H), 2.75-2.85 (m, CH, 4H), 3.59 (t, J=6.0 Hz, $CH_2O$, 4H); $^{13}$C NMR (DMSO-$d_6$): δ 21.85, 23.84, 45.28, 57.31, 120.33; $^{31}$P NMR (DMSO-$d_6$ and $H_3PO_4$ 85% in water as external standard): δ 118.63 (s); HR-MS (ESI-TOF) (m/z) calcd. 418.2263, found 419.2306 [M+H]$^+$.

Preparation of polymer-bound bis(2-cyanoethyl diisopropylphosphoramidite) (32A and 32B). The prepared reaction mixture containing bis(2-cyanoethyl diisopropylphosphoramidite) 26 (~10 mmol) as described above was added to a swelled solution of polymer-bound p-acetoxybenzyl alcohol 31A (3.05 g, 0.87 mmol/g) or polymer-bound N-Boc p-acetoxybenzyl alcohol 31B (3.75 g, 0.72 mmol/g) and 1H-tetrazole (531 mg, 7.5 mmol) in anhydrous THF (25 mL) and the mixture was shaken for 24 h at room temperature. The resin was collected by filtration, washed with $CH_3CN$ (2×30 mL), THF (2×30 mL), and MeOH (2×30 mL), respectively, and dried under vacuum to give 32A (3.84 g, 93%, 0.74 mmol/g) or 32B (4.57 g, 95%, 0.56 mmol/g). IR (cm$^{-1}$): 32A: 2256 (CN), 1756 (C=O ester), 1650 (C=O, amide), 1029 (P—O—C); 32B: 2252 (CN), 1757 (C=O ester), 1025 (P—O—C).

Preparation of polymer-bound 5-O-[bis(2-cyanoethyl phosphite triester)]thymidine (34a and 35a), 5-O-[bis(2-cyanoethyl phosphite triester)]uridine (34b and 35b), 5-O-[bis(2-cyanoethyl phosphite triester)]-3-azido-3-deoxythymidine (34c and 35c), 5-O-[bis(2-cyanoethyl phosphite triester)]adenosine (34d and 35d), 6-O-[bis(2-cyanoethyl phosphite triester)]-α,β-D-mannose (34e and 35e), 6-O-[bis(2-cyanoethyl phosphite triester)]-β-D-galactopyranose (34f and 35f), 1-O-[bis(2-cyanoethyl phosphite triester)]-β-D-fructospyranose (34g and 35g), 6-O-[D-galactopyranosyl-6-O-bis(2-cyanoethyl phosphite triester)]-α,β-D-glucose (34h and 35h)

Nucleosides and carbohydrates (a-h, 1.28 mmol) and 1H-tetrazole (68 mg, 0.96 mmol) were added to 32A (433 mg, 0.74 mmol/g) or 32B (572 mg, 0.56 mmol/g) in anhydrous THF (2 mL) and DMSO (2-3 mL) or in anhydrous DMSO (5 mL) in case of adenosine. The mixture was shaken for 24 h at room temperature. The resin was collected by filtration and washed with DMSO (3×20 mL), THF (2×15 mL), and MeOH (3×20 mL), respectively, and dried under vacuum to give 34a-h (442-475 mg) or 35a-h (586-631 mg), respectively. IR (cm$^{-1}$): 34a: 3330 (OH), 2252 (CN), 1759 (C=O ester), 1650 (C=O, amide), 1025 (P—O—C); 34b: 3325 (OH), 2255 (CN), 1765 (C=O ester), 1649 (C=O, amide), 1026 (P—O—C); 34c: 2248 (CN), 1766 (C=O ester), 1647 (C=O, amide), 1029 (P—O—C); 34d: 3359 (OH), 2253 (CN), 1752 (C=O ester), 1644 (C=O, amide), 1027 (P—O—C); 34e: 3315 (OH), 2255 (CN), 1767 (C=O ester), 1654 (C=O, amide), 1025 (P—O—C); 34f: 3307 (OH), 2252 (CN), 1766 (C=O ester), 1650 (C=O, amide), 1029 (P—O—C); 34g: 3313 (OH), 2257 (CN), 1748 (C=O ester), 1646 (C=O, amide), 1029 (P—O—C); 34h: 3311 (OH), 2254 (CN), 1762 (C=O ester), 1651 (C=O, amide), 1025 (P—O—C); 35a: 3335 (OH), 2253 (CN), 1755 (C=O ester), 1025 (P—O—C); 35b: 3327 (OH), 2254 (CN), 1759 (C=O ester), 1026 (P—O—C); 35c: 2253 (CN), 1759 (C=O ester), 1029 (P—O—C); 35d: 3338 (OH), 2260 (CN), 1759 (C=O ester), 1029 (P—O—C); 35e: 3314 (OH), 2252 (CN), 1755 (C=O ester), 1022 (P—O—C); 35f: 3298 (OH), 2250 (CN), 1760 (C=O ester), 1025 (P—O—C); 35g: 3317 (OH), 2253 (CN), 1763 (C=O ester), 1029 (P—O—C); 35h: 3342 (OH), 2251 (CN), 1766 (C=O ester), 1025 (P—O—C).

Oxidation of polymer-bound diphosphitylated precursors, 34a-h and 35a-h, to polymer-bound 5-O-[bis(2-cyanoethyl phosphate triester)]thymidine (38a and 39a), 5-O-[bis(2-cyanoethyl phosphate triester)]uridine (38b and 39b), 5-O-[bis(2-cyanoethyl phosphate triester)]-3-azido-3-deoxythymidine (38c and 39c), 5-O-[bis(2-cyanoethyl phosphate triester)]adenosine (38d and 39d), 6-O-[bis(2-cyanoethyl phosphate triester)]-α,β-D-mannose (38e and 39e), 6-O-[bis(2-cyanoethyl phosphate triester)]-β-D-galactopyranose (38f and 39f), 1-O-[bis(2-cyanoethyl phosphate triester)]-β-D-fructopyranose (38g and 39g), 6-O-[α-D-galactopyranosyl-6-O-bis(2-cyanoethyl phosphate triester)]-α,β-D-glucose (38h and 39h)

tert-Butyl hydroperoxide in decane (5-6 M, 256 μL, 1.28 mmol) was added to the resins (34a-h, 221-237 mg) or (35a-h, 293-316 mg) in THF (3 mL). After 1 h shaking at room temperature, the resins were collected by filtration and washed with THF (3×15 mL) and MeOH (3×15 mL), respectively, and were dried overnight at room temperature under vacuum to give 38a-h (224-247 mg) or 39a-h (297-330 mg). IR (cm$^{-1}$): 38a: 3345 (OH), 2255 (CN), 1760 (C=O ester), 1646 (C=O, amide), 1026 (P—O—C); 38b: 3403 (OH), 2250 (CN), 1762 (C=O ester), 1647 (C=O, amide), 1025 (P—O—C); 38c: 2258 (CN), 1766 (C=O ester), 1650 (C=O, amide), 1025 (P—O—C); 38d: 3353 (OH), 2257 (CN), 1766 (C=O ester), 1652 (C=O, amide), 1026 (P—O—C); 38e: 3309 (OH), 2253 (CN), 1759 (C=O ester), 1644 (C=O, amide), 1032 (P—O—C); 38f: 3287 (OH), 2255 (CN), 1756 (C=O ester), 1643 (C=O, amide), 1029 (P—O—C); 38g: 3293 (OH), 2257 (CN), 1755 (C=O ester), 1644 (C=O, amide), 1027 (P—O—C); 38h: 3335 (OH), 2252 (CN), 1769 (C=O ester), 1650 (C=O, amide), 1029 (P—O—C); 39a: 3353 (OH), 2253 (CN), 1763 (C=O ester), 1025 (P—O—C); 39b: 3360 (OH), 2252 (CN), 1759 (C=O ester), 1025 (P—O—C); 39c: 2258 (CN), 1766 (C=O ester), 1029 (P—O—C); 39d: 3361 (OH), 2255 (CN), 1762 (C=O ester), 1025 (P—O—C); 39e: 3284 (OH), 2250 (CN), 1763 (C=O ester), 1025 (P—O—C); 39f: 3301 (OH), 2247 (CN), 1762 (C=O ester), 1029 (P—O—C); 39g: 3307 (OH), 2257 (CN), 1769 (C=O ester), 1025 (P—O—C); 39h: 3327 (OH), 2252 (CN), 1766 (C=O ester), 1025 (P—O—C).

Preparation of polymer-bound thymidine-5-O-diphosphodiester (46a and 47a), uridine-5-O-diphosphodiester (46b and 47b), 3-azido-3-deoxythymidine-5-O-diphosphodiester (46c and 47c), adenosine-5-O-diphosphodiester (46d and 47d), α,β-D-mannose-6-O-diphosphodiester (46e and 47e), β-D-galactopyranose-6-O-diphosphodiester (46f and 47f), β-D-fructopyranose-1-O-diphosphodiester (46g and 47g), 6-O-(α-D-galactopyranosyl-6-O-diphosphodiester)-α,β-D-glucose (46h and 47h)

To the swelled resins 38a-h (224-247 mg) or 39a-h (297-330 mg) in THF (3 mL) was added DBU (64 μL, 0.64 mmol). After 48 h shaking of the mixture at room temperature, the resins were collected by filtration and washed with THF (2×15 mL) and MeOH (2×15 mL), respectively, and were dried overnight at room temperature under vacuum to give 46a-h (217-239 mg) or 47a-h (290-319 mg). IR (cm$^{-1}$): 46a: 3299 (O—H), 1759 (C=O ester), 1643 (C=O, amide), 1029 (P—O—C); 46b: 3258 (O—H), 1755 (C=O ester), 1642 (C=O, amide), 1025 (P—O—C); 46c: 1761 (C=O ester), 1644 (C=O, amide), 1027 (P—O—C); 46d: 3312 (O—H), 1752 (C=O ester), 1645 (C=O, amide), 1029 (P—O—C); 46e: 3295 (O—H), 1756 (C=O ester), 1643 (C=O, amide), 1028 (P—O—C); 46f: 3272 (O—H), 1755 (C=O ester), 1641 (C=O, amide), 1025 (P—O—C); 46g: 3255 (O—H), 1750 (C=O ester), 1653 (C=O, amide), 1028 (P—O—C); 46h: 3320 (O—H), 1749 (C=O ester), 1646 (C=O, amide), 1026 (P—O—C); 47a: 3302 (O—H), 1759 (C=O ester), 1027 (P—O—C); 47b: 3329 (O—H), 1759 (C=O ester), 1029 (P—O—C); 47c: 1761 (C=O ester), 1029 (P—O—C); 47d: 3378 (O—H), 1758 (C=O ester), 1025 (P—O—C); 47e: 3233 (O—H), 1759 (C=O ester), 1026 (P—O—C); 47f: 3244 (O—H), 1759 (C=O ester), 1025 (P—O—C); 47g: 3247 (O—H), 1755 (C=O ester), 1028 (P—O—C); 47h: 3302 (O—H), 1752 (C=O ester), 1025 (P—O—C).

Preparation of thymidine-5-O-diphosphate (54a), uridine-5-O-diphosphate (54b), 3-azido-3-deoxythymidine-5-O-diphosphate (54c), adenosine-5-O-diphosphate (54d), α,β-D-mannose-6-O-diphosphate (54e), β-D-galactopyranose-6-O-diphosphate (54f), β-D-fructopyranose-1-O-diphosphate (54g), 6-O-(α-D-galactopyranosyl-6-O-diphosphate)-α,β-D-glucose (54h)

To the swelled resins 46a-h (217-239 mg) or 47a-h (290-319 mg) in anhydrous DCM (1 mL) was added DCM/TFA/ water (24:74:2 v/v, 3 mL). After 25 min shaking of the mixtures at room temperature, the resins were collected by filtration and washed with DCM (2×10 mL), THF (2×10 mL), and MeOH (10 mL), respectively. The solvents of filtrate solutions were immediately evaporated at room temperature for 54a-d and at −20° C. for 54e-h, respectively. The residues were mixed with Amberlite AG-50W-X8 (100-200 mesh, hydrogen form, 500 mg, 1.7 meq/g) in water:dioxane (75:25 v/v, 3 mL) for 15 min at room temperature for 54a-d and at −20° C. for 54e-h, respectively. After filtration, the solvents were evaporated and the crude products were purified using $C_{18}$ Sep-Pak using appropriate solvents. The solvents were evaporated and the residues were dried under vacuum at −20° C. for 24 h to yield 54a-h. The purity and total isolated yields for 54a-h are shown in Table 4. The compounds were characterized by $^1$H NMR, $^{13}$C NMR, $^{31}$P NMR, high resolution mass spectrometer (ESI-TOF), and phosphorus quantitative elemental analysis.

Thymidine-5-O-diphosphate (54a). $^1$H NMR (DMSO-$d_6$): δ 1.75 (d, $J_{5-CH_3, 6}$=1.1 Hz, 5-CH$_3$, 3H), 2.04-2.11 (m, H-2' and H-2", 2H), 3.49-3.64 (m, H-5' and H-5", 2H), 3.70-3.82 (m, H-4', 1H), 4.21-4.28 (m, H-3', 1H), 4.95-5.02 (m, OH, 1H), 5.12-5.25 (m, OH, 1H), 6.15 (t, $J_{1',2'}$ and $J_{1',2''}$=6.8 Hz, H-1', 1H), 7.67 (d, $J_{6,5-CH_3}$=1.1 Hz, H-6, 1H), 11.16-11.21 (br s, N—H, 1H); $^{13}$C NMR (DMSO-$d_6$): δ 13.06 (5-CH$_3$), 40.03 (C-2'), 62.14 (C-5'), 71.28 (C-3'), 84.65 (C-4'), 88.03 (C-1'), 110.25 (C-5), 136.97 (C-6), 151.30 (C-2 C=O), 164.64 (C-4 C=O); $^{31}$P NMR (in DMSO-$d_6$ and H$_3$PO$_4$ 85% in water as external standard): δ −9.23 (s, α-P), −8.72 (s, β-P); HR-MS (ESI-TOF) (m/z) calcd. 402.0229, found 402.0244 [M]$^+$; Anal. Calcd. P 15.40%, found 14.98%.

Uridine-5-O-diphosphate (54b). $^1$H NMR (DMSO-$d_6$): δ 3.50-3.66 (m, H-5' and H-5", 2H), 3.78-3.88 (m, H-4', 1H), 3.92-4.00 (m, H-3', 1H), 4.00-4.06 (m, H-2', 1H), 4.92-5.18 (br s, 2H, OH), 5.26-5.48 (br s, 1H, OH), 5.65 (d, $J_{5,6}$=8.0 Hz, H-5, 1H), 5.78 (d, $J_{1',2'}$=5.2 Hz, H-1', 1H), 7.87 (d, $J_{6,5}$=8.0 Hz, H-6, 1H), 10.90-11.50 (br s, N—H, 1H); $^{13}$C NMR (DMSO-$d_6$): δ 61.67 (C-5'), 70.72 (C-2'), 74.42 (C-3'), 85.63 (C-4'), 88.56 (C-1'), 102.60 (C-5), 141.64 (C-6), 151.60 (C-2 C=O), 164.15 (C-4 C=O); $^{31}$P NMR (in DMSO-$d_6$ and H$_3$PO$_4$ 85% in water as external standard): δ −8.39 (s, α-P), −7.89 (s, β-P); HR-MS (ESI-TOF) (m/z) calcd. 404.0022, found 405.0802 [M+H]$^+$; Anal. Calcd. P 15.33%, found 15.20%.

3'-Azido-3'-deoxythymidine-5'-O-diphosphate (54c). $^1$H NMR (DMSO-$d_6$): δ 1.77 (d, $J_{5-CH_3, 6}$=1.1 Hz, 5-CH$_3$, 3H), 2.22-2.31 (m, H-2', 1H), 2.32-2.42 (m, H-2", 1H), 3.50-3.75 (m, H-5' and H-5", 2H), 3.78-3.83 (m, H-4', 1H), 4.35-4.42 (m, H-3', 1H), 5.10-5.40 (br s, OH, 1H), 6.09 (t, $J_{1',2'}$=6.4 Hz, H-1', 1H), 7.67 (d, $J_{6,5-CH_3}$=1.1 Hz, H-6, 1H), 11.23-11.28 (br s, NH, 1H); $^{13}$C NMR (DMSO-$d_6$): δ 13.02 (5-CH$_3$), 37.12 (C-2'), 60.96 (C-3'), 61.61 (C-5'), 84.29 (C-4'), 84.86 (C-1'), 110.37 (C-5), 136.85 (C-6), 151.25 (C-2 C=O), 164.58 (C-4 C=O); $^{31}$P NMR (DMSO-$d_6$ and H$_3$PO$_4$ 85% in water as external standard): δ −8.05 (s, α-P), −7.55 (s, β-P); HR-MS (ESI-TOF) (m/z) calcd. 427.0294 found 428.0787 [M+H]$^+$; Anal. Calcd. P 14.50%, found 14.73%.

Adenosine-5-O-diphosphate (54d). $^1$H NMR (DMSO-$d_6$): δ 3.58-3.67 (m, H-5', 1H), 3.69-3.77 (m, H-5", 1H), 4.01-4.07 (m, H-4', 1H), 4.18-4.26 (m, H-3', 1H), 4.68 (dd, $J_{2',1'}$=6.4, $J_{2',3'}$=5.7 Hz, H-2', 1H), 5.30-5.37 (m, OH, 1H), 5.52-5.63 (m, OH, 2H), 5.95 (d, $J_{1',2'}$=6.4 Hz, H-1', 1H), 7.45-7.54 (br s, 6-NH$_2$, 2H), 8.21 (s, H-2, 1H), 8.41 (s, H-8, 1H); $^{13}$C NMR (DMSO-$d_6$): δ 62.58 (C-5'); 71.62 (C-2'), 74.41 (C-3'), 86.86 (C-4'), 88.90 (C-1'), 120.23 (C-5), 140.98 (C-8), 149.88 (C-4), 153.31 (C-2), 157.00 (C-6); $^{31}$P NMR (in DMSO-$d_6$ and H$_3$PO$_4$ 85% in water as external standard): δ −6.40 (s, α-P), −5.90 (s, β-P); HR-MS (ESI-TOF) (m/z) calcd. 427.0294, found 428.0519 [M+H]$^+$; Anal. Calcd. P 14.50%, found 14.37%.

α,β-D-Mannose-6-O-diphosphate (54e). $^1$H NMR (DMSO-$d_6$): δ 2.96-3.04 (m, H-5e, 1H), 3.22-3.29 (m, H-4β, 1H), 3.30-3.39 (m, H-3β, H-4α, 2H), 3.40-3.47 (m, H-6α, 1H), 3.45-3.48 (m, H-6β, 1H), 3.48-3.52 (m, H-5α, 1H), 3.50-3.56 (H-6β, H-3α, H-6α, 3H), 3.56-3.65 (m, H-2α, H-2β, 2H), 4.37-4.42 (m, OH-4), 4.44-4.50 (m, OH-3), 4.50-4.55 (m, OH phosphate), 4.56-4.63 (m, H-1β, 1H), 4.66-4.73 (m, OH-2), 4.82-4.88 (m, H-1α, 1H), 6.14 (d, $J_{1β,OH}$=8.4 Hz, OH-1β), 6.18 (d, $J_{1α,OH}$=4.4 Hz, OH-1α); $^{13}$C NMR (DMSO-$d_6$): δ 62.22 (C-6, α and β), 67.70 (C-4β), 68.02 (C-4α), 71.35 (C-3α), 72.08 (C-2α), 72.32 (C-3β), 73.77 (C-5α), 74.45 (C-2β), 77.67 (C-5β), 94.72 (C-1β), 94.81 (C-1α); $^{31}$P NMR (DMSO-$d_6$ and H$_3$PO$_4$ 85% in water as external standard): δ −8.55 (s, α-P), −9.05 (s, β-P); HR-MS (ESI-TOF) (m/z) calcd. 339.9960; found: 341.0018 [M+H]$^+$, Anal. Calcd. P 18.21%, found 18.26%.

β-D-Galactopyranose-6-O-diphosphate (54f). $^1$H NMR (DMSO-$d_6$): δ 3.28-3.42 (m, H-2, 1H), 3.42-3.51 (m, H-6 and H-3, 3H), 3.60-3.70 (m, H-5, 1H), 3.71-3.82 (m, H-4, 1H), 4.15-4.70 (br s, O—H), 4.80-4.92 (m, 1H, H-1), 6.07-6.20 (m, OH-1, 1H); $^{13}$C NMR (DMSO-$d_6$): δ 61.46 (C-6), 69.56 (C-4), 69.75 (C-2), 70.24 (C-3), 71.14 (C-5), 93.35 (C-1); $^{31}$P NMR (in DMSO-$d_6$ and H$_3$PO$_4$ 85% in water as external standard): δ −7.65 (s, αP), −8.15 (s, βP); HR-MS (ESI-TOF) (m/z) calcd. 339.9960; found: 340.9816 [M+H]$^+$, Anal. Calcd. P 18.21%, found 17.79%.

β-D-Fructopyranose-1-O-diphosphate (54g). $^1$H NMR (DMSO-$d_6$): δ 3.25 (d, H-1b, $J_{1b,1a}$=11.6 Hz, 1H), 3.33-3.44 (m, H-1a and H-6b, 2H), 3.47-3.59 (m, H-3 and H-5, 2H), 3.61-3.68 (m, H-4, 1H), 3.75 (d, H-6a, $J_{6a,6b}$=12 Hz, 1H), 4.29 (d, $J_{OH-5,5}$=6.0 Hz, OH-5, 1H), 4.38 (d, $J_{OH-4,4}$=3.6 Hz, OH-4, 1H), 4.46 (d, $J_{OH-3,3}$=4.8 Hz, OH-3, 1H), 4.48-4.54 (m, OH phosphate), 5.16 (s, OH-2, 1H); $^{13}$C NMR (DMSO-$d_6$): δ 63.84 (C-6), 65.12 (C-1), 68.56 (C-3), 69.97 (C-5), 70.69 (C-4), 98.84 (C-2); $^{31}$P NMR (in DMSO-$d_6$ and H$_3$PO$_4$ 85% in water as external standard): δ −8.76 (s, αP), −9.26 (s, βP); HR-MS (ESI-TOF) (m/z) calcd. 339.9960; found: 341.0508 [M+H]$^+$, Anal. Calcd. P 18.21%, found 18.33%.

6-O-(α-D-Galactopyranosyl-6-O-diphosphate)-α,β-D-glucose (54h). $^1$H NMR (DMSO-$d_6$): δ 3.03-3.16 (m, H-2β, H-2α, H-4α, H-4β, H-3β, 5H), 3.36-3.49 (m, H-5β and H-3α, 2H), 3.50-3.56 (m, H-2', 1H), 3.58-3.63 (m, H-3', 1H), 3.64-3.70 (m, H-6α, H-6β, H-6', 6H), 3.70-3.74 (m, H-5', H-4', H-5α, 3H), 4.36-4.42 (m, OH-4'), 4.44-4.50 (m, OH-3α), 4.54-4.60 (OH-2β, OH-2α, OH-3β, OH-3', OH-2'), 4.60-4.68 (m, OH-4α, OH-4β), 4.78-4.83 (m, H-1', 1H), 4.86-4.90 (m, OH Phosphate), 4.90-4.94 (m, H-1β, 1H), 4.95-5.00 (m, H-1α, 1H), 6.26 (d, $J_{1α,OH}$=4.0 Hz, OH-1α), 6.64 (d, $J_{1β,OH}$=6.4 Hz, OH-1β); $^{13}$C NMR (DMSO-$d_6$): δ 61.36 (C-6'), 67.71 (C-6β), 69.17 (C-6α), 69.61 (C-2'), 70.29 (C-4'), 70.99 (C-4β, C-3'), 71.42 (C-4α), 71.58 (C-5α), 72.88 (C-5', C-2α), 73.85 (C-3α), 75.43 (C-2β), 75.46 (C-5β), 77.32 (C-3β), 92.97 (C-1α), 97.52 (C-1β), 99.56, 99.63 (C-1', α, β respectively); $^{31}$P NMR (in DMSO-$d_6$ and H$_3$PO$_4$ 85% in water as external standard): δ −8.85 (s, αP), −9.35 (s, βP); HR-MS (ESI-TOF) (m/z) calcd. 502.0489, found 503.0720 [M+H]$^+$. Anal. Calcd. P 12.33%, found 12.52%.

Solid-Phase Dithiodiphosphorylation Using Aminomethyl Polystyrene Resin Linked Through Amide Bond with p-Acetoxybenzyl Alcohol (31A) and Aminomethyl Polystyrene Resin Linked Through Reduced Amide Bond with p-Acetoxybenzyl Alcohol (31B)

Sulfurization of polymer-bound diphosphitylated precursors, 34a-h and 35a-h, to polymer-bound 5-O-[bis(2-cyanoethyl thiophosphate triester)]thymidine (40a and 41a), 5-O-[bis(2-cyanoethyl thiophosphate triester)]uridine (40b and 41b), 5-O-[bis(2-cyanoethyl thiophosphate triester)]-3-azido-3-deoxythymidine (40c and 41c), 5-O-[bis(2-cyanoethyl thiophosphate triester)]adenosine (40d and 41d), 6-O-[bis(2-cyanoethyl phosphate triester)]-α,β-D-mannose (40e and 41e), 6-O-[bis(2-cyanoethyl thiophosphate triester)]-β-D-galactopyranose (40f and 41f), 1-O-[bis(2-cyanoethyl thiophosphate triester)]-β-D-fructopyranose (40g and 41g), 6-O-[α-D-galactopyranosyl-6-O-bis(2-cyanoethyl thiophosphate triester)]-α,β-D-glucose (40h and 41h)

Beaucage's reagent (3H-1,2-benzodithiole-3-one 1,1-dioxide) (256 mg, 1.28 mmol) was added to the resins (34a-h, 221-237 mg) or (35a-h, 293-316 mg) in $CH_3CN$ (5 mL). After 5 h shaking at 40° C., the resins were collected by filtration and washed with $CH_3CN$ (2×15 mL), THF (2×15 mL), and MeOH (3×15 mL), respectively, and were dried under vacuum to give 40a-h (232-254 mg) or 41a-h (308-341 mg). IR ($cm^{-1}$): 40a: 3335 (OH), 2252 (CN), 1759 (C=O ester), 1647 (C=O, amide), 1029 (P—O—C); 40b: 3317 (OH), 2255 (CN), 1764 (C=O ester), 1647 (C=O, amide), 1027 (P—O—C); 40c: 2250 (CN), 1766 (C=O ester), 1645 (C=O, amide), 1025 (P—O—C); 40d: 3334 (OH), 2257 (CN), 1764 (C=O ester), 1644 (C=O, amide), 1025 (P—O—C); 40e: 3304 (OH), 2258 (CN), 1758 (C=O ester), 1650 (C=O, amide), 1029 (P—O—C); 40f: 3313 (OH), 2253 (CN), 1762 (C=O ester), 1646 (C=O, amide), 1029 (P—O—C); 40g: 3307 (OH), 2253 (CN), 1763 (C=O ester), 1650 (C=O, amide), 1028 (P—O—C); 40h: 3289 (OH), 2249 (CN), 1758 (C=O ester), 1644 (C=O, amide), 1025 (P—O—C); 41a: 3345 (OH), 2252 (CN), 1769 (C=O ester), 1025 (P—O—C); 41b: 3355 (OH), 2254 (CN), 1763 (C=O ester), 1026 (P—O—C); 41c: 2252 (CN), 1762 (C=O ester), 1018 (P—O—C); 41d: 3389 (OH), 2256 (CN), 1762 (C=O ester), 1029 (P—O—C); 41e: 3237 (OH), 2248 (CN), 1766 (C=O ester), 1026 (P—O—C); 41f: 3317 (OH), 2263 (CN), 1759 (C=O ester), 1025 (P—O—C); 41g: 3288 (OH), 2261 (CN), 1763 (C=O ester), 1019 (P—O—C); 41h: 3298 (OH), 2264 (CN), 1769 (C=O ester), 1025 (P—O—C).

Preparation of polymer-bound thymidine-5-O-dithiodiphosphodiester (48a and 49a), uridine-5-O-dithiodiphosphodiester (48b and 49b), 3-azido-3-deoxythymidine-5-O-dithiodiphosphodiester (48c and 49c), adenosine-5-O-dithiodiphosphodiester (48d and 49d), α,β-D-mannose-6-O-dithiodiphosphodiester (48e and 49e), β-D-galactopyranose-6-O-dithiodiphosphodiester (48f and 49f), β-D-fructopyranose-1-O-dithiodiphosphodiester (48g and 49g), 6-O-(α-D-galactopyranosyl-6-O-diphosphodithiodiester)-α,β-D-glucose (48h and 49h)

To the swelled resins 40a-h (232-254 mg) or 41a-h (308-341 mg) in THF (3 mL) was added DBU (64 µL, 0.64 mmol). After 48 h shaking of the mixture at room temperature, the resins were collected by filtration and washed with THF (2×15 mL) and MeOH (2×15 mL), respectively, and were dried overnight at room temperature under vacuum to give 48a-h (226-244 mg) or 49a-h (302-224 mg). IR ($cm^{-1}$): 48a: 3251 (O—H), 1749 (C=O ester), 1642 (C=O, amide), 1029 (P—O—C); 48b: 3266 (O—H), 1750 (C=O ester), 1646 (C=O, amide), 1023 (P—O—C); 48c: 1752 (C=O ester), 1642 (C=O, amide), 1026 (P—O—C); 48d: 3279 (O—H), 1755 (C=O ester), 1639 (C=O, amide), 1029 (P—O—C); 48e: 3244 (O—H), 1761 (C=O ester), 1646 (C=O, amide), 1029 (P—O—C); 48f: 3235 (O—H), 1750 (C=O ester), 1646 (C=O, amide), 1025 (P—O—C); 48g: 3266 (O—H), 1753 (C=O ester), 1645 (C=O, amide), 1029 (P—O—C); 48h: 3249 (O—H), 1748 (C=O ester), 1644 (C=O, amide), 1026 (P—O—C); 49a: 3329 (O—H), 1759 (C=O ester), 1029 (P—O—C); 49b: 3324 (O—H), 1755 (C=O ester), 1019 (P—O—C); 49c: 1755 (C=O ester), 1021 (P—O—C); 49d: 3334 (O—H), 1757 (C=O ester), 1026 (P—O—C); 49e: 3247 (O—H), 1763 (C=O ester), 1018 (P—O—C); 49f: 3233 (O—H), 1755 (C=O ester), 1029 (P—O—C); 49g: 3240 (O—H), 1759 (C=O ester), 1029 (P—O—C); 49h: 3323 (O—H), 1755 (C=O ester), 1020 (P—O—C).

Preparation of thymidine-5-O-dithiodiphosphate (55a), uridine-5-O-dithiodiphosphate (55b), 3-azido-3-deoxythymidine-5-O-dithiodiphosphate (55c), adenosine-5-O-dithiodiphosphate (55d), α,β-D-mannose-6-O-dithiodiphosphate (55e), β-D-galactopyranose-6-O-dithiodiphosphate (55f), β-D-fructopyranose-1-O-dithiodiphosphate (55g), 6-O-(α-D-galactopyranosyl-6-O-dithiodiphosphate)-α,β-D-glucose (55h)

To the swelled resins 48a-h (226-244 mg) or 49a-h (302-224 mg) in anhydrous DCM (1 mL) was added DCM/TFA/water (24:74:2 v/v, 3 mL). After 25 min shaking of the mixtures at room temperature, the resins were collected by filtration and washed with DCM (2×10 mL), THF (2×5 mL), and MeOH (10 mL), respectively. The solvents of filtrate solutions were immediately evaporated at room temperature for 55a-d and at −20° C. for 55e-h, respectively. The residues were mixed with Amberlite AG-50W-X8 (100-200 mesh, hydrogen form, 500 mg, 1.7 meq/g) in water:dioxane (75:25 v/v, 3 mL) for 15 min at room temperature for 55a-d and at −20° C. for 55e-h, respectively. After filtration, the solvents were evaporated and the crude products were purified using $C_{18}$ Sep-Pak using appropriate solvents. The solvents were evaporated and the residues were dried under vacuum at −20° C. for 24 h to yield 55a-h. The purity and total isolated yields for 55a-h are shown in Table 4. The compounds were characterized by $^1H$ NMR, $^{13}C$ NMR, $^{31}P$ NMR, high resolution mass spectrometer (ESI-TOF), and phosphorous quantitative elemental analysis.

Thymidine-5-O-dithiodiphosphate (55a). $^1H$ NMR (DMSO-$d_6$): δ 1.75 (d, $J_{5-CH_3,6}$=1.1 Hz, 5-$CH_3$, 3H), 2.04-2.12 (m, H-2', H-2", 2H), 3.48-3.62 (m, H-5' and H-5", 2H), 3.70-3.82 (m, H-4', 1H), 4.21-4.30 (m, H-3', 1H), 4.90-5.02 (m, OH, 1H), 5.12-5.25 (m, OH, 1H), 6.15 (t, $J_{1',2'}$ and $J_{1',2''}$=6.8 Hz, H-1', 1H), 7.67 (d, $J_{6,5-CH_3}$=1.1 Hz, H-6, 1H), 11.16-11.21 (br s, N—H, 1H); $^{13}C$ NMR (DMSO-$d_6$): δ 13.06 (5-$CH_3$), 40.27 (C-2'), 62.14 (C-5'), 71.28 (C-3'), 84.65 (C-4'), 88.03 (C-1'), 110.25 (C-5), 136.97 (C-6), 151.30 (C-2 C=O), 164.64 (C-4 C=O); $^{31}P$ NMR (in DMSO-$d_6$ and $H_3PO_4$ 85% in water as external standard): δ 35.70 (s, α-P), 36.19 (s, β-P); HR-MS (ESI-TOF) (m/z) calcd. 433.9772, found 435.0159 [M+1]$^+$, Anal. Calcd. P 14.26%, found 14.60%.

Uridine-5-O-dithiodiphosphate (55b). $^1H$ NMR (DMSO-$d_6$): δ 3.50-3.66 (m, H-5' and H-5", 2H), 3.78-3.88 (m, H-4', 1H), 3.92-4.05 (m, H-3', 1H), 4.00-4.08 (m, H-2', 1H), 4.92-5.18 (br s, 2H, OH), 5.26-5.48 (br s, 1H, OH), 5.65 (d, $J_{5,6}$=8.0 Hz, H-5, 1H), 5.78 (d, $J_{1',2'}$=4.8 Hz, H-1', 1H), 7.87 (d, $J_{6,5}$=8.0 Hz, H-6, 1H), 10.80-11.60 (br s, N—H, 1H); $^{13}C$ NMR (DMSO-$d_6$): δ 61.67 (C-5'), 70.72 (C-2'), 74.42 (C-3'), 85.63 (C-4'), 88.56 (C-1'), 102.60 (C-5), 141.64 (C-6), 151.60 (C-2 C=O), 164.14 (C-4 C=O); $^{31}$P NMR (in DMSO-d$_6$ and H$_3$PO$_4$ 85% in water as external standard): δ 36.11 (s, α-P), 36.62 (s, β-P); HR-MS (ESI-TOF) (m/z) calcd. 435.9565, found, 436.9496 [M+H]$^+$; Anal. Calcd. P 14.20%, found 13.96%.

3'-Azido-3'-deoxythymidine-5-O-dithiodiphosphate (55c). $^1$H NMR (DMSO-d$_6$): δ 1.77 (d, $J_{5\text{-}CH_3,6}$=1.1 Hz, 5-CH$_3$, 3H), 2.22-2.31 (m, H-2', 1H), 2.32-2.42 (m, H-2", 1H), 3.55-3.70 (m, H-5' and H-5", 2H), 3.75-3.84 (m, H-4', 1H), 4.35-4.42 (m, H-3', 1H), 5.10-5.40 (br s, OH, 1H), 6.09 (t, $J_{1',2'}$=6.4 Hz, H-1', 1H), 7.67 (d, $J_{6,5\text{-}CH_3}$=1.1 Hz, H-6, 1H), 11.10-11.40 (br s, NH, 1H); $^{13}$C NMR (DMSO-d$_6$): δ 13.02 (5-CH$_3$), 37.12 (C-2'), 60.96 (C-3'), 61.61 (C-5'), 84.29 (C-4'), 84.86 (C-1'), 110.37 (C-5), 136.85 (C-6), 151.25 (C-2 C=O), 164.58 (C-4 C=O); $^{31}$P NMR (in DMSO-d$_6$ and H$_3$PO$_4$ 85% in water as external standard): δ 31.16 (s, α-P), 31.66 (s, β-P); HR-MS (ESI-TOF) (m/z) calcd. 458.9837, found 460.0065 [M+1]$^+$, Anal. Calcd. P 13.49%, found 13.21%.

Adenosine-5-O-dithiodiphosphate (55d). $^1$H NMR (DMSO-d$_6$): δ 3.53-3.67 (m, H-5', 1H), 3.69-3.77 (m, H-5", 1H), 4.01-4.07 (m, H-4', 1H), 4.18-4.26 (m, H-3', 1H), 4.68 (dd, $J_{2',1'}$=6.0, $J_{2',3'}$=5.6 Hz, H-2', 1H), 5.30-5.36 (m, OH, 1H), 5.50-5.63 (m, OH, 2H), 5.95 (d, $J_{1',2'}$=6.0 Hz, H-1', 1H), 7.45-7.54 (br s, 6-NH$_2$, 2H), 8.21 (s, H-2, 1H), 8.41 (s, H-8, 1H); $^{13}$C NMR (DMSO-d$_6$): δ 62.58 (C-5'); 71.62 (C-2'), 74.41 (C-3'), 86.86 (C-4'), 88.90 (C-1'), 120.23 (C-5), 140.98 (C-8), 149.88 (C-4), 153.31 (C-2), 157.00 (C-6); $^{31}$P NMR (in DMSO-d$_6$ and H$_3$PO$_4$ 85% in water as external standard): δ 40.07 (s, α-P), 40.57 (s, β-P); HR-MS (ESI-TOF) (m/z) calcd. 458.9837, found 460.0176 [M+1]$^+$, Anal. Calcd. P 13.49%, found 13.18%.

α,β-D-Mannose-6-O-dithiodiphosphate (55e). $^1$H NMR (DMSO-d$_6$): δ 2.96-3.05 (m, H-5β, 1H), 3.21-3.30 (m, H-4β, 1H), 3.30-3.39 (m, H-3β, H-4α, 2H), 3.40-3.47 (m, H-6α, 1H), 3.45-3.48 (m, H-6β, 1H), 3.48-3.51 (m, H-5α, 1H), 3.50-3.56 (H-6β, H-3α, H-6α, 3H), 3.56-3.65 (m, H-2α, H-2β, 2H), 4.35-4.42 (m, OH-4), 4.43-4.50 (m, OH-3), 4.50-4.56 (m, OH phosphate), 4.56-4.63 (m, H-1, 1H), 4.66-4.73 (m, OH-2), 4.82-4.88 (m, H-1α, 1H), 6.14 (d, $J_{1β,OH}$=8.0 Hz, OH-1β), 6.18 (d, $J_{1α,OH}$=4.0 Hz, OH-1α); $^{13}$C NMR (DMSO-d$_6$): δ 62.22 (C-6, α and β), 67.70 (C-4β), 68.02 (C-4α), 71.35 (C-3α), 72.08 (C-2α), 72.32 (C-3β), 73.77 (C-5α), 74.45 (C-2β), 77.67 (C-5β), 94.72 (C-1β), 94.81 (C—1α); $^{31}$P NMR (in DMSO-d$_6$ and H$_3$PO$_4$ 85% in water as external standard): δ 32.05 (s, α-P), 32.56 (s, β-P); HR-MS (ESI-TOF) (m/z) calcd. 371.9504, found 372.9236 [M+1]$^+$, Anal. Calcd. P 16.64%, found 16.51%.

β-D-Galactopyranose-6-O-dithiodiphosphate (55f). $^1$H NMR (DMSO-d$_6$): δ 3.28-3.42 (m, H-2, 1H), 3.42-3.51 (m, H-6 and H-3, 3H), 3.60-3.71 (m, H-5, 1H), 3.72-3.82 (m, H-4, 1H), 4.1-4.60 (br s, O—H), 4.80-4.92 (m, 1H, H-1), 6.07-6.20 (m, OH-1, 1H); $^{13}$C NMR (DMSO-d$_6$): δ 61.46 (C-6), 69.56 (C-4), 69.75 (C-2), 70.23 (C-3), 71.14 (C-5), 93.35 (C-1); $^{31}$P NMR (in DMSO-d$_6$ and H$_3$PO$_4$ 85% in water as external standard): δ 31.22 (s, αP), 31.73 (s, βP); HR-MS (ESI-TOF) (m/z) calcd. 371.9504, found 373.0114 [M+1]$^+$, Anal. Calcd. P 16.64%, found 16.77%.

β-D-Fructopyranose-1-O-dithiodiphosphate (55g). $^1$H NMR (DMSO-d$_6$): δ 3.25 (d, H-1b, $J_{1b,1a}$=11.6 Hz, 1H), 3.33-3.44 (m, H-1a, and H-6b, 2H), 3.47-3.59 (m, H-3 and H-5, 2H), 3.61-3.66 (m, H-4, 1H), 3.75 (d, H-6a, $J_{6a,6b}$=11.6 Hz, 1H), 4.29 (d, $J_{OH\text{-}5,5}$=6.0 Hz, OH-5, 1H), 4.38 (d, $J_{OH\text{-}4,4}$=3.6 Hz, OH-4, 1H), 4.46 (d, $J_{OH\text{-}3,3}$=4.8 Hz, OH-3, 1H), 4.48-4.54 (m, OH phosphate), 5.16 (s, OH-2, 1H); $^{13}$C NMR (DMSO-d$_6$): δ 63.84 (C-6), 65.12 (C-1), 68.56 (C-3), 69.96 (C-5), 70.69 (C-4), 98.84 (C-2); $^{31}$P NMR (in DMSO-d$_6$ and H$_3$PO$_4$ 85% in water as external standard): δ 31.12 (s, αP), 31.63 (s, βP); HR-MS (ESI-TOF) (m/z) calcd. 371.9504, found 372.9371 [M+1]$^+$, Anal. Calcd. P 16.64%, found 16.67%.

6-O-(α-D-Galactopyranosyl-6-O-dithiodiphosphate)-α,β-D-glucose (55h). $^1$H NMR (DMSO-d$_6$): δ 3.02-3.17 (m, H-2β, H-2α, H-4α, H-4β, H-3β, 5H), 3.36-3.49 (m, H-5β and H-3α, 2H), 3.50-3.56 (m, H-2', 1H), 3.58-3.63 (m, H-3', 1H), 3.64-3.70 (m, H-6α, H-6β, H-6', 6H), 3.70-3.74 (m, H-5', H-4', H-5α, 3H), 4.36-4.42 (m, OH-4'), 4.44-4.50 (m, OH-3α), 4.54-4.60 (OH-2β, OH-2α, OH-3β, OH-3', OH-2'), 4.60-4.68 (m, OH-4α, OH-4β), 4.78-4.83 (m, H-1', 1H), 4.86-4.91 (m, OH Phosphate), 4.90-4.95 (m, H-1β, 1H), 4.95-5.00 (m, H-1α, 1H), 6.27 (d, $J_{1αOH}$=4.0 Hz, OH-1α), 6.65 (d, $J_{1β,OH}$=6.4 Hz, OH-1β); $^{13}$C NMR (DMSO-d$_6$): δ 61.36 (C-6'), 67.71 (C-6β), 69.17 (C-6α), 69.61 (C-2'), 70.29 (C-4'), 70.99 (C-4β, C-3'), 71.42 (C-4α), 71.58 (C-5α), 72.88 (C-5', C-2α), 73.85 (C-3α), 75.43 (C-2β), 75.47 (C-5e), 77.32 (C-3β), 92.97 (C-1α), 97.52 (C-1β), 99.56, 99.62 (C-1', α, β respectively); $^{31}$P NMR (in DMSO-d$_6$ and H$_3$PO$_4$ 85% in water as external standard): δ 28.12 (s, αP), 28.63 (s, βP); HR-MS (ESI-TOF) (m/z) calcd. 534.0032, found 535.0187 [M+1]$^+$, Anal. Calcd. P 11.59%, found 11.74%.

Preparation of triphosphitylating reagent 2-cyanoethyl phosphoryl-O,O-bis(2-cyanoethyl diisopropylphosphoramidite) 27

Phosphorus trichloride (21, 2.63 mL, 30 mmol) and 3-hydroxypropionitrile (22, 2.06 mL, 30 mmol) were added to anhydrous CH$_3$CN (50 mL) under dry nitrogen. The mixture was stirred for 10 min at room temperature to yield 23. Two-thirds of the reaction mixture containing 23 was transferred to another reaction vessel at dry condition. Diisopropylamine (2.81 mL, 20 mmol) was added to the transferred reaction mixture and stirring was continued for 30 min under dry nitrogen to give 2-cyanoethyl diisopropylphosphoramidochloridite (24). Water (0.36 mL, 20 mmol) was added and the reaction mixture was stirred under nitrogen for 10 min to afford 25. The remaining reaction mixture containing 23 (0.5 eq) and the solution containing 25 (1 eq) were mixed and stirred for 45 min at room temperature to afford 2-cyanoethyl phosphoryl-O,O-bis(2-cyanoethyl diisopropylphosphoramidite) 27 (5.07 g, 94%). The reaction mixture containing triphosphitylating reagent 27 was immediately used in coupling reactions with polymer-bound p-acetoxybenzyl alcohol (31A) and polymer-bound N-Boc p-acetoxybenzyl alcohol (31B). Stability studies using HR-MS indicated that the compound remained stable even after two weeks storage at −20° C.

$^1$H NMR (DMSO-d$_6$): δ 0.91 (d, J=6.8 Hz, CH$_3$, 24H), 2.53 (dt, J=6.0 Hz, CH$_2$CN, 6H), 2.70-2.80 (m, CH, 4H), 3.53 (dt, J=6.0 Hz, CH$_2$O, 6H); $^{13}$C NMR (DMSO-d$_6$): δ 21.34, 23.84, 44.77, 56.80, 119.83, 120.33; $^{31}$P NMR (DMSO-d$_6$ and H$_3$PO$_4$ 85% in water as external standard): δ 116.73 (s, O—P—N), 131.73 (s, O—P—O); HR-MS (ESI-TOF) (m/z) calcd. 535.2207, found 535.1284 [M$^+$].

Solid-Phase Triphosphorylation Using Aminomethyl Polystyrene Resin Linked Through Amide Bond with p-Acetoxybenzyl Alcohol (31A) and Aminomethyl Polystyrene Resin Linked Through Reduced Amide Bond with p-Acetoxybenzyl Alcohol (31B)

Preparation of polymer-bound 2-cyanoethyl phosphoryl-O,O-bis(2-cyanoethyl diisopropylphosphoramidite) (33A and 33B)

The prepared reaction mixture containing 2-cyanoethyl phosphoryl-O,O-bis(2-cyanoethyl diisopropylphosphoramidite) 7 in CH$_3$CN (~10 mmol) as described above was added to a swelled solution of polymer-bound p-acetoxybenzyl alcohol 31A (3.05 g, 0.87 mmol/g) or polymer-bound N-Boc p-acetoxybenzyl alcohol 31B (3.75, 0.72 mmol/g) and 1H-tetrazole (531 mg, 7.5 mmol) in anhydrous THF (25 mL) and the mixture was shaken for 24 h at room temperature. The resin was collected by filtration, washed with CH$_3$CN (2×30 mL), THF (2×30 mL), and MeOH (2×30 mL), respectively, and was dried overnight under vacuum to give 33A (4.09 g, 91%, 0.59 mmol/g) or 33B (4.84 g, 96%, 0.53 mmol/g). IR (cm$^{-1}$): 33A: 2259 (CN), 1752 (C=O ester), 1650 (C=O, amide), 1026 (P—O—C); 33B: 2255 (CN), 1763 (C=O ester), 1029 (P—O—C).

Preparation of polymer-bound 5-O-[2-cyanoethyl phosphoryl-O,O-bis(2-cyanoethyl phosphite triester)]thymidine (36a and 37a), 5-O-[2-cyanoethyl phosphoryl-O,O-bis(2-cyanoethyl phosphosphite triester)]uridine (36b and 37b), 5-O-[2-cyanoethyl phosphoryl-O,O-bis(2-cyanoethyl phosphite triester)]-3-azido-3-deoxythymidine (36c and 37c), 5-O-[2-cyanoethyl phosphoryl-O,O-bis(2-cyanoethyl phosphite triester)]adenosine (36d and 37d), 6-O-[2-cyanoethyl phosphoryl-O,O-bis(2-cyanoethyl phosphite triester)]-α,β-D-mannose (36e and 37e), 6-O-[2-cyanoethyl phosphoryl-O,O-bis(2-cyanoethyl phosphite triester)]-β-D-galactopyranose (36f and 37f), 1-O-[2-cyanoethyl phosphoryl-O,O-bis(2-cyanoethyl phosphite triester)]-β-D-fructopyranose (36g and 37g), 6-O-[D-galactopyranosyl-6-O-(2-cyanoethyl phosphoryl-O,O-bis(2-cyanoethyl phosphite triester)]-α,β-D-glucose (36h and 37h)

Nucleosides and carbohydrates (a-h, 1.21 mmol) and 1H-tetrazole (68 mg, 0.96 mmol) were added to 33A (511 mg, 0.59 mmol/g) or 33B (605 mg, 0.53 mmol/g) in anhydrous THF (2 mL) and DMSO (2-3 mL) or in anhydrous DMSO (5 mL) in case of adenosine. The mixture was shaken for 28 h at room temperature. The resin was collected by filtration and washed with DMSO (3×20 mL), THF (2×15 mL), and MeOH (3×20 mL), respectively, and dried under vacuum to give 36a-h (528-571 mg) or 37a-h (622-671 mg). IR (cm$^{-1}$): 36a: 3353 (OH), 2267 (CN), 1763 (C=O ester), 1657 (C=O, amide), 1032 (P—O—C); 36b: 3328 (OH), 2265 (CN), 1763 (C=O ester), 1646 (C=O, amide), 1029 (P—O—C); 36c: 2262 (CN), 1755 (C=O ester), 1647 (C=O, amide), 1025 (P—O—C); 36d: 3313 (OH), 2262 (CN), 1763 (C=O ester), 1653 (C=O, amide), 1029 (P—O—C); 36e: 3324 (OH), 2260 (CN), 1762 (C=O ester), 1646 (C=O, amide), 1029 (P—O—C); 36f: 3317 (OH), 2265 (CN), 1755 (C=O ester), 1657 (C=O, amide), 1029 (P—O—C); 36g: 3295 (OH), 2258 (CN), 1766 (C=O ester), 1661 (C=O, amide), 1032 (P—O—C); 36h: 3335 (OH), 2258 (CN), 1763 (C=O ester), 1653 (C=O, amide), 1032 (P—O—C); 37a: 3342 (OH), 2257 (CN), 1766 (C=O ester), 1029 (P—O—C); 37b: 3332 (OH), 2153 (CN), 1759 (C=O ester), 1025 (P—O—C); 37c: 2258 (CN), 1759 (C=O ester), 1029 (P—O—C); 37d: 3335 (OH), 2259 (CN), 1763 (C=O ester), 1022 (P—O—C); 37e: 3335 (OH), 2265 (CN), 1755 (C=O ester), 1022 (P—O—C); 37f: 3339 (OH), 2262 (CN), 1759 (C=O ester), 1022 (P—O—C); 37g: 3324 (OH), 2257 (CN), 1766 (C=O ester), 1025 (P—O—C); 37h: 3309 (OH), 2250 (CN), 1758 (C=O ester), 1027 (P—O—C).

Oxidation of polymer-bound triphosphitylated precursors, 36a-h and 37a-h, to polymer-bound 5-O-[2-cyanoethyl phosphoryl-O,O-bis(2-cyanoethyl phosphate triester)]thymidine (42a and 43a), 5-O-[2-cyanoethyl phosphoryl-O,O-bis(2-cyanoethyl phosphate triester)]uridine (42b and 43b), 5-O-[2-cyanoethyl phosphoryl-O,O-bis(2-cyanoethyl phosphate triester)]-3-azido-3-deoxythymidine (42c and 43c), 5-O-[2-cyanoethyl phosphoryl-O,O-bis(2-cyanoethyl phosphate triester)]adenosine (42d and 43d), 6-O-[2-cyanoethyl phosphoryl-O,O-bis(2-cyanoethyl phosphate triester)]-α,β-D-mannose (42e and 43e), 6-O-[2-cyanoethyl phosphoryl-O,O-bis(2-cyanoethyl phosphate triester)]-β-D-galactopyranose (42f and 43f), 1-O-[2-cyanoethyl phosphoryl-O,O-bis(2-cyanoethyl phosphate triester)]-β-D-fructopyranose (42g and 43g), 6-O-[D-galactopyranosyl-6-O-(2-cyanoethyl phosphoryl-O,O-bis(2-cyanoethyl phosphate triester)]-α,β-D-glucose (42h and 43h)

tert-Butyl hydroperoxide in decane (5-6 M, 256 μL, 1.28 mmol for 36a-h; 5-6 M, 241 μL, 1.21 mmol for 47a-h) was added to the resins 36a-h, (264-286 mg) or 37a-h (311-335 mg) in THF (3 mL). After 1 h shaking at room temperature, the resins were collected by filtration and washed with THF (3×15 mL) and MeOH (3×15 mL), respectively, and were dried overnight at room temperature under vacuum to give 42a-h (266-297 mg) or 43a-h (317-354 mg). IR (cm$^{-1}$): 42a: 3341 (OH), 2258 (CN), 1751 (C=O ester), 1653 (C=O, amide), 1029 (P—O—C); 42b: 3347 (OH), 2257 (CN), 1764 (C=O ester), 1655 (C=O, amide), 1032 (P—O—C); 42c: 2263 (CN), 1760 (C=O ester), 1652 (C=O, amide), 1029 (P—O—C); 42d: 3345 (OH), 2267 (CN), 1759 (C=O ester), 1647 (C=O, amide), 1025 (P—O—C); 42e: 3327 (OH), 2258 (CN), 1757 (C=O ester), 1646 (C=O, amide), 1025 (P—O—C); 42f: 3292 (OH), 2260 (CN), 1761 (C=O ester), 1648 (C=O, amide), 1031 (P—O—C); 42g: 3307 (OH), 2259 (CN), 1751 (C=O ester), 1653 (C=O, amide), 1028 (P—O—C); 42h: 3324 (OH), 2264 (CN), 1757 (C=O ester), 1649 (C=O, amide), 1025 (P—O—C); 43a: 3377 (OH), 2264 (CN), 1756 (C=O ester), 1023 (P—O—C); 43b: 3356 (OH), 2265 (CN), 1763 (C=O ester), 1029 (P—O—C); 43c: 2252 (CN), 1760 (C=O ester), 1028 (P—O—C); 43d: 3349 (OH), 2251 (CN), 1768 (C=O ester), 1032 (P—O—C); 43e: 3276 (OH), 2248 (CN), 1765 (C=O ester), 1030 (P—O—C); 43f: 3289 (OH), 2262 (CN), 1758 (C=O ester), 1023 (P—O—C); 43g: 3327 (OH), 2253 (CN), 1764 (C=O ester), 1029 (P—O—C); 43h: 3351 (OH), 2262 (CN), 1762 (C=O ester), 1026 (P—O—C).

Preparation of polymer-bound thymidine-5-O-triphosphodiester (50a and 51a), uridine-5-O-triphosphodiester (50b and 51b), 3-azido-3-deoxythymidine-5-O-triphosphodiester (50c and 51c), adenosine-5-O-triphosphodiester (50d and 51d), α,β-D-mannose-6-O-triphosphodiester (50e and 51e), β-D-galactopyranose-6-O-triphosphodiester (50f and 51f), β-D-fructopyranose-1-O-triphosphodiester (50g and 51g), 6-O-(D-galactopyranosyl-6-O-triphosphodiester)-α,β-D-glucose (50h and 51h)

To the swelled resins 42a-h (266-297 mg) or 43a-h (317-354 mg) in THF (3 mL) was added DBU (64 μL, 0.64 mmol). After 48 h shaking of the mixture at room temperature, the resins were collected by filtration and washed with THF (2×15 mL) and MeOH (2×15 mL), respectively, and were dried overnight at room temperature under vacuum to give 50a-h (257-279 mg) or 51a-h (304-335 mg). IR (cm$^{-1}$): 50a: 3266 (O—H), 1755 (C=O ester), 1643 (C=O, amide), 1025 (P—O—C); 50b: 3265 (O—H), 1741 (C=O ester), 1646 (C=O, amide), 1025 (P—O—C); 50c: 1741 (C=O ester), 1641 (C=O, amide), 1029 (P—O—C); 50d: 3309 (O—H), 1748 (C=O ester), 1643 (C=O, amide), 1033 (P—O—C); 50e: 3284 (O—H), 1752 (C=O ester), 1643 (C=O, amide), 1025 (P—O—C); 50f: 3288 (O—H), 1759 (C=O ester), 1642 (C=O, amide), 1029 (P—O—C); 50g: 3273 (O—H), 1758 (C=O ester), 1646 (C=O, amide), 1025 (P—O—C); 50h: 3259 (O—H), 1753 (C=O ester), 1639 (C=O, amide), 1029 (P—O—C); 51a: 3303 (O—H), 1752 (C=O ester), 1025 (P—O—C); 51b: 3353 (O—H), 1755 (C=O ester), 1032 (P—O—C); 51c: 1763 (C=O ester), 1025 (P—O—C); 51d: 3357 (O—H), 1752 (C=O ester), 1026 (P—O—C); 51e: 3237 (O—H), 1748 (C=O ester), 1025 (P—O—C); 51f: 3287 (O—H), 1755 (C=O ester), 1029 (P—O—C); 51g: 3291 (O—H), 1755 (C=O ester), 1025 (P—O—C); 51h: 3302 (O—H), 1783 (C=O ester), 1029 (P—O—C).

Preparation of thymidine-5-O-triphosphate (56a), uridine-5-O-triphosphate (56b), AZT-5-O-triphosphate (56c), adenosine-5-O-triphosphate (56d), α,β-D-mannose-6-O-triphosphate (56e), β-D-galactopyranose-6-O-triphosphate (56f), β-D-fructopyranose-1-O-triphosphate (56g), 6-O-(α-D-galactopyranosyl-6-O-triphosphate)-α,β-D-glucose (56h)

To the swelled resins 50a-h (257-279 mg) or 51a-h (304-335 mg) in anhydrous DCM (1 mL) was added DCM/TFA/water (24:74:2 v/v, 3 mL). After 25 min shaking of the mixtures at room temperature, the resins were collected by filtration and washed with DCM (2×10 mL), THF (2×10 mL), and MeOH (10 mL), respectively. The solvents of filtrate solutions were immediately evaporated at room temperature for 56a-d and at −20° C. for 56e-h, respectively. The residues were mixed with Amberlite AG-50W-X8 (100-200 mesh, hydrogen form, 500 mg, 1.7 meq/g) in water:dioxane (75:25 v/v, 3 mL) for 15 min at room temperature for 56a-d and at −20° C. for 56e-h, respectively. After filtration, the solvents were evaporated and the crude products were purified using C$_{18}$ Sep-Pak using appropriate solvents. The solvents were evaporated and the residues were dried under vacuum at −20° C. for 24 h to yield 56a-h. The purity and total isolated yields for 56a-h are shown in Table 4. The compounds were characterized by $^1$H NMR, $^{13}$C NMR, $^{31}$P NMR, high resolution mass spectrometer (ESI-TOF), and phosphorous quantitative elemental analysis.

Thymidine-5-O-triphosphate (56a). $^1$H NMR (DMSO-d$_6$): δ 1.75 (d, $J_{5-CH_3,6}$=1.1 Hz, 5-CH$_3$, 3H), 2.04-2.12 (m, H-2' and H-2", 2H), 3.49-3.65 (m, H-5' and H-5", 2H), 3.70-3.82 (m, H-4', 1H), 4.21-4.30 (m, H-3', 1H), 4.92-5.03 (m, OH, 1H), 5.10-5.25 (m, OH, 1H), 6.15 (t, $J_{1',2'}$ and $J_{1',2'}$=6.8 Hz, H-1', 1H), 7.67 (d, $J_{6,5-CH_3}$=1.1 Hz, H-6, 1H), 11.16-11.22 (br s, N—H, 1H); $^{13}$C NMR (DMSO-d$_6$): δ 13.06 (5-CH$_3$), 40.27 (C-2'), 62.14 (C-5'), 71.28 (C-3'), 84.64 (C-4'), 88.03 (C-1'), 110.25 (C-5), 136.97 (C-6), 151.30 (C-2 C=O), 164.64 (C-4 C=O); $^{31}$P NMR (in DMSO-d$_6$ and H$_3$PO$_4$ 85% in water as external standard): δ −8.07 (s, β-P), 3.06 (s, α-P), 3.79 (s, γ-P); HR-MS (ESI-TOF) (m/z) calcd. 481.9893, found 483.0126 [M+H]$^+$. Anal. Calcd. P 19.27%, found 18.94%.

Uridine-5-O-triphosphate (56b). $^1$H NMR (DMSO-d$_6$): δ 3.50-3.69 (m, H-5' and H-5", 2H), 3.80-3.89 (m, H-4', 1H), 3.93-4.05 (m, H-3', 1H), 4.00-4.09 (m, H-2', 1H), 4.92-5.18 (br s, 2H, OH), 5.26-5.48 (br s, 1H, OH), 5.65 (d, $J_{5,6}$=8.0 Hz, H-5, 1H), 5.78 (d, $J_{1',2'}$=5.2 Hz, H-1', 1H), 7.87 (d, $J_{6,5}$=8.0 Hz, H-6, 1H), 10.60-11.56 (br s, N—H, 1H); $^{13}$C NMR (DMSO-d$_6$): δ 61.67 (C-5'), 70.72 (C-2'), 74.42 (C-3'), 85.63 (C-4'), 88.56 (C-1'), 102.60 (C-5), 141.64 (C-6), 151.60 (C-2 C=O), 164.15 (C-4 C=O); $^{31}$P NMR (in DMSO-d$_6$ and H$_3$PO$_4$ 85% in water as external standard): δ −6.99 (s, β-P), 4.12 (s, α-P), 4.77 (s, γ-P); HR-MS (ESI-TOF) (m/z) calcd. 483.9685, found 484.9735 [M+H]$^+$. Anal. Calcd. P 19.19%, found 19.25%.

3'-Azido-3'-deoxythymidine-5-O-triphosphate (56c). $^1$H NMR (DMSO-d$_6$): δ 1.77 (d, $J_{5-CH_3,6}$=1.1 Hz, 5-CH$_3$, 3H), 2.21-2.31 (m, H-2', 1H), 2.32-2.42 (m, H-2", 1H), 3.50-3.75 (m, H-5' and H-5", 2H), 3.77-3.80 (m, H-4', 1H), 4.33-4.44 (m, H-3', 1H), 5.10-5.60 (br s, OH, 1H), 6.09 (t, $J_{1',2'}$=6.4 Hz, H-1', 1H), 7.67 (d, $J_{6,5-CH_3}$=1.1 Hz, H-6, 1H), 11.20-11.40 (br s, NH, 1H); $^{13}$C NMR (DMSO-d$_6$): δ 13.02 (5-CH$_3$), 37.12 (C-2'), 60.96 (C-3'), 61.61 (C-5'), 84.29 (C-4'), 84.86 (C-1'), 110.37 (C-5), 136.85 (C-6), 151.25 (C-2 C=O), 164.58 (C-4 C=O); $^{31}$P NMR (in DMSO-d$_6$ and H$_3$PO$_4$ 85% in water as external standard): δ −7.78 (s, β-P), 3.12 (s, α-P), 3.88 (s, γ-P); HR-MS (ESI-TOF) (m/z) calcd. 506.9957, found 508.9792 [M+H]$^+$. Anal. Calcd. P 18.32%, found 18.19%.

Adenosine-5-O-triphosphate (56d). $^1$H NMR (DMSO-d$_6$): δ 3.52-3.63 (m, H-5', 1H), 3.63-3.76 (m, H-5", 1H), 3.95-4.05 (m, H-4', 1H), 4.15-4.25 (m, H-3', 1H), 4.65 (dd, $J_{2',1'}$=6.4, $J_{2',3'}$=5.5 Hz, H-2', 1H), 5.22-5.30 (m, OH, 1H), 5.42-5.56 (m, OH, 2H), 5.91 (d, $J_{1',2'}$=6.4 Hz, H-1', 1H), 7.35-7.48 (br s, 6-NH$_2$, 2H), 8.17 (s, H-2, 1H), 8.38 (s, H-8, 1H); $^{13}$C NMR (DMSO-d$_6$): δ 62.46 (C-5'); 71.50 (C-2'), 74.28 (C-3'), 86.72 (C-4'), 88.77 C-1'), 120.06 (C-5), 140.80 (C-8), 149.69 (C-4), 153.11 (C-2), 156.80 (C-6); $^{31}$P NMR (in DMSO-d$_6$ and H$_3$PO$_4$ 85% in water as external standard): δ −6.48 (s, β-P), 4.75 (s, α-P), 5.38 (s, γ-P); HR-MS (ESI-TOF) (m/z) calcd. 506.9957, found 508.0137 [M+H]$^+$. Anal. Calcd. P 18.32%, found 18.21%.

α,β-D-Mannose-6-O-triphosphate (56e). $^1$H NMR (DMSO-d$_6$): δ 2.96-3.04 (m, H-5β, 1H), 3.21-3.29 (m, H-4β, 1H), 3.30-3.39 (m, H-3β, H-4α, 2H), 3.40-3.47 (m, H-6α, 1H), 3.45-3.48 (m, H-6β, 1H), 3.48-3.51 (m, H-5α, 1H), 3.50-3.56 (H-6β, H-3α, H-6α, 3H), 3.56-3.65 (m, H-2α, H-2β, 2H), 4.35-4.43 (m, OH-4), 4.44-4.50 (m, OH-3), 4.50-4.56 (m, OH phosphate), 4.56-4.63 (m, H-1β, 1H), 4.66-4.73 (m, OH-2), 4.82-4.88 (m, H-1α, 1H), 6.14 (d, $J_{1β,OH}$=8.4 Hz, OH-1β), 6.19 (d, $J_{1α,OH}$=4.0 Hz, OH-1α); $^{13}$C NMR (DMSO-d$_6$): δ 62.22 (C-6, α and β), 67.70 (C-4β), 68.02 (C-4α), 71.35 (C-3α), 72.08 (C-2α), 72.32 (C-3β), 73.77 (C-5α), 74.45 (C-2β), 77.67 (C-5β), 94.72 (C-1β), 94.81 (C-1α); $^{31}$P NMR (in DMSO-d$_6$ and H$_3$PO$_4$ 85% in water as external standard): δ −7.92 (s, β-P), 3.22 (s, α-P), 3.85 (s, γ-P); HR-MS (ESI-TOF) (m/z) calcd. 419.9624, found 420.9708 [M+H]$^+$. Anal. Calcd. P 22.12%, found 22.26%.

β-D-Galactopyranose-6-O-triphosphate (56f). $^1$H NMR (DMSO-d$_6$): δ 3.28-3.42 (m, H-2, 1H), 3.42-3.51 (m, H-6 and H-3, 3H), 3.60-3.71 (m, H-5, 1H), 3.72-3.82 (m, H-4, 1H), 4.1-4.65 (br s, O—H), 4.83-4.92 (m, 1H, H-1), 6.02-6.20 (m, OH-1, 1H); $^{13}$C NMR (DMSO-d$_6$): δ 61.46 (C-6), 69.56 (C-4), 69.75 (C-2), 70.23 (C-3), 71.14 (C-5), 93.34 (C-1); $^{31}$P NMR (in DMSO-d$_6$ and H$_3$PO$_4$ 85% in water as external standard): δ −8.67 (s, β-P), 2.51 (s, α-P), 3.11 (s, γ-P); HR-MS (ESI-TOF) (m/z) calcd. 419.9624, found 421.0076 [M+H]$^+$. Anal. Calcd. P 22.12%, found 21.90%.

β-D-Fructopyranose-1-O-triphosphate (56g). $^1$H NMR (DMSO-d$_6$): δ 3.25 (d, H-1b, $J_{1b,1a}$=11.6 Hz, 1H), 3.34-3.44 (m, H-1a, and H-6b, 2H), 3.48-3.59 (m, H-3 and H-5, 2H), 3.61-3.68 (m, H-4, 1H), 3.75 (d, H-6a, $J_{6a,6b}$=11.6 Hz, 1H), 4.29 (d, $J_{OH-5,5}$=6.0 Hz, OH-5, 1H), 4.38 (d, $J_{OH-4,4}$=3.6 Hz, OH-4, 1H), 4.46 (d, $J_{OH-3,3}$=4.8 Hz, OH-3, 1H), 4.48-4.54 (m, OH phosphate), 5.16 (s, OH-2, 1H); $^{13}$C NMR (DMSO-d$_6$): δ 63.84 (C-6), 65.12 (C-1), 68.56 (C-3), 69.96 (C-5), 70.69 (C-4), 98.84 (C-2); $^{31}$P NMR (in DMSO-$d_6$ and $H_3PO_4$ 85% in water as external standard): δ −8.79 (s, β-P), 2.39 (s, α-P), 2.98 (s, γ-P); HR-MS (ESI-TOF) (m/z) calcd. 419.9624, found 421.0013 [M+H]$^+$. Anal. Calcd. P 22.12%, found 22.35%.

6-O-(α-D-Galactopyranosyl-6-O-triphosphate)-α,β-D-glucose (56h). $^1$H NMR (DMSO-$d_6$): δ 3.02-3.16 (m, H-2β, H-2α, H-4α, H-4β, H-3β, 5H), 3.36-3.49 (m, H-5β and H-3α, 2H), 3.50-3.56 (m, H-2', 1H), 3.58-3.63 (m, H-3', 1H), 3.64-3.70 (m, H-6α, H-6β, H-6', 6H), 3.70-3.74 (m, H-5', H-4', H-5α, 3H), 4.35-4.42 (m, OH-4'), 4.44-4.50 (m, OH-3α), 4.54-4.60 (OH-2β, OH-2α, OH-3β, OH-3', OH-2'), 4.60-4.68 (m, OH-4α, OH-4β), 4.78-4.83 (m, H-1', 1H), 4.86-4.91 (m, OH Phosphate), 4.91-4.95 (m, H-1β, 1H), 4.95-5.02 (m, H-1α, 1H), 6.26 (d, $J_{1\alpha,OH}$=4.0 Hz, OH-1α), 6.65 (d, $J_{1\beta,OH}$=6.4 Hz, OH-1β); $^{13}$C NMR (DMSO-$d_6$): δ 61.36 (C-6'), 67.71 (C-6β), 69.17 (C-6α), 69.61 (C-2'), 70.29 (C-4'), 70.99 (C-4β, C-3'), 71.42 (C-4α), 71.58 (C-5α), 72.88 (C-5', C-2α), 73.85 (C-3α), 75.43 (C-2β), 75.47 (C-5β), 77.31 (C-3β), 92.97 (C-1α), 97.52 (C-1β), 99.56, (C-1', α, and β); $^{31}$P NMR (in DMSO-$d_6$ and $H_3PO_4$ 85% in water as external standard): δ −9.10 (s, β-P), 2.02 (s, α-P), 2.67 (s, γ-P); HR-MS (ESI-TOF) (m/z) calcd. 582.0152, found 583.0465 [M+H]$^+$. Anal. Calcd. P 15.96%, found 16.23%.

Solid-Phase Trithiotriphosphorylation Using Aminomethyl Polystyrene Resin Linked Through Amide Bond with p-Acetoxybenzyl Alcohol (31A) and Aminomethyl Polystyrene Resin Linked Through Reduced Amide Bond with p-Acetoxybenzyl Alcohol (31B)

> Sulfurization of polymer-bound triphosphitylated precursors, 36a-h and 37a-h, to polymer-bound 5-O-[2-cyanoethyl phosphoryl-O,O-bis(2-cyanoethyl thiophosphate triester)]thymidine (44a and 45a), 5-O-[2-cyanoethyl phosphoryl-O,O-bis(2-cyanoethyl thiophosphate triester)]uridine (44b and 45b), 5-O-[2-cyanoethyl phosphoryl-O,O-bis(2-cyanoethyl thiophosphate triester)]-3-azido-3-deoxythymidine (44c and 45c), 5-O-[2-cyanoethyl phosphoryl-O,O-bis(2-cyanoethyl thiophosphate triester)]adenosine (44d and 45d), 6-O-[2-cyanoethyl phosphoryl-O,O-bis(2-cyanoethyl thiophosphate triester)]-α,β-D-mannose (44e and 45e), 6-O-[2-cyanoethyl phosphoryl-O,O-bis(2-cyanoethyl thiophosphate triester)]-β-D-galactopyranose (44f and 45f), 1-O-[2-cyanoethyl phosphoryl-O,O-bis(2-cyanoethyl thiophosphate triester)]-β-D-fructopyranose (44g and 45g), 6-O-[α-D-galactopyranosyl-6-O-(2-cyanoethyl phosphoryl-O,O-bis(2-cyanoethyl thiophosphate triester)]-α,β-D-glucose (44h and 45h)

Beaucage's reagent (3H-1,2-benzotrithiole-3-one 1,1-dioxide) (241 mg, 1.21 mmol for 36a-h; 256 mg, 1.28 mmol for 37a-h) was added to the resins 36a-h (264-286 mg) or 37a-h (311-335 mg) in $CH_3CN$ (5 mL). After 6 h shaking at 40° C., the resins were collected by filtration and washed with $CH_3CN$ (2×15 mL), THF (2×15 mL), and MeOH (3×15 mL), respectively, and were dried under vacuum to give 44a-h (277-302 mg) or 45a-h (327-363 mg). IR (cm$^{-1}$): 44a: 3332 (OH), 2259 (CN), 1763 (C=O ester), 1651 (C=O, amide), 1025 (P—O—C); 44b: 3347 (OH), 2261 (CN), 1766 (C=O ester), 1646 (C=O, amide), 1028 (P—O—C); 44c: 2263 (CN), 1758 (C=O ester), 1648 (C=O, amide), 1025 (P—O—C); 44d: 3323 (OH), 2258 (CN), 1767 (C=O ester), 1647 (C=O, amide), 1029 (P—O—C); 44e: 3289 (OH), 2252 (CN), 1755 (C=O ester), 1643 (C=O, amide), 1026 (P—O—C); 44f: 3287 (OH), 2250 (CN), 1757 (C=O ester), 1651 (C=O, amide), 1028 (P—O—C); 44g: 3301 (OH), 2267 (CN), 1764 (C=O ester), 1656 (C=O, amide), 1032 (P—O—C); 44h: 3294 (OH), 2257 (CN), 1768 (C=O ester), 1659 (C=O, amide), 1024 (P—O—C); 45a: 3322 (OH), 2257 (CN), 1761 (C=O ester), 1029 (P—O—C); 45b: 3367 (OH), 2262 (CN), 1766 (C=O ester), 1025 (P—O—C); 45c: 2254 (CN), 1758 (C=O ester), 1026 (P—O—C); 45d: 3370 (OH), 2252 (CN), 1760 (C=O ester), 1025 (P—O—C); 45e: 3245 (OH), 2261 (CN), 1757 (C=O ester), 1023 (P—O—C); 45f: 3312 (OH), 2249 (CN), 1767 (C=O ester), 1029 (P—O—C); 45g: 3295 (OH), 2250 (CN), 1766 (C=O ester), 1024 (P—O—C); 45h: 3317 (OH), 2252 (CN), 1756 (C=O ester), 1029 (P—O—C).

> Preparation of polymer-bound thymidine-5-O-trithiotriphosphodiester (52a and 53a), uridine-5-O-trithiotriphosphodiester (52b and 53b), 3-azido-3-deoxythymidine-5-O-trithiotriphosphodiester (52c and 53c), adenosine-5-O-trithiotriphosphodiester (52d and 53d), α,β-D-mannose-6-O-trithiotriphosphodiester (52e and 53e), β-D-galactopyranose-6-O-trithiotriphosphodiester (52f and 53f), β-D-fructopyranose-1-O-trithiotriphosphodiester (52g and 53g), 6-O-(α-D-galactopyranosyl-6-O-trithiotriphosphodiester)-α,β-D-glucose (52h and 53h)

To the swelled resins 44a-h (277-302 mg) or 45a-h (327-363 mg) in THF (3 mL) was added DBU (64 μL, 0.64 mmol). After 48 h shaking of the mixture at room temperature, the resins were collected by filtration and washed with THF (2×15 mL) and MeOH (2×15 mL), respectively, and were dried overnight at room temperature under vacuum to give 52a-h (273-292 mg) or 53a-h (218-239 mg). IR (cm$^{-1}$): 52a: 3252 (O—H), 1745 (C=O ester), 1643 (C=O, amide), 1025 (P—O—C); 52b: 3252 (O—H), 1741 (C=O ester), 1639 (C=O, amide), 1025 (P—O—C); 52c: 1741 (C=O ester), 1643 (C=O, amide), 1029 (P—O—C); 52d: 3244 (O—H), 1749 (C=O ester), 1642 (C=O, amide), 1029 (P—O—C); 52e: 3237 (O—H), 1751 (C=O ester), 1646 (C=O, amide), 1025 (P—O—C); 52f: 3244 (O—H), 1752 (C=O ester), 1643 (C=O, amide), 1025 (P—O—C); 52g: 3241 (O—H), 1745 (C=O ester), 1647 (C=O, amide), 1025 (P—O—C); 52h: 3252 (O—H), 1748 (C=O ester), 1646 (C=O, amide), 1025 (P—O—C); 53a: 3346 (O—H), 1759 (C=O ester), 1025 (P—O—C); 53b: 3356 (O—H), 1756 (C=O ester), 1025 (P—O—C); 53c: 1762 (C=O ester), 1023 (P—O—C); 53d: 3334 (O—H), 1759 (C=O ester), 1025 (P—O—C); 53e: 3248 (O—H), 1756 (C=O ester), 1025 (P—O—C); 53f: 3252 (O—H), 1755 (C=O ester), 1029 (P—O—C); 53g: 3266 (O—H), 1755 (C=O ester), 1018 (P—O—C); 53h: 3302 (O—H), 1763 (C=O ester), 1032 (P—O—C).

> Preparation of thymidine-5-O-trithiotriphosphate (57a), uridine-5-O-trithiotriphosphate (57b), 3-azido-3-deoxythymidine-5-O-trithiotriphosphate (57c), adenosine-5-O-trithiotriphosphate (57d), α,β-D-mannose-6-O-trithiotriphosphate (57e), β-D-galactopyranose-6-O-trithiotriphosphate (57f), β-D-fructopyranose-1-O-trithiotriphosphate (57g), 6-O-(α-D-galactopyranosyl-6-O-trithiotriphosphate)-α,β-D-glucose (57h)

To the swelled resins 52a-h (273-292 mg) or 53a-h (218-239 mg) in anhydrous DCM (1 mL) was added DCM/TFA/water (24:74:2 v/v, 3 mL). After 25 min shaking of the mixtures at room temperature, the resins were collected by filtration and washed with DCM (2×10 mL), THF (2×5 mL), and MeOH (10 mL), respectively. The solvents of filtrate solutions were immediately evaporated at room temperature for 57a-d and at −20° C. for 57e-h, respectively. The residues were mixed with Amberlite AG-50W-X8 (100-200 mesh, hydrogen form, 500 mg, 1.7 meq/g) in water:dioxane (75:25 v/v, 3 mL) for 15 min at room temperature for 57a-d and at −20° C. for 57e-h, respectively. After filtration, the solvents were evaporated and the crude products were purified using $C_{18}$ Sep-Pak using appropriate solvents. The solvents were evaporated and the residues were dried under vacuum at −20° C. for 24 h to yield 57a-h. The purity and total isolated yields for 57a-h are shown in Table 4. The compounds were characterized by $^1$H NMR, $^{13}$C NMR, $^{31}$P NMR, high resolution mass spectrometer (ESI-TOF), and phosphorous quantitative elemental analysis.

Thymidine-5-O-trithiotriphosphate (57a). $^1$H NMR (DMSO-$d_6$): δ 1.75 (d, $J_{5\text{-}CH_3,6}$=1.1 Hz, 5-$CH_3$, 3H), 2.04-2.12 (m, H-2' and H-2", 2H), 3.49-3.65 (m, H-5' and H-5", 2H), 3.70-3.82 (m, H-4', 1H), 4.21-4.30 (m, H-3', 1H), 4.92-5.05 (m, OH, 1H), 5.10-5.25 (m, OH, 1H), 6.15 (t, $J_{1',2'}$ and $J_{1',2''}$=6.8 Hz, H-1', 1H), 7.67 (d, $J_{6,5\text{-}CH_3}$=1.1 Hz, H-6, 1H), 11.12-11.22 (br s, N—H, 1H); $^{13}$C NMR (DMSO-$d_6$): δ 13.06 (5-$CH_3$), 40.27 (C-2'), 62.14 (C-5'), 71.28 (C-3'), 84.65 (C-4'), 88.03 (C-1'), 110.25 (C-5), 136.97 (C-6), 151.30 (C-2 C=O), 164.64 (C-4 C=O); $^{31}$P NMR (in DMSO-$d_6$ and $H_3PO_4$ 85% in water as external standard): δ 24.19 (s, β-P), 35.38 (s, α-P), 35.96 (s, γ-P); HR-MS (ESI-TOF) (m/z) calcd. 529.9207, found 530.9176 [M+1]$^+$, Anal. Calcd. P 17.52%, found 17.63%.

Uridine-5-O-trithiotriphosphate (57b). $^1$H NMR (DMSO-$d_6$): δ 3.48-3.65 (m, H-5' and H-5", 2H), 3.82-3.90 (m, H-4', 1H), 3.94-4.03 (m, H-3', 1H), 4.04-4.09 (m, H-2', 1H), 4.80-5.20 (br s, 2H, OH), 5.20-5.50 (br s, 1H, OH), 5.65 (d, $J_{5,6}$=8.0 Hz, H-5, 1H), 5.78 (d, $J_{1',2'}$=5.2 Hz, H-1', 1H), 7.87 (d, $J_{6,5}$=8.0 Hz, H-6, 1H), 10.20-11.70 (br s, N—H, 1H); $^{13}$C NMR (DMSO-$d_6$): δ 61.67 (C-5'), 70.72 (C-2'), 74.42 (C-3'), 85.63 (C-4'), 88.56 (C-1'), 102.60 (C-5), 141.64 (C-6), 151.59 (C-2 C=O), 164.15 (C-4 C=O); $^{31}$P NMR (in DMSO-$d_6$ and $H_3PO_4$ 85% in water as external standard): δ 27.22 (s, β-P), 38.49 (s, α-P), 39.09 (s, γ-P); HR-MS (ESI-TOF) (m/z) calcd. 531.9000, found 532.8997 [M+1]$^+$, Anal. Calcd. P 17.46%, found 17.71%.

3'-Azido-3'-deoxythymidine-5-O-trithiotriphosphate (57c). $^1$H NMR (DMSO-$d_6$): δ 1.77 (d, $J_{5\text{-}CH_3,6}$=1.1 Hz, 5-$CH_3$, 3H), 2.21-2.31 (m, H-2', 1H), 2.32-2.42 (m, H-2", 1H), 3.50-3.72 (m, H-5' and H-5", 2H), 3.77-3.79 (m, H-4', 1H), 4.34-4.43 (m, H-3', 1H), 5.10-5.40 (br s, OH, 1H), 6.09 (t, $J_{1',2'}$=6.4 Hz, H-1', 1H), 7.67 (d, $J_{6,5\text{-}CH_3}$=1.1 Hz, H-6, 1H), 11.15-11.35 (br s, NH, 1H); $^{13}$C NMR (DMSO-$d_6$): δ 13.02 (5-$CH_3$), 37.12 (C-2'), 60.96 (C-3'), 61.60 (C-5'), 84.29 (C-4'), 84.86 (C-1'), 110.37 (C-5), 136.85 (C-6), 151.25 (C-2 C=O), 164.58 (C-4 C=O); $^{31}$P NMR (in DMSO-$d_6$ and $H_3PO_4$ 85% in water as external standard): δ 32.10 (s, β-P), 43.23 (s, α-P), 43.96 (s, γ-P); HR-MS (ESI-TOF) (m/z) calcd. 554.9272, found 555.9203 [M+1]$^+$, Anal. Calcd. P 16.73%, found 17.07%.

Adenosine-5-O-trithiotriphosphate (57d). $^1$H NMR (DMSO-$d_6$): δ 3.52-3.66 (m, H-5', 1H), 3.67-3.80 (m, H-5", 1H), 4.01-4.06 (m, H-4', 1H), 4.15-4.28 (m, H-3', 1H), 4.68 (dd, $J_{2',1'}$=6.0, $J_{2',3'}$=5.5 Hz, H-2', 1H), 5.29-5.38 (m, OH, 1H), 5.52-5.64 (m, OH, 2H), 5.95 (d, $J_{1',2'}$=6.0 Hz, H-1', 1H), 7.40-7.53 (br s, 6-$NH_2$, 2H), 8.21 (s, H-2, 1H), 8.41 (s, H-8, 1H); $^{13}$C NMR (DMSO-$d_6$): δ 62.58 (C-5'); 71.62 (C-2'), 74.41 (C-3'), 86.86 (C-4'), 88.90 (C-1'), 120.23 (C-5), 140.98 (C-8), 149.88 (C-4), 153.31 (C-2), 157.00 (C-6); $^{31}$P NMR (in DMSO-$d_6$ and $H_3PO_4$ 85% in water as external standard): δ 30.87 (s, β-P), 42.00 (s, α-P), 42.74 (s, γ-P); HR-MS (ESI-TOF) (m/z) calcd. 554.9272, found 555.9371 [M+1]$^+$, Anal. Calcd. P 16.73%, found 16.69%.

α,β-D-Mannose-6-O-trithiotriphosphate (57e). $^1$H NMR (DMSO-$d_6$): δ 2.95-3.04 (m, H-5β, 1H), 3.21-3.29 (m, H-4β, 1H), 3.30-3.39 (m, H-3β, H-4α, 2H), 3.40-3.47 (m, H-6α, 1H), 3.45-3.48 (m, H-6β, 1H), 3.48-3.51 (m, H-5α, 1H), 3.50-3.56 (H-6β, H-3α, H-6α, 3H), 3.56-3.65 (m, H-2α, H-2β, 2H), 4.36-4.43 (m, OH-4), 4.44-4.50 (m, OH-3), 4.50-4.56 (m, OH phosphate), 4.56-4.63 (m, H-1β, 1H), 4.65-4.74 (m, OH-2), 4.83-4.89 (m, H-1α, 1H), 6.14 (d, $J_{1\beta,OH}$=8.0 Hz, OH-1β), 6.19 (d, $J_{1\alpha,OH}$=4.0 Hz, OH-1α); $^{13}$C NMR (DMSO-$d_6$): δ 62.22 (C-6, α and β), 67.70 (C-4β), 68.02 (C-4α), 71.35 (C-3α), 72.08 (C-2α), 72.32 (C-3β), 73.77 (C-5α), 74.45 (C-2β), 77.66 (C-5β), 94.72 (C-1β), 94.81 (C-1α); $^{31}$P NMR (in DMSO-$d_6$ and $H_3PO_4$ 85% in water as external standard): δ 23.12 (s, β-P), 34.27 (s, α-P), 35.00 (s, γ-P); HR-MS (ESI-TOF) (m/z) calcd. 467.8938, found 467.9103[M+1]$^+$, Anal. Calcd. P 19.84%, found 19.68%.

β-D-Galactopyranose-6-O-trithiotriphosphate (57f). $^1$H NMR (DMSO-$d_6$): δ 3.28-3.42 (m, H-2, 1H), 3.42-3.53 (m, H-6 and H-3, 3H), 3.60-3.71 (m, H-5, 1H), 3.72-3.82 (m, H-4, 1H), 4.1-4.62 (br s, O—H), 4.80-4.92 (m, 1H, H-1), 6.07-6.20 (m, OH-1, 1H); $^{13}$C NMR (DMSO-$d_6$): δ 61.46 (C-6), 69.56 (C-4), 69.75 (C-2), 70.24 (C-3), 71.14 (C-5), 93.35 (C-1); $^{31}$P NMR (in DMSO-$d_6$ and $H_3PO_4$ 85% in water as external standard): δ 19.50 (s, β-P), 29.90 (s, α-P), 30.63 (s, γ-P); HR-MS (ESI-TOF) (m/z) calcd. 467.8938, found 468.8891 [M+1]$^+$, Anal. Calcd. P 19.84%, found 20.13%.

β-D-Fructopyranose-1-O-trithiotriphosphate (57g). $^1$H NMR (DMSO-$d_6$): δ 3.25 (d, H-1b, $J_{1b,1a}$=11.6 Hz, 1H), 3.34-3.45 (m, H-1a, and H-6b, 2H), 3.47-3.59 (m, H-3 and H-5, 2H), 3.61-3.66 (m, H-4, 1H), 3.75 (d, H-6a, $J_{6a,6b}$=11.6 Hz, 1H), 4.29 (d, $J_{OH\text{-}5,5}$=5.2 Hz, OH-5, 1H), 4.37 (d, $J_{OH\text{-}4,4}$=2.4 Hz, OH-4, 1H), 4.46 (d, $J_{OH\text{-}3,3}$=4.8 Hz, OH-3, 1H), 4.48-4.54 (m, OH phosphate), 5.16 (s, OH-2, 1H); $^{13}$C NMR (DMSO-$d_6$): δ 63.84 (C-6), 65.12 (C-4), 68.56 (C-3), 69.97 (C-2), 70.69 (C-5), 98.84 (C-1); $^{31}$P NMR (in DMSO-$d_6$ and $H_3PO_4$ 85% in water as external standard): δ 21.99 (s, β-P), 33.12 (s, α-P), 33.85 (s, γ-P); HR-MS (ESI-TOF) (m/z) calcd. 467.8938, found 468.8907 [M+1]$^+$, Anal. Calcd. P 19.84%, found 20.24%.

6-O-(α-D-Galactopyranosyl-6-O-trithiotriphosphate)-α,β-D-glucose (57h). $^1$H NMR (DMSO-$d_6$): δ 3.01-3.16 (m, H-2β, H-2α, H-4α, H-4β, H-3β, 5H), 3.34-3.49 (m, H-5β and H-360, 2H), 3.50-3.56 (m, H-2', 1H), 3.58-3.63 (m, H-3', 1H), 3.64-3.70 (m, H-6α, H-6β, H-6', 6H), 3.70-3.74 (m, H-5', H-4', H-5α, 3H), 4.34-4.42 (m, OH-4'), 4.44-4.50 (m, OH-3α), 4.54-4.60 (OH-2β, OH-2α, OH-3β, OH-3', OH-2'), 4.60-4.68 (m, OH-4α, OH-4β), 4.78-4.83 (m, H-1', 1H), 4.86-4.91 (m, OH Phosphate), 4.91-4.95 (m, H-1β, 1H), 4.95-5.02 (m, H-1α, 1H), 6.27 (d, $J_{1\alpha OH}$=4.0 Hz, OH-1α), 6.65 (d, $J_{1\beta,OH}$=6.4 Hz, OH-1β); $^{13}$C NMR (DMSO-$d_6$): δ 61.36 (C-6'), 67.71 (C-6β), 69.17 (C-6α), 69.60 (C-2'), 70.29 (C-4'), 70.99 (C-4β, C-3'), 71.42 (C-4α), 71.58 (C-5α), 72.88 (C-5', C-2α), 73.85 (C-3α), 75.43 (C-2β), 75.44 (C-5β), 77.31 (C-3β), 92.97 (C-1α), 97.52 (C-1β), 99.56, (C-1', α, and β); $^{31}$P NMR (in DMSO-$d_6$ and $H_3PO_4$ 85% in water as external standard): δ 18.08 (s, β-P), 29.22 (s, α-P), 29.95 (s, γ-P); HR-MS (ESI-TOF) (m/z) calcd. 629.9467, found 631.5219 [M+1]$^+$, Anal. Calcd. P 14.74%, found 14.96%.

Preparation of O—[(O,O-bis(2-cyanoethyl)phosphoryl]-O-[2-cyanoethyl phosphorochloridite]diisopropylaminophosphoramidite (30)

In the first reaction vessel phosphorus trichloride (21, 875 µL, 10 mmol), triethylamine (1.4 mL, 10 mmol), and 3-hydroxypropionitrile (22, 683 µL, 10 mmol) were added to anhydrous THF (25 mL) under dry nitrogen. The mixture was stirred for 10 min at room temperature to yield 2-cyanoethyl phosphorodichloridite (23).

In the second reaction vessel 3-hydroxypropionitrile (20 mmol) and triethylamine (2.8 mL, 20 mmol) were added to a solution of phosphorus trichloride (10 mmol) in THF (25 mL) under dry nitrogen. The mixture was stirred for 10 min at room temperature to give bis(2-cyanoethyl) phosphorochloridite (28).

In third reaction vessel phosphorus trichloride (10 mmol), triethylamine (1.4 mL, 10 mmol), and diisopropylamine (1.4 mL, 10 mmol) were added to the anhydrous THF (25 mL) under dry nitrogen. The mixture was stirred for 30 min at room temperature to yield diisopropylphosphoramidodichloridite (29). Then water (360 µL, 20 mmol) was added dropwise to 29 in 10 min period along with stirring to give 30.

The reaction mixtures in reaction vessels 2 and 3 containing 28 and 30, respectively, were mixed together. Triethylamine (1.4 mL, 10 mmol) was added to the mixture and the resulting mixture was stirred for 20 min under dry nitrogen to yield 29. Triethylamine (1.4 mL, 10 mmol) and the first reaction mixture containing 23 were added to 29. Stirring was continued under dry condition for 25 min at room temperature to afford 30 (4.29 g, 91%). The reaction mixture containing β-triphosphitylating reagent 30 was immediately used in coupling reactions with polymer-bound N-Boc p-acetoxybenzyl alcohol 31B. Further stability studies on 30 using NMR and mass spectrometry methods showed that the compound remained stable after 2 months storage at −20° C.

$^1$H NMR (DMSO-$d_6$, 400 MHz, δ ppm): 0.92 (d, J=8.0 Hz, 12H), 2.55 (t, J=6.0 Hz, 6H), 2.61-2.83 (Heptet, J=8.0 Hz, 2H), 3.57 (t, J=6.0 Hz, 6H); $^{13}$C NMR (DMSO-$d_6$, 100 MHz, δ ppm): 21.6, 23.5, 44.04, 55.6, 116.0; $^{31}$P NMR (in DMSO-$d_6$ and $H_3PO_4$ 85% in water as external standard, 162 MHz, δ ppm): 122.25 (s, OPON), 144.47 (s, OPOO), 185.52 (s, OPOCl); HR-MS (ESI-TOF) (m/z): calcd, 470.0805; found, 471.1115 [M$^+$+H].

Preparation of polymer-bound β-triphosphitylating reagent: Polymer-bound O—[(O,O-bis(2-cyanoethyl)phosphoryl]-O-[2-cyanoethylphosphoryl]diisopropylaminophosphoramidite (58)

The prepared reaction mixture containing 30 in THF (10 mmol) was added to a swelled solution of polymer-bound N-Boc p-acetoxybenzyl alcohol 31B (3.75 g, 0.72 mmol/g) and triethylamine (1.4 mL, 10 mmol) in anhydrous THF (25 mL). The mixture was shaken for 30 h at room temperature. The resin was collected by filtration, washed with THF (2×30 mL), DCM (2×30 mL), and MeOH (2×30 mL), respectively, and was dried overnight under vacuum to give 58 (4.94 g, 93%, 0.51 mmol/g). IR (cm$^{-1}$): 2261 (CN), 1756 (C=O ester), 1033 (P—O—C).

Solid-Phase β-Triphosphorylation of Unprotected Nucleosides Using Polymer-Bound β-Triphosphitylating Reagent 58.

Preparation of polymer-bound 5-O—[O—[(O,O-bis(2-cyanoethyl)phosphoryl]-O-[2-cyanoethylphosphoryl]phosphite triester]adenosine (59a), 5-O—[O—[(O,O-bis(2-cyanoethyl)phosphoryl]-O-[2-cyanoethylphosphoryl]phosphite triester]uridine (59b), 5-O—[O—[(O,O-bis(2-cyanoethyl)phosphoryl]-O-[2-cyanoethylphosphoryl]phosphite triester]-3-azido-3-deoxythymidine (59c), 5-O-[O—[(O,O-bis(2-cyanoethyl)phosphoryl]-O-[2-cyanoethylphosphoryl]phosphite triester]thymidine (59d), 5-O—[O—[O,O-bis(2-cyanoethyl)phosphoryl]-O-[2-cyanoethylphosphoryl]phosphite triester]inosine (59e), and 5-O—[O—[(O,O-bis(2-cyanoethyl)phosphoryl]-O-[2-cyanoethylphosphoryl]phosphite triester]cytidine (59f)

Unprotected nucleosides (a-f, 2.0 mmol) and 1H-tetrazole (71 mg, 1.0 mmol) were added to 58 (790 mg, 0.51 mmol/g) in anhydrous THF (2 mL) and DMSO (3 mL) in case of uridine, 3'-azido-3'-deoxythymidine, thymidine, and inosine or in anhydrous DMSO (5 mL) in case of adenosine and cytidine. The mixtures were shaken for 24 h at room temperature. The resins were collected by filtration and washed with DMSO (2×30 mL), THF (2×30 mL), and MeOH (3×30 mL), respectively, and dried under vacuum to give 59a-f (877-891 mg). IR (cm$^{-1}$): 59a: 3335 (OH), 2259 (CN), 1761 (C=O ester), 1024 (P—O—C); 59b: 3342 (OH), 2251 (CN), 1762 (C=O ester), 1027 (P—O—C); 59c: 2344 (CN), 1760 (C=O ester), 1030 (P—O—C); 59d: 3348 (OH), 2262 (CN), 1759 (C=O ester), 1022 (P—O—C); 59e: 3317 (OH), 2257 (CN), 1759 (C=O ester), 1025 (P—O—C); 59f: 3349 (OH), 2251 (CN), 1765 (C=O ester), 1034 (P—O—C).

Oxidation of polymer-bound α-triphosphitylated precursors, 59a-f, to Polymer-bound 5-O—[O—[(O,O-bis(2-cyanoethyl)phosphoryl]-O-[2-cyanoethylphosphoryl]phosphate triester]adenosine (60a), 5-O—[O—[(O,O-bis(2-cyanoethyl)phosphoryl]-O-[2-cyanoethylphosphoryl]phosphate triester]uridine (60b), 5-O—[O—[(O,O-bis(2-cyanoethyl)phosphoryl]-O-[2-cyanoethylphosphoryl]phosphate triester]-3-azido-3-deoxythymidine (60c), 5-O-[O—[(O,O-bis(2-cyanoethyl)phosphoryl]-O-[2-cyanoethylphosphoryl]phosphate triester]thymidine (60d), 5-O—[O—[(O,O-bis(2-cyanoethyl)phosphoryl]-O-[2-cyanoethylphosphoryl]phosphate triester]inosine (60e), and 5-O—[O—[(O,O-bis(2-cyanoethyl)phosphoryl]-O-[2-cyanoethylphosphoryl]phosphate triester]cytidine (60f)

t-Butyl hydroperoxide in decane (5-6 M, 1.2 mL, 6.0 mmol) was added to the resins 59a-f (877-891 mg) in THF (4 mL). After 1 h shaking at room temperature, the resins were collected by filtration and washed with THF (3×15 mL) and MeOH (3×15 mL), respectively, and were dried overnight at room temperature under vacuum to give 60a-f (893-908 mg). IR (cm$^{-1}$): 60a: 3306 (OH), 2262 (CN), 1766 (C=O ester), 1023 (P—O—C); 60b: 3317 (OH), 2262 (CN), 1758 (C=O ester), 1030 (P—O—C); 60c: 2257 (CN), 1762 (C=O ester), 1029 (P—O—C); 60d: 3338 (OH), 2251 (CN), 1765 (C=O ester), 1030 (P—O—C); 60e: 3335 (OH), 2258 (CN), 1755 (C=O ester), 1024 (P—O—C); 60f: 3327 (OH), 2265 (CN), 1752 (C=O ester), 1033 (P—O—C).

Preparation of polymer-bound adenosine-5-O-β-triphosphotriester (61a), uridine-5-O-β-triphosphotriester (61b), 3-azido-3-deoxythymidine-5-O-β-triphosphotriester (61c), thymidine-5-O-β-triphosphotriester (61d), inosine-5-O-β-triphosphotriester (61e), and cytidine-5-O-β-triphosphotriester (61f)

To the swelled resins 60a-f (893-908 mg) in THF (4 mL) was added DBU (600 µL, 4 mmol). After 48 h shaking of the mixture at room temperature, the resins were collected by filtration and washed with THF (2×20 mL) and MeOH (3×10 mL), respectively, and were dried overnight at room temperature under vacuum to give 61a-f (813-859 mg). IR (cm$^{-1}$): 61a: 3324 (O—H), 1691 (C=O ester), 1030 (P—O—C); 61b: 3334 (O—H), 1752 (C=O ester), 1028 (P—O—C); 61c: 1751 (C=O ester), 1030 (P—O—C); 61d: 3359 (O—H), 1753 (C=O ester), 1031 (P—O—C); 61e: 3331 (O—H), 1747 (C=O ester), 1027 (P—O—C); 61f: 3356 (O—H), 1741 (C=O ester), 1026 (P—O—C).

Preparation of adenosine-5-O-β-triphosphate (63a), uridine-5-O-β-triphosphate (63b), 3-azido-3-deoxythymidine-5-O-β-triphosphate (63c), thymidine-5-O-β-triphosphate (63d), inosine-5-O-β-triphosphate (63e), and cytidine-5-O-β-triphosphate (63f)

To the swelled resins 61a-f (813-859 mg) in anhydrous DCM (2 mL) was added DCM/TFA/water (74:24:2 v/v, 4 mL). After 30 min shaking of the mixtures at room temperature, the resins were collected by filtration and washed with DCM (10 mL), THF (10 mL), and MeOH (10 mL), respectively. The solvents of the filtrate solutions were evaporated immediately at −20° C. The residues were mixed with Amberlite AG-50W-X8 (100-200 mesh, hydrogen form, 1.0 g, 1.7 meq/g) in water:dioxane (75:25 v/v, 5 mL) for 15 min at −20° C. After filtration, the solvents were removed using lyophilization and the crude products were purified on a $C_{18}$ Sep-Pak using appropriate solvents. The solvents were evaporated and the residues were dried under vacuum at −20° C. to yield 63a-f. The purity and total isolated yields for 63a-f are shown in Table 5. The compounds were characterized by $^1$H NMR, $^{13}$C NMR, $^{31}$P NMR, high resolution mass spectrometer (ESI-TOF), and quantitative phosphorus elemental analysis.

Adenosine-5-O-β-triphosphate (63a). $^1$H NMR (DMSO-d$_6$, 400 MHz, δ ppm): δ 3.50-3.62 (m, 1H), 3.65-3.77 (m, 1H), 3.96-4.07 (m, 1H), 4.12-4.24 (m, 1H), 4.60-4.70 (m, 1H), 5.20-5.30 (m, 1H), 5.45-5.62 (m, 2H), 5.90-6.98 (m, 1H), 7.35-7.52 (br s, 2H), 8.19 (s, 1H), 8.40 (s, 1H); $^{13}$C NMR (DMSO-d$_6$, 100 MHz, δ ppm): δ 62.7, 71.8, 74.6, 87.0, 89.1, 120.5, 141.2, 150.1, 153.6, 157.3; $^{31}$P NMR (in DMSO-d$_6$ and H$_3$PO$_4$ 85% in water as external standard, 162 MHz, δ ppm): −13.00 (t, $J_{\beta,\alpha}$=11 Hz, β-P, 1P), 2.90 (d, $J_{\alpha,\beta}$=11 Hz, α-P, 2P); HR-MS (ESI-TOF) (m/z): calcd, 506.9957; found, 507.8198 [M$^+$+H]; Anal. Calcd. P 18.32%, found 18.19%.

Uridine-5-O-β-triphosphate (63b). $^1$H NMR (DMSO-d$_6$, 400 MHz, δ ppm): 3.48-3.68 (m, 2H), 3.79-3.88 (m, 1H), 3.92-4.00 (m, 1H), 4.01-4.07 (m, 1H), 4.90-5.20 (br s, OH), 5.20-5.52 (br s, OH), 5.67 (d, $J_{5,6}$=8.0 Hz, 1H), 5.79 (d, $J_{1',2'}$=8.0 Hz, 1H), 7.90 (d, $J_{6,5}$=8.0 Hz, 1H), 10.85-11.50 (br s, 1H); $^{13}$C NMR (DMSO-d$_6$, 100 MHz, δ ppm): 61.8, 70.9, 74.6, 85.8, 88.7, 102.8, 141.9, 151.9, 164.4; $^{31}$P NMR (in DMSO-d$_6$ and H$_3$PO$_4$ 85% in water as external standard, 162 MHz, δ ppm): −14.87 (t, $J_{\beta,\alpha}$=10 Hz, β-P, 1P), 3.26 (d, $J_{\alpha,\beta}$=10 Hz, α-P, 2P); HR-MS (ESI-TOF) (m/z) calcd, 483.9685; found, 484.0307 [M]$^+$; Anal. Calcd, P 19.19%; found 19.30%.

3'-Azido-3'-deoxythymidine-5-O-β-triphosphate (63c). $^1$H NMR (DMSO-d$_6$, 400 MHz, δ ppm): 1.78 (d, $J_{5-CH_3,6}$=1.1 Hz, 3H), 2.23-2.31 (m, 1H), 2.32-2.42 (m, 1H), 3.55-3.75 (m, 2H), 3.75-3.85 (m, 1H), 4.36-4.43 (m, 1H), 5.10-5.35 (br s, 1H), 6.13 (t, $J_{1',2'}$=6.0 Hz, 1H), 7.72 (d, $J_{6,5-CH_3}$=1.1 Hz, 1H), 11.15-11.45 (br s, 1H); $^{13}$C NMR (DMSO-d$_6$, 100 MHz, δ ppm): 13.1, 37.3, 61.1, 61.8, 84.5, 85.1, 110.6, 137.1, 151.5, 164.9; $^{31}$P NMR (in DMSO-d$_6$ and H$_3$PO$_4$ 85% in water as external standard, 162 MHz, δ ppm): −15.18 (t, $J_{\beta,\alpha}$=9 Hz, β-P, 1P), 2.78 (d, $J_{\alpha,\beta}$=9 Hz, α-P, 2P); HR-MS (ESI-TOF) (m/z): calcd, 506.9957; found, 507.8571 [M$^+$+H]; Anal. Calcd, P 18.32%; found 18.46%.

Thymidine-5-O-β-triphosphate (63d). $^1$H NMR (DMSO-d$_6$, 400 MHz, δ ppm): 1.74 (d, $J_{5-CH_3,6}$=1.1 Hz, 3H), 2.10-2.11 (m, 2H), 3.49-3.65 (m, 2H), 3.72-3.80 (m, 1H), 4.19-4.28 (m, 1H), 4.95-5.05 (m, 1H), 5.15-5.25 (m, 1H), 6.17 (t, $J_{1',2'}$ and $J_{1',2'}$=8.0 Hz, 1H), 7.69 (d, $J_{6,5-CH_3}$=1.1 Hz, 1H), 11.05-11.15 (br s, 1H); $^{13}$C NMR (DMSO-d$_6$, 100 MHz, δ ppm): 13.2, 40.8, 62.3, 71.5, 84.8, 88.2, 110.5, 137.2, 151.6, 164.9; $^{31}$P NMR (in DMSO-d$_6$ and H$_3$PO$_4$ 85% in water as external standard, 162 MHz, δ ppm): −17.83 (t, $J_{\beta,\alpha}$=11 Hz, β-P, 1P), 1.66 (d, $J_{\alpha,\beta}$=11 Hz, α-P, 2P); HR-MS (ESI-TOF) (m/z): calcd, 481.9893; found, 481.6183 [M]$^+$; Anal. Calcd, P 19.27%; found 19.52%.

Inosine-5-O-β-triphosphate (63e). $^1$H NMR (DMSO-d$_6$, 400 MHz, δ ppm): 3.50-3.62 (m, 1H), 3.63-3.75 (m, 1H), 3.95-4.03 (m, 1H), 4.12-4.23 (m, 1H), 4.45-4.60 (m, 1H), 5.10-5.20 (m, 1H), 5.22-5.35 (m, 1H), 5.52-5.65 (m, 1H), 5.87-5.90 (m, 1H), 8.13 (s, 1H), 8.38 (s, 1H); 12.41-12.50 (br s, 1H); $^{13}$C NMR (DMSO-d$_6$, 100 MHz, δ ppm): 62.1, 71.2, 75.0, 86.5, 88.4, 125.2, 139.8, 146.9, 149.1, 157.6; $^{31}$P NMR (in DMSO-d$_6$ and H$_3$PO$_4$ 85% in water as external standard, 162 MHz, δ ppm): −15.39 (t, $J_{\beta,\alpha}$=10 Hz, β-P, 1P), 3.24 (d, $J_{\alpha,\beta}$=10 Hz, α-P, 2P); HR-MS (ESI-TOF) (m/z): calcd, 507.9798; found, 508.8164 [M$^+$+H]; Anal. Calcd, P 18.29%; found 18.37%.

Cytidine-5-O-β-triphosphate (63f). $^1$H NMR (DMSO-d$_6$, 400 MHz, δ ppm): 3.48-3.61 (m, 1H), 3.62-3.72 (m, 1H), 3.80-3.90 (m, 1H), 3.94-4.20 (m, 2H), 5.10-5.25 (br s, OH), 5.40-5.55 (br s, OH), 5.75-5.90 (m, 2H), 7.35-7.55 (br s, 2H), 7.89 (d, $J_{6,5}$=8.0 Hz, 1H); $^{13}$C NMR (DMSO-d$_6$, 100 MHz, δ ppm): 61.6, 70.4, 74.9, 85.1, 89.9, 95.4, 142.5, 156.7, 166.5; $^{31}$P NMR (in DMSO-d$_6$ and H$_3$PO$_4$ 85% in water as external standard, 162 MHz, δ ppm): −11.57 (t, $J_{\beta,\alpha}$=11 Hz, β-P, 1P), 1.80 (d, $J_{\alpha,\beta}$=11 Hz, α-P, 2P); HR-MS (ESI-TOF) (m/z): calcd, 482.9845; found, 484.0020 [M$^+$+H]; Anal. Calcd, P 19.23%; found 18.98%.

Although the present invention has been shown and described with a preferred embodiment thereof, various changes, omissions and additions to the form and detail thereof, may be made therein, without departing from the spirit and scope of the invention.

What is claim is:

1. A polymer-bound phosphitylating reagent wherein, said polymer-bound phosphitylating reagent includes a diphosphite or triphosophite that includes phosphorus atoms that are linked together through known phosphorus atom linking agents, namely oxygen, amino, sulfur, or methylene groups and/or the phosphorus atoms are substituted with another protective agent for protecting the reagent, namely any of chlorine, diisopropylamine and cyanoethoxy groups.

2. A polymer-bound linker of p-acetoxy benzyl alcohol and p-acetoxy benzaldehyde attached directly or indirectly to a phosphitylating reagent including a diphosphite or triphosphite that includes phosphorus atoms that are linked together through known phosphorus atom linking agents, namely any of oxygen, sulfur, amino, or methylene groups and/or are substituted with another protective agent for protecting the diphosphite or triphosphite, namely chlorine, diisopropylamine and cyanoethoxy groups.

3. The phosphitylating reagent of claim 2, wherein one or more bridging oxygens between phosphorus atoms are replaced with NH, S, or $CH_2$.

4. The polymer-bound phosphitylating reagent of claim 1, wherein the polymer-bound phosphitylating reagent is capable of being modified to form nucleoside and carbohydrate diphosphates, triphosphates, tetraphosphates, β-triphosphates, diphosphodiesters, triphosphodiesters, tetraphosphodiesters and/or starting materials for the synthesis of other compounds.

5. The polymer-bound phosphitylating reagent of claim 1, wherein the polymer-bound phosphitylating reagent is capable of being used for the synthesis of nucleoside and carbohydrate diphosphates, triphosphates, tetraphosphates, β-triphosphates, diphosphodiesters, triphosphodiesters, and tetraphosphodiesters.

6. A polymer-bound phosphitylating reagent wherein, said polymer-bound phosphitylating reagent includes a diphosphite, triphosophite, tetraphosphite, or β-triphosphite that includes phosphorus atoms that are linked together through known phosphorus atom linking agents, namely oxygen, amino, sulfur, or methylene groups and/or the phosphorus atoms are substituted with another protective agent for protecting the reagent, namely any of chlorine, diisopropylamine and cyanoethoxy groups.

7. The polymer-bound phosphitylating reagent of claim 6, wherein the polymer-bound phosphitylating reagent is capable of being modified to form nucleoside and carbohydrate diphosphates, triphosphates, tetraphosphates, β-triphosphates, diphosphodiesters, triphosphodiesters, tetraphosphodiesters and/or starting materials for the synthesis of other compounds.

8. The polymer-bound phosphitylating reagent of claim 6, wherein the polymer-bound phosphitylating reagent is capable of being used for the synthesis of nucleoside and carbohydrate diphosphates, triphosphates, tetraphosphates, β-triphosphates, diphosphodiesters, triphosphodiesters, and tetraphosphodiesters.

9. A polymer-bound linker of p-acetoxy benzyl alcohol and p-acetoxy benzaldehyde attached directly or indirectly to a phosphitylating reagent including a diphosphite, triphosphate, tetraphosphite, or β-triphosphite, that includes phosphorus atoms that are linked together through known phosphorus atom linking agents, namely any of oxygen, sulfur, amino, or methylene groups and/or are substituted with another protective agent for protecting the diphosphite, triphosphite, tetraphosphite, or β-triphosphite namely chlorine, diisopropylamine and cyanoethoxy groups.

10. The phosphitylating reagent of claim 9, wherein one or more bridging oxygens between phosphorus atoms are replaced with NH, S, or $CH_2$.

* * * * *

UNITED STATES PATENT AND TRADEMARK OFFICE
CERTIFICATE OF CORRECTION

PATENT NO.          : 8,193,384 B2
APPLICATION NO.     : 11/972254
DATED               : June 5, 2012
INVENTOR(S)         : Keykavous Parang and Yousef Ahamdibeni It is certified that error appears in the above-identified patent and that said Letters Patent is hereby corrected as shown below:

In Col. 12, line 56, please delete "1H-tetrazole" and replace with "1H-terazole".

In Col. 17, line 50, please delete "diisopropylphosphoramidite" and replace with "diisoproylphosphoramidite".

In Col. 48, line 50, please delete "triphosphate" and replace with "triphosphite".

Signed and Sealed this
Twenty-fourth Day of July, 2012

David J. Kappos
*Director of the United States Patent and Trademark Office*